US011891608B2

(12) United States Patent
Geall

(10) Patent No.: US 11,891,608 B2
(45) Date of Patent: *Feb. 6, 2024

(54) IMMUNIZATION OF LARGE MAMMALS WITH LOW DOSES OF RNA

(71) Applicant: GLAXOSMITHKLINE BIOLOGICALS SA, Rixensart (BE)

(72) Inventor: Andrew Geall, Littleton, MA (US)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 18/080,150

(22) Filed: Dec. 13, 2022

(65) Prior Publication Data

US 2023/0136704 A1 May 4, 2023

Related U.S. Application Data

(63) Continuation of application No. 16/656,929, filed on Oct. 18, 2019, now Pat. No. 11,655,475, which is a continuation of application No. 13/808,153, filed as application No. PCT/US2011/043096 on Jul. 6, 2011, now Pat. No. 10,487,332.

(60) Provisional application No. 61/361,794, filed on Jul. 6, 2010.

(51) Int. Cl.
| | |
|---|---|
| C12N 15/117 | (2010.01) |
| C12N 15/86 | (2006.01) |
| A61K 39/155 | (2006.01) |
| A61K 39/39 | (2006.01) |
| A61K 39/12 | (2006.01) |
| A61P 31/12 | (2006.01) |
| A61P 37/04 | (2006.01) |
| A61K 48/00 | (2006.01) |
| A61K 39/00 | (2006.01) |

(52) U.S. Cl.
CPC ............ *C12N 15/117* (2013.01); *A61K 39/12* (2013.01); *A61K 39/155* (2013.01); *A61K 39/39* (2013.01); *A61K 48/0041* (2013.01); *A61K 48/0083* (2013.01); *A61P 31/12* (2018.01); *A61P 37/04* (2018.01); *C12N 15/86* (2013.01); *A61K 2039/53* (2013.01); *A61K 2039/552* (2013.01); *A61K 2039/55555* (2013.01); *A61K 2039/55566* (2013.01); *C12N 2760/18534* (2013.01); *C12N 2770/36143* (2013.01); *C12N 2820/60* (2013.01)

(58) Field of Classification Search
CPC ......... A61K 2039/53; A61K 2039/552; A61K 2039/55555; A61K 2039/55566; A61K 39/12; A61K 39/155; A61K 39/39; A61P 31/04; A61P 31/10; A61P 31/12; A61P 33/00; A61P 37/04; C12N 15/117; C12N 15/86; C12N 2760/18534; C12N 2770/36143; C12N 2820/60

USPC ................. 424/93.21, 450; 435/458
See application file for complete search history.

(56) References Cited

U.S. PATENT DOCUMENTS

| | | | |
|---|---|---|---|
| 5,013,556 | A | 5/1991 | Woodle et al. |
| 5,279,833 | A | 1/1994 | Rose |
| 5,459,127 | A | 10/1995 | Felgner et al. |
| 5,474,914 | A | 12/1995 | Spaete |
| 5,750,390 | A | 5/1998 | Thompson et al. |
| 5,814,482 | A | 9/1998 | Dubensky, Jr. et al. |
| 5,843,723 | A | 12/1998 | Dubensky, Jr |
| 5,885,613 | A | 3/1999 | Holland |
| 5,965,434 | A | 10/1999 | Wolff et al. |
| 5,972,704 | A | 10/1999 | Draper et al. |
| 6,009,406 | A | 12/1999 | Nick |
| 6,015,686 | A | 1/2000 | Dubensky et al. |
| 6,048,546 | A | 4/2000 | Sasaki et al. |
| 6,060,308 | A | 5/2000 | Parrington |
| 6,090,406 | A | 7/2000 | Popescu et al. |
| 6,156,558 | A | 12/2000 | Johnston et al. |
| 6,395,302 | B1 | 5/2002 | Hennink et al. |
| 6,432,925 | B1 | 8/2002 | Hoon et al. |
| 6,602,705 | B1 | 8/2003 | Barnett et al. |
| 6,610,321 | B2 | 8/2003 | Huang et al. |
| 6,790,449 | B2 | 9/2004 | Collins |
| 6,815,432 | B2 | 11/2004 | Wheeler et al. |
| 6,858,225 | B2 | 2/2005 | Semple et al. |
| 6,890,554 | B2 | 5/2005 | Jessee et al. |
| 7,250,404 | B2 | 7/2007 | Feigner et al. |
| 7,303,881 | B2 | 12/2007 | Huang et al. |
| 7,384,923 | B2 | 6/2008 | Gregoriadis |

(Continued)

FOREIGN PATENT DOCUMENTS

| | | |
|---|---|---|
| BR | 112012001666 | 9/2019 |
| EP | 0786522 | 7/1997 |

(Continued)

OTHER PUBLICATIONS

Yoder, et al., "Role of Complement in Neutralization of Respiratory Syncytial Virus" J Med Virol., 2004; pp. 688-694; vol. 72.
Yoffe, "Predicting the sizes of large RNA molecules" PNAS; vol. 105; 2008; pp. 16153-16158.
Yoneyama, et al., "RIG-I family RNA helicases: cytoplasmic sensor for antiviral innate immunity," Cytokine & Growth Factor Review S, (2007), vol. 18, pp. 545-551.
Yoon, et al., "DNA-Mediated Immunization of Mice with Plasmid Encoding HBs Antigen." J. Korean Med Sci; 1999; pp. 187-192; vol. 14.

(Continued)

Primary Examiner — Janet L Epps-Smith
(74) Attorney, Agent, or Firm — GREENBLUM & BERNSTEIN, P.L.C.

(57) ABSTRACT

RNA encoding an immunogen is delivered to a large mammal at a dose of between 2 μg and 100 μg. Thus, the invention provides a method of raising an immune response in a large mammal, comprising administering to the mammal a dose of between 2 μg and 100 μg of immunogen-encoding RNA. Similarly, RNA encoding an immunogen can be delivered to a large mammal at a dose of 3 ng/kg to 150 ng/kg. The delivered RNA can elicit an immune response in the large mammal.

30 Claims, 8 Drawing Sheets

(56) References Cited

U.S. PATENT DOCUMENTS

| | | |
|---|---|---|
| 7,422,902 B1 | 9/2008 | Wheeler et al. |
| 7,442,381 B2 | 10/2008 | Smith et al. |
| 7,557,200 B2 | 7/2009 | Wu et al. |
| 7,604,803 B2 | 10/2009 | Bacon et al. |
| 7,691,405 B2 | 4/2010 | Chen et al. |
| 7,745,651 B2 | 6/2010 | Heyes et al. |
| 7,799,565 B2 | 9/2010 | MacLachlan et al. |
| 7,811,812 B2 | 10/2010 | Dubensky et al. |
| 7,862,829 B2 | 1/2011 | Johnston et al. |
| 7,977,091 B2 | 7/2011 | Dubensky et al. |
| 8,058,069 B2 | 11/2011 | Yaworski et al. |
| 8,338,583 B2 | 12/2012 | Michaeli |
| 8,877,206 B2 | 11/2014 | Chen et al. |
| 9,254,265 B2 | 2/2016 | Geall et al. |
| 9,504,651 B2 | 11/2016 | MacLachlan et al. |
| 9,770,463 B2 | 9/2017 | Geall et al. |
| 9,801,897 B2 | 10/2017 | Geall et al. |
| 9,801,987 B2 | 10/2017 | Farnan et al. |
| 10,188,748 B2 | 1/2019 | Mulbe et al. |
| 10,487,332 B2 | 11/2019 | Geall |
| 10,532,067 B2 | 1/2020 | Geall et al. |
| 10,906,867 B2 | 2/2021 | Brito et al. |
| 11,026,964 B2 | 6/2021 | Geall et al. |
| 11,058,762 B2 | 7/2021 | Geall et al. |
| 11,078,237 B2 | 8/2021 | Franti et al. |
| 11,291,635 B2 | 4/2022 | Geall et al. |
| 11,291,682 B2 | 4/2022 | Geall et al. |
| 11,324,770 B2 | 5/2022 | Geall et al. |
| 2003/0091591 A1 | 5/2003 | Xiong et al. |
| 2003/0096397 A1 | 5/2003 | Schlesinger |
| 2003/0124134 A1 | 7/2003 | Edwards et al. |
| 2003/0138453 A1 | 7/2003 | O'Hagan et al. |
| 2003/0203865 A1 | 10/2003 | Harvie |
| 2003/0212022 A1 | 11/2003 | Vogel et al. |
| 2003/0232058 A1 | 12/2003 | Dubensky, Jr. |
| 2004/0142025 A1 | 7/2004 | MacLachlan et al. |
| 2004/0208848 A1 | 10/2004 | Smith et al. |
| 2004/0228842 A1 | 11/2004 | Lu et al. |
| 2005/0032730 A1 | 2/2005 | Von Der Mulbe et al. |
| 2005/0042230 A1 | 2/2005 | Anderson et al. |
| 2005/0064026 A1 | 3/2005 | Garidel et al. |
| 2005/0064595 A1 | 3/2005 | Maclachlan et al. |
| 2005/0118566 A1 | 6/2005 | Escriou et al. |
| 2005/0266550 A1 | 12/2005 | Rayner et al. |
| 2006/0002991 A1 | 1/2006 | Essler et al. |
| 2006/0051405 A1 | 3/2006 | Maclachlan et al. |
| 2006/0063732 A1 | 3/2006 | Vogel et al. |
| 2006/0083780 A1 | 4/2006 | Heyes et al. |
| 2006/0177819 A1 | 8/2006 | Smith et al. |
| 2006/0240554 A1 | 10/2006 | Chen et al. |
| 2006/0251620 A1 | 11/2006 | Ivanova |
| 2007/0014805 A1 | 1/2007 | Dalencon et al. |
| 2007/0118094 A1 | 5/2007 | Bingham et al. |
| 2007/0207526 A1 | 9/2007 | Coit |
| 2008/0057080 A1 | 3/2008 | Luke et al. |
| 2008/0085870 A1 | 4/2008 | Hermanson et al. |
| 2008/0187545 A1 | 8/2008 | Shenk et al. |
| 2008/0249046 A1 | 10/2008 | MacLachlan et al. |
| 2008/0260698 A1 | 10/2008 | Weaver |
| 2008/0311158 A1 | 12/2008 | Merola |
| 2009/0068221 A1 | 3/2009 | Morrison |
| 2009/0075384 A1 | 3/2009 | Kamrud |
| 2009/0104226 A1 | 4/2009 | Perri et al. |
| 2009/0143323 A1 | 6/2009 | Bavari |
| 2010/0040650 A1 | 2/2010 | Crowe et al. |
| 2010/0092481 A1 | 4/2010 | Lanzavecchia |
| 2010/0173980 A1 | 7/2010 | Valliant et al. |
| 2010/0196492 A1 | 8/2010 | Green et al. |
| 2010/0285112 A1 | 11/2010 | Novobrantseva |
| 2011/0053893 A1 | 3/2011 | Wu et al. |
| 2011/0070260 A1 | 3/2011 | Baric et al. |
| 2011/0076335 A1 | 3/2011 | Yaworski et al. |
| 2011/0117125 A1 | 5/2011 | Hope et al. |
| 2011/0200582 A1 | 8/2011 | Baryza |
| 2011/0200667 A1 | 8/2011 | Contreras et al. |
| 2011/0229969 A1 | 9/2011 | Sandig et al. |
| 2011/0244026 A1 | 10/2011 | Guild et al. |
| 2011/0300205 A1 | 12/2011 | Geall |
| 2011/0305727 A1 | 12/2011 | Swanson et al. |
| 2012/0030901 A1 | 2/2012 | Manninen et al. |
| 2012/0100207 A1 | 4/2012 | Motokui et al. |
| 2012/0156251 A1 | 6/2012 | Brito et al. |
| 2012/0177677 A1 | 7/2012 | Carmon |
| 2012/0195936 A1 | 8/2012 | Carten et al. |
| 2012/0237546 A1 | 9/2012 | Singh et al. |
| 2013/0101609 A1 | 4/2013 | O'Hagan et al. |
| 2013/0149375 A1 | 6/2013 | Geall |
| 2013/0164289 A1 | 6/2013 | McVoy et al. |
| 2013/0171185 A1 | 7/2013 | Settembre et al. |
| 2013/0171241 A1 | 7/2013 | Geall |
| 2013/0177639 A1 | 7/2013 | Geall et al. |
| 2013/0177640 A1 | 7/2013 | Geall et al. |
| 2013/0183355 A1 | 7/2013 | Jain et al. |
| 2013/0189351 A1 | 7/2013 | Geall |
| 2013/0195968 A1 | 8/2013 | Geall |
| 2013/0195969 A1 | 8/2013 | Geall et al. |
| 2013/0202684 A1 | 8/2013 | Geall |
| 2013/0225409 A1 | 8/2013 | Allen et al. |
| 2013/0245105 A1 | 9/2013 | De Fougerolles et al. |
| 2014/0030292 A1 | 1/2014 | Franti et al. |
| 2014/0044751 A1 | 2/2014 | Dormitzer |
| 2014/0141070 A1 | 5/2014 | Geall et al. |
| 2014/0193484 A1 | 7/2014 | Bertholet Girardin et al. |
| 2014/0212498 A1 | 7/2014 | Brito et al. |
| 2014/0220083 A1 | 8/2014 | Brito et al. |
| 2014/0227346 A1 | 8/2014 | Geall et al. |
| 2014/0242152 A1 | 8/2014 | Geall et al. |
| 2014/0248314 A1 | 9/2014 | Swanson et al. |
| 2014/0255472 A1 | 9/2014 | Geall |
| 2014/0271829 A1 | 9/2014 | Lilja et al. |
| 2014/0275227 A1 | 9/2014 | Hoge et al. |
| 2014/0303232 A1 | 10/2014 | Baryza et al. |
| 2014/0348863 A1 | 11/2014 | Bianchi et al. |
| 2015/0017251 A1 | 1/2015 | Malvala et al. |
| 2016/0024157 A1 | 1/2016 | Masignani et al. |
| 2016/0129105 A1 | 5/2016 | Mülbe et al. |
| 2018/0094033 A1 | 4/2018 | Telford et al. |
| 2019/0343862 A1 | 11/2019 | Geall |
| 2020/0048636 A1 | 2/2020 | Geall |
| 2020/0069793 A1 | 3/2020 | Ciaramella |
| 2020/0113830 A1 | 4/2020 | Geall et al. |
| 2020/0113831 A1 | 4/2020 | Geall et al. |
| 2020/0230058 A1 | 7/2020 | Geall et al. |
| 2020/0323896 A1 | 10/2020 | Geall |
| 2021/0290755 A1 | 8/2021 | Geall et al. |
| 2021/0268013 A1 | 9/2021 | Geall et al. |
| 2022/0054525 A1 | 2/2022 | Geall et al. |
| 2022/0056449 A1 | 2/2022 | Geall |
| 2022/0119455 A1 | 4/2022 | Franti et al. |
| 2022/0192997 A1 | 6/2022 | Geall et al. |
| 2022/0213149 A1 | 7/2022 | Franti et al. |

FOREIGN PATENT DOCUMENTS

| | | |
|---|---|---|
| EP | 1083232 | 3/2001 |
| EP | 0880360 | 10/2002 |
| EP | 1392341 | 3/2004 |
| EP | 1637144 | 3/2006 |
| EP | 1764089 | 3/2007 |
| EP | 2338478 | 6/2011 |
| EP | 2510099 | 10/2012 |
| EP | 2578685 | 4/2013 |
| EP | 2791160 | 10/2014 |
| EP | 2590626 | 10/2015 |
| EP | 2591114 | 6/2016 |
| EP | 2590676 | 8/2016 |
| EP | 3336082 | 6/2018 |
| EP | 2750707 | 10/2018 |
| EP | 3318248 | 4/2019 |
| EP | 3492109 | 6/2019 |
| EP | 2591103 | 8/2019 |
| EP | 3611266 | 2/2020 |
| EP | 3682905 | 7/2020 |
| EP | 2729126 | 12/2020 |

(56) References Cited

FOREIGN PATENT DOCUMENTS

| | | |
|---|---|---|
| JP | 2000505802 | 5/2000 |
| JP | 2007112768 | 5/2007 |
| JP | 2007521247 | 8/2007 |
| JP | 2008501729 | 1/2008 |
| JP | 2009510097 | 3/2009 |
| JP | 2009539845 | 11/2009 |
| JP | 2010025644 | 2/2010 |
| JP | 2010528591 | 8/2010 |
| JP | 2011504802 | 2/2011 |
| WO | 8900812 | 2/1989 |
| WO | 9011092 | 10/1990 |
| WO | 9219752 | 11/1992 |
| WO | 1993024640 | 12/1993 |
| WO | 9527721 | 10/1995 |
| WO | 9608235 | 3/1996 |
| WO | 9617072 | 6/1996 |
| WO | 9728818 | 8/1997 |
| WO | 1997030170 | 8/1997 |
| WO | 1998010748 | 3/1998 |
| WO | 1998051278 | 11/1998 |
| WO | 1999011808 | 3/1999 |
| WO | 9928487 | 6/1999 |
| WO | 9930733 | 6/1999 |
| WO | 1999052503 | 10/1999 |
| WO | 9955310 | 11/1999 |
| WO | 0003683 | 1/2000 |
| WO | 2000000617 | 1/2000 |
| WO | 200129233 | 4/2001 |
| WO | 200179253 | 10/2001 |
| WO | 0193836 | 12/2001 |
| WO | 2002002606 | 1/2002 |
| WO | 200209645 | 2/2002 |
| WO | 2002026209 | 4/2002 |
| WO | 2002034771 | 5/2002 |
| WO | 2002061113 | 8/2002 |
| WO | 02074920 | 9/2002 |
| WO | 2002072027 | 9/2002 |
| WO | 2002079239 | 10/2002 |
| WO | 2002095023 | 11/2002 |
| WO | 2002098443 | 12/2002 |
| WO | 2003018054 | 3/2003 |
| WO | 2003068190 | 8/2003 |
| WO | 2004076645 | 9/2004 |
| WO | 2004098509 | 11/2004 |
| WO | 2005002619 | 1/2005 |
| WO | 2005007689 | 1/2005 |
| WO | 2005032582 | 4/2005 |
| WO | 2005046621 | 5/2005 |
| WO | 2005060934 | 7/2005 |
| WO | 2005111066 | 11/2005 |
| WO | 2005113781 | 12/2005 |
| WO | 2005113782 | 12/2005 |
| WO | 2005120152 | 12/2005 |
| WO | 2005121348 | 12/2005 |
| WO | 2006053646 | 5/2006 |
| WO | 2006061643 | 6/2006 |
| WO | 2006078294 | 7/2006 |
| WO | 2006089264 | 8/2006 |
| WO | 2006091517 | 8/2006 |
| WO | 2006092607 | 9/2006 |
| WO | 2006094756 | 9/2006 |
| WO | 2006110413 | 10/2006 |
| WO | 2006138004 | 12/2006 |
| WO | 2007014754 | 2/2007 |
| WO | 2007024708 | 3/2007 |
| WO | 2007036366 | 4/2007 |
| WO | 2007041270 | 4/2007 |
| WO | 2007047749 | 4/2007 |
| WO | 2007049155 | 5/2007 |
| WO | 2007107304 | 9/2007 |
| WO | 2007146024 | 12/2007 |
| WO | 2007149518 | 12/2007 |
| WO | 2008020330 | 2/2008 |
| WO | 2008033966 | 3/2008 |
| WO | 2008051245 | 5/2008 |
| WO | 2008083949 | 7/2008 |
| WO | 2008103276 | 8/2008 |
| WO | 2008137758 | 11/2008 |
| WO | 2008148068 | 12/2008 |
| WO | 2008155141 | 12/2008 |
| WO | 2009003975 | 1/2009 |
| WO | 2009016515 | 2/2009 |
| WO | 2009026328 | 2/2009 |
| WO | 2009031043 | 3/2009 |
| WO | 2009040443 | 4/2009 |
| WO | 2009042794 | 4/2009 |
| WO | 2009068485 | 6/2009 |
| WO | 2009074861 | 6/2009 |
| WO | 2009079185 | 6/2009 |
| WO | 2009086558 | 7/2009 |
| WO | 2009104092 | 8/2009 |
| WO | 2009109860 | 9/2009 |
| WO | 2009111088 | 9/2009 |
| WO | 2009127230 | 10/2009 |
| WO | 2009132131 | 10/2009 |
| WO | 2009132206 | 10/2009 |
| WO | 2009146867 | 12/2009 |
| WO | 2009156852 | 12/2009 |
| WO | 2010007463 | 1/2010 |
| WO | 2010007533 | 1/2010 |
| WO | 2010015098 | 2/2010 |
| WO | 2010019718 | 2/2010 |
| WO | 2010036948 | 4/2010 |
| WO | 2010042877 | 4/2010 |
| WO | 2010053572 | 5/2010 |
| WO | 2010054401 | 5/2010 |
| WO | 2010059689 | 5/2010 |
| WO | 2010088537 | 8/2010 |
| WO | 2010119343 | 10/2010 |
| WO | 2010144740 | 12/2010 |
| WO | 2011001780 | 1/2011 |
| WO | 2011005799 | 1/2011 |
| WO | 2011008974 | 1/2011 |
| WO | 2011012316 | 2/2011 |
| WO | 2011068810 | 6/2011 |
| WO | 2011071860 | 6/2011 |
| WO | 2011071931 | 6/2011 |
| WO | 2011075656 | 6/2011 |
| WO | 2011076807 | 6/2011 |
| WO | 2011112717 | 9/2011 |
| WO | 2011127316 | 10/2011 |
| WO | 2011140627 | 11/2011 |
| WO | 2012006369 | 1/2012 |
| WO | 2012006372 | 1/2012 |
| WO | 2012006376 | 1/2012 |
| WO | 2012006377 | 1/2012 |
| WO | 2012006378 | 1/2012 |
| WO | 2012006380 | 1/2012 |
| WO | 2012019168 | 2/2012 |
| WO | 2012030901 | 3/2012 |
| WO | 2012031043 | 3/2012 |
| WO | 2012031046 | 3/2012 |
| WO | 2012034025 | 3/2012 |
| WO | 2012045075 | 4/2012 |
| WO | 2012045082 | 4/2012 |
| WO | 2012135805 | 10/2012 |
| WO | 2012158736 | 11/2012 |
| WO | 2012170889 | 12/2012 |
| WO | 2013006825 | 1/2013 |
| WO | 2013006837 | 1/2013 |
| WO | 2013033563 | 3/2013 |
| WO | 2013039861 | 3/2013 |
| WO | 2013052523 | 4/2013 |
| WO | 2013090648 | 6/2013 |
| WO | 2013096709 | 6/2013 |
| WO | 2013130161 | 9/2013 |
| WO | 2013151663 | 10/2013 |
| WO | 2013151664 | 10/2013 |
| WO | 2013151665 | 10/2013 |
| WO | 2013151666 | 10/2013 |
| WO | 2013151667 | 10/2013 |
| WO | 2013151668 | 10/2013 |
| WO | 2013151669 | 10/2013 |
| WO | 2013151670 | 10/2013 |

(56) References Cited

FOREIGN PATENT DOCUMENTS

| WO | 2013151671 | 10/2013 |
|---|---|---|
| WO | 2013151672 | 10/2013 |
| WO | 2013151736 | 10/2013 |
| WO | 2014081507 | 5/2014 |
| WO | 2014152211 | 9/2014 |
| WO | 2014160243 | 10/2014 |
| WO | 2017049245 | 3/2017 |
| WO | 2017075531 | 5/2017 |
| WO | 2018089790 | 5/2018 |
| WO | 2020106946 | 5/2020 |
| WO | 2021038508 | 3/2021 |
| WO | 2022137133 | 6/2022 |

OTHER PUBLICATIONS

Yu et al., "Effects of Moisture Content on the Storage Stability of Dried Lipoplex Formulations," Journal of Pharmaceutical Sciences 98(9): 3278-3289; 2009.

Zhang, et al., "Ionization Behavior of Amino Lipids for siRNA Delivery: Determination of Ionization Constants, SAR, and the Impact of Lipid pKa on Cationic Lipid-Biomembrane Interactions." Languir: The ACS Journal of Surfaces and Colloids, ACS;2011; pp. 1907-1914; vol. 15(5).

Zhao, QQ., et al., N/P ratio significantly influences the transfection efficiency and cytotoxicity of a polyethylenimine/chitosan/DNA complex, Biol. Pharm. Bull., 2009, 32(4):706-10.

Zhou, et al. "RNA Melanoma Vaccine: Induction of Antitumor Immunity by Human Glycoprotein 100 mRNA Immunization." Human Gene Therapy; 1999; pp. 2719-2724; vol. 10(16).

Zhou, X., et al., "Self-replicating Semliki Forest virus RNA as recombinant vaccine", Vaccine 12(16): 1510-1514 (1994).

Zhu et al. "Vaccines for Gonorrhea: Can We Rise to the Challenge?" Frontiers in Microbiology, vol. 2, Jan. 1, 2011, 13 pages.

Zhu et al., "Systemic Gene Expression after Intravenous DNA Delivery into Adult Mice," Science, 261: 209-211 (1993).

Zhu L & Mahato RI, "Lipid and Polymeric Carrier-Mediated Nucleic Acid Delivery," Expert Opin Drug Deliv. 7(10): 1209-1226, 2010.

Zimmer et al., "RNA Replicons—A New Approach for Influenza Virus Immunoprophylaxis," Viruses, vol. 2, (2010), pp. 413-434.

Zimmermann et al., "RNAi-mediated gene silencing in non-human primates," Nature, vol. 441, pp. 111-114 (2006).

Zuckerman, "Vaccine-Preventable Disease," Principles and Practice of Travel Medicine, Chapter 11, 2001, pp. 165-183.

Zuckerman, The importance of injecting vaccines into muscle, BMJ, vol. 321, pp. 1237-1238 (2000).

Zust et al., (2011) Feb. 2011 "Ribose 2'-O-Methylation Provides a Molecular Signature for the Distinction of Self and Non-self mRNA Dependent on the RNA Sensor Mda5," Nature Immunology, vol. 12, No. 2, pp. 137-144.

Office Action, dated Nov. 23, 2022, in U.S. Appl. No. 17/560,019.

Office Action, dated Nov. 23, 2022, in U.S. Appl. No. 17/560,052.

McGown, "UV Absorbance Measurements of DNA in Microplates," BioTechniques, vol. 28, (2000), pp. 60-64.

Office Action, dated Nov. 25, 2022, in U.S. Appl. No. 17/560,059.

Office Action, dated Dec. 8, 2022, in U.S. Appl. No. 17/560,116.

Felgner et al., "Cationic Lipid-Mediated Transfection in Mammalian Cells: Lipofection," J Tiss Cult Meth., vol. 15, (1993), pp. 63-38.

Akinc et al., "The Onpattro Story and the Clinical Translation of Nanomedicines Containing Nucleic Acid-Based Drugs," Nature Nanotechnology, vol. 14, (2019), pp. 1084-1087.

Ambegia et al., "Stabilized Plasmid-Lipid Particles Containing PEG-diacylglycerols Exhibit Extended Circulation Lifetimes and Tumor Selective Gene Expression," Biochimica et Piophysica Acta., vol. 1669, (2005), pp. 155-163.

Banerjee, "5'Terminal Cap Structure in Eucaryotic Messenger Ribonucleic Acids," Microbiological Reviews, vol. 44, No. 2, (1980), pp. 175-205.

Declaration of Kimberly J. Hassett, dated Nov. 18, 2021.

Cox et al., "Plasmid DNA and Messenger RNA for Therapy," Handbook of Pharmaceutical Biotechnology, Chapter 7.2, (2007), pp. 971-1011.

Bangs et al., "Mass Spectrometry of mRNA Cap 4 from Trypanosomatids Reveals Two Novel Nucleosides, The Journal of Biological Chemistry," vol. 267, No. 14, (1992), pp. 9805-9815.

Excerpt from Moderna's 2018 10-K.

Pascolo, "Vaccination with Messenger RNA (mRNA)," Handboook of Experimental Pharmacology, vol. 183, (2008), pp. 221-235.

Furuichi et al., "Viral and Cellular mRNA Capping: Past and Prospects," Advances in Virus Research, vol. 55, (2000), pp. 135-184.

Fechter et al., "Recognition of mRNA Cap Structures by Viral and Cellular Proteins," Journal fo General Virology, vol. 86, (2005), pp. 1239-1249.

Pardi et al., "Nucleoside-Modified mRNA Vaccines Induce Potent T Follicular Helper and Germinal Center B Cell Responses," Journal of Experimental Medicine, vol. 215, No. 6, (2018), pp. 1571-1588.

Morais et al., "The Critical Contribution of Pseudouridine to mRNA COVID-19 Vaccines," Frontiers in Cell and Development Biology, vol. 9, (2021), pp. 1-9.

Hess et al., "Vaccination with mRNAs encoding Tumor-Associated Antigens and Granulocyte-Macrophage Colony-Stimulating Factor Efficiently Primes CTL Responses, but is Insufficient to Overcome Tolerance to a Model Tumor/Selt Antigen,," Cancer Immunol Immunother, vol. 55, (2006), pp. 672-683.

Lambert et al., "Intradermal Vaccine Delivery: Will New Delivery Systems Transform Vaccine Administration?" Vaccine, vol. 26, (2008), pp. 3197-3208.

Li et al., Low-pH-Sensitive Poly(ethylene glycol) (PEG)-Stabilized Plasmid Nanolipoparticles: Effects of PEG Chain Length, Lipid Composition and Assembly Conditions on Gene Delivery, The Journal of Gene Medicine, vol. 7, (2005), pp. 67-79.

Patentee Submission to EPO in EP Application No. 11758014.2, dated Nov. 13, 2018.

Roos, "Europe Approves Sanofi's Intradermal Flu Vaccine," University of Minnesota Center for Infections Disease Research and Policy [online: cidrap.umn.edu/news-perspective/2009/02/europe-approves-sanofis-intradermal-flu-vaccine], (2009), pp. 1-2.

"ProductInfoNow," Modern Drug Discovery, vol. 6, No. 6, (2003), pp. 57-62.

Print-out of the entry for the m7G(5')ppp(5')G RNA Cap Structure Analog from the New England Biolabs homepage, from Apr. 2010, pp. 1-2.

Print-out of the entry for the ScriptCap™ m7G Capping System from the Epicentre Biotechnologies homepage from Nov. 2006, pp. 1-2.

Santos et al., "Design of Peptide-Targeted Liposomes Containing Nucleic Acids," Biochimica et Biophysica Acta, vol. 1798, (2010), pp. 433-441.

Spikevax Patient Information, European Medicines Agency, (2022), pp. 1-5.

Sticchi et al., "The Intradermal Vaccination: Past Experiences and Current Perspectives," J Prev Med Hyg, vol. 51, (2010), pp. 7-14.

Van den Berg et al., "Shielding the Cationic Charge of Nanoparticle-Formulated Dermal DNA Vaccines is Essential for Antigen Expression and Immunogenicity," Journal of Controlled Release, vol. 141, (2010), pp. 234-240.

Sonoke et al., "Tumor Regression in Mice by Delivery of Liposomes," Cancer Research, vol. 68, (2008), pp. 8843-8851.

Kim et al., "Enhanced siRNA Delivery using Cationic Liposomes with new Polyarginine-Conjugated PEG-Lipid," International Journal of Pharmaceutics, vol. 392, (2010), pp. 141-147.

Office Action, dated Dec. 21, 2022, issued in U.S. Appl. No. 16/656,929.

U.S. Appl. No. 18/333,591, filed Jun. 13, 2023.

U.S. Appl. No. 18/231,693, filed Aug. 8, 2023.

U.S. Appl. No. 18/231,692, filed Aug. 8, 2023.

U.S. Appl. No. 18/231,697, filed Aug. 8, 2023.

Lundstrom, "Semliki Forest Virus Vectors for Gene Therapy," Expert Opinion on Biological Therapy, vol. 3, No. 5, (2003), pp. 771-777.

(56) References Cited

OTHER PUBLICATIONS

Lv et al., "Toxicity of cationic lipids and cationic polymers in gene delivery." Journal of Controlled Release, vol. 114 (2006), pp. 100-109. (Year: 2006).
Lyubchenko, et al., "Visualization of supercoiled DNA with atomic force microscopy in situ" Proc. Natl. Acad Sci. USA; 1997; pp. 496-501; vol. 94.
Macagno et al., "Isolation of Human Monoclonal Antibodies That Potently Neutralize Human Cytomegalovirus Infection by Targeting Different Epitopes on the gH/gL/UL128-131A Complex", 2010 Journal of Virology 84 (2):1005-1013.
MacLachlan, I., "Liposomal formulations for nucleic acid delivery", Antisense Drug Technologies, 2nd Edition, Chapter 9, 237-270, 2007.
Mahato RI, Water insoluble and soluble lipids for gene delivery, Adv. Drug Delivery Rev.,2005, 57(5):699-712.
Malone et al., "Cationic liposome-mediated RNA transfection", Proc. Natl. Acad. Sci. (PNAS) USA: Biochemistry; 86:16; 6077-6081; 1989.
Mandal et al., "Delivery of Macromolecules into Cytosol using Liposomes Containing Hemolysin," Methods in Enzymology, vol. 372, (2003), pp. 319-339.
Mann et al., "DNA Transfer into Vascular Smooth Muscle using Fusigenic Sendai Virus (HJV)-Liposomes," Molecular and Cellular Biochemistry, vol. 172, (1997), pp. 3-12.
Manning, et al., "Infectivity of Liposomally Encapsulated Nucleic Acids Isolated From EMC Virus and Scrapie-Infected Mouse Brain," Intervirology; vol. 20; 1983; pp. 164-168.
Martin, et al., "Characterization of formaldehyde-inactivated poliovirus preparations made from live-attenuated strains." Journal of General Virology; 2003; pp. 1781-1788; vol. 84.
Martinon et al. "Induction of virus-specific cytotoxic T lymphocytes in vivo by liposome-entrapped mRNA," Eur. J. Immuno. 1993.23: 1719-1722.
Matsuura, et al., "Polycation liposome-mediated gene transfer in vivo," Biochimica et Biophysica Acta, vol. 1612, 2003, pp. 136-143.
Maurer, et al., "Spontaneous Entrapment of Polynucleotides upon Electrostatic Interaction with Ethanol-Destabilized Cationic Liposomes" Biophys Journal; vol. 80; 2001; pp. 2310-2326.
McGlone, et al., "Pig Production: Biological Principles and Applications" Chapter 8; 2000; pp. 99.
Merriam-Webster definition of "virion" (downloaded Mar. 14, 2016).
Mocarski et al., "Cytomegalovirus and their replication," In Fields Virology, 4th edition, vol. 2, 2001, DM Knipe and PM Howley (ed.), Lippincott Williams and Wilkins, Philadelphia, PA, pp. 2629-2673.
Mockey, et al., "mRNA-based cancer vaccine: prevention of B16 melanoma progression and metastasis by systemic injection of MART1 mRNA histidylated lipopolyplexes." Cancer Gene Therapy; 2007; pp. 802-814; vol. 14(9).
Mok et al., "Venezuelan equine encephalitis virus replicon particles encoding respiratory syncytial virus surface glycoproteins induce protective mucosal responses in mice and cotton rats," Journal of Virology, The American Society for Microbiology, 81(24):13710-13722 (2007).
Molina et al.: The stability of lyophilized lipid/DNA complexes during prolonged storage, Journal of Pharmaceutical Sciences, vol. 93, No. 9, Sep. 2004.
Monslow MA, Elbashir S, Sullivan NL, Thiriot DS, Ahl P, Smith J, et. al. "Immunogenicity generated by mRNA vaccine encoding VZV gE antigen is comparable to adjuvanted subunit vaccine and better than live attenuated vaccine in nonhuman primates," Vaccine. Aug. 10, 2020;38(36):5793-5802. Epub Jul. 20, 2020. (Year: 2020).
Montana et al. "Employment of Cationic Solid-Lipid Nanoparticles as RNA Carriers," Bioconjugate Chem. 2007, 18, 302-308.
Morris-Downes, et al., "A recombinant Semliki Forest virus particle vaccine encoding the prME and NS1 proteins of louping ill virus is effective in a sheep challenge model." Vaccine; 2001; pp. 3877-3884; vol. 19.

Mosca et al., "Molecular and cellular signatures of human vaccine adjuvants," Proc. Natl. Acad. Sci. USA, 105:10501-10506 (2008).
Mossman, "Protection against Lethal Simian Immunodeficiency Virus SIVsmmPBj14 Disease by a Recombinant Semliki Forest Virus gp160 Vaccines and by a gp120 Subunit Vaccine." J. Virology; 1996; pp. 1953-1960; vol. 70.
Motorin & Helm (2009) Dec. 8, 2009 "RNA Nucleotide Methylation," Advanced Review, vol. 2, pp. 611-631.
Motorin & Helm (2011) Sep./Oct. 2011 "5-Methylcytosine in RNA: Detection, Enzymatic Formation and Biological Functions," Nucleic Acids Research, vol. 38, No. 5, pp. 1415-1430.
MRNA-Only™ Prokaryotic mRNA Poly(A)-Tailing.
Murphy et al., "Coding potential of laboratory and clinical strains of cytomegalovirus," Proc. Natl. Acad. Sci. USA, 2003, 100(25):14976-14981.
Na Slund et al."Role of innate signalling pathways in the immunogenicity of alphaviral replicon-based vaccines," Virology Journal, 8(1):36 (2011).
Narang, et al., "Cationic Lipids with Increased DNA Binding Affinity for Nonviral Gene Transfer in Dividing and Nondividing Cells," Bioconjugate Chem. 16 (2005), 156-166.
NCBI reference sequence. "*Homo sapiens* coagulation factor VIII (F8), transcript variant 1, mRNA." Mar. 2016, pp. 1-18.
Notice of Opposition in relation to European Patent No. 2591103B1 (Appln No. 11736498.4) dated May 28, 2020 (44 pages).
Notice of Opposition in relation to European Patent No. 2591103B1 (Appln No. 11736498.4) dated May 27, 2020 (17 pages).
Nucleic Acids in Innate Immunity, Various Authors (2008) CRC Press.
Obata, "Evaluation of pH-responsive liposomes containing amino acid-based zwitterionic lipids for improving intracellular drug delivery in vitro and in vivo", Journal of Controlled Release; 2010; pp. 267-276; vol. 142, No. 2.
O'Hagan et al., "Induction of potent immune responses by cationic microparticles with adsorbed human immunodeficiency virus DNA vaccines," J Virology, (2001), vol. 75, pp. 9037-9043.
Operating manual freeze-dryer Alpha 1-4 LCS plus and Alpha 2-4 LSC plus by Christ, revised version of Dec. 16, 2013.
Opponents arguments by Dr. Georg Schnappauf filed on Jan. 14, 2022, in opposition to European Patent No. 2591103.
Opponents arguments by Janssen Vaccines & Prevention B.V. filed on Jan. 14, 2022 in opposition to European Patent No. 2591103.
Opposition Document D60—Declaration of Russell N. Johnson, dated Aug. 6, 2018, from EP2591114, European Equivalent of U.S. Appl. No. 13/808,153, filed Aug. 8, 2018.
Organism overview of Encephalomyocarditis virus and of Poliovirus obtained from PubMed "Encephalomyocarditis virus." retrieved on Jun. 4, 2019 from https://www.ncbi.nlm.mih.gov/genome/?term=encephalomyocarditis+virus, and "Enterovirus C" retrieved on Jun. 4, 2019 from https://www.ncbi.nlm.nih.gov/genome/?term=poliovirus[orgn].
Ott, et al., "A Cationic sub-micron emulsion [lv159/DOTAP] is an effective delivery system for DNA vaccines," Journal of Controlled Release; 2002; pp. 1-5; vol. 79(1-3).
Oussoren, et al., "Lymphatic Uptake and Biodistribution of Liposomes After Subcutaneous Injection: III. Influence of Surface Modification with Poly(ethyleneglycol)." Pharmaceutical Research, 1997, vol. 14, No. 10, pp. 1479-1484.
Pang et al., (1982) Apr. 1982 "Structure of a Modified Nucleoside in Archaebacterial tRNA which Replaces Ribosylthymine," The Journal of Biological Chemistry, vol. 257, No. 7, pp. 3589-3592.
Papahadjopoulos, et al., "Cochleate Lipid Cylinders: Formation by Fusion of Unilamellar Lipid Vesicles" Biochim et Biophys Acta; 1975; pp. 483-491; vol. 394.
Papahadjopoulos, et al., "Incorporation of Macromolecules within Large Unilamellar Vesicles (LUV)" Annals NY Academy of Sciences; 1978; pp. 259-267.
Parent application PCT/US2012/041663 in the form as published as WO 2012/170889 A1.
Pascolo S., "Messenger RNA-based vaccines", Expert Opinion on Biological the, Informa Healthcare, Ashley, London; GB, vol. 4, No. 8, Aug. 1, 2004 (Aug. 1, 2004), pp. 1285-1294.

(56) References Cited

OTHER PUBLICATIONS

Pascolo, "Vaccination With Messenger RNA." Methods in Molecular Medicine, 2006, vol. 127, pp. 23-40.
Declaration by Russell Johnson cited in EP2729126 on Jul. 4, 2018 and in opposition filed on Sep. 23, 2021 (4 pages).
Declaration by Russell Johnson dated Sep. 21, 2022 in opposition filed in EP2591103, Int'l filing date Jul. 6, 2012, (2 pages).
Declaration entitled "Annex A" by Russell Johnson cited in EP2729126 in opposition filed on Sep. 23, 2021 (4 pages).
Declaration from Dr Olatokumbo Ogunleye.
Declaration of Prof. Liljestrom submitted to the European Patent Office in the opposition proceedings concerning EP2590676 B1.
Declaration of Professor Liljestrom dated Dec. 11, 2018 submitted in EP2590676, itself having annexes A-G.
Declaration of Russell N. Johnson dated Dec. 10, 2018.
Deering, et al., "Nucleic acid vaccines: prospects for non-viral delivery of mRNA vaccines." Expert Opinion Drug Delivery; 2014; pp. 885-899; vol. 11(6).
Defang et al., "Induction of neutralizing antibodies to Hendra and Nipah glycoproteins using a Venezuelan equine encephalitis virus in vivo expression system," Vaccine Elsevier Ltd. GB,29(2):212-220 (2010).
Depledge DP, Yamanishi K, Gomi Y, Gershon AA, Breuer J. "Deep Sequencing of Distinct Preparations of the Live Attenuated Varicella-Zoster Virus Vaccine Reveals a Conserved Core of Attenuating Single-Nucleotide Polymorphisms," J Viral. Sep. 12, 2016;90 (19):8698-704. (Year: 2016).
Diebold, S.S., et al., "Innate Antiviral Responses by Means of TLR7-Mediated Recognition of Single-Stranded RNA", Science 303(5663): 1529-1531 (2004).
Dolan et al, "Genetic Content of Wild-Type Human Cytomegalovirus", J. Gen. Virol. May 2004; 85(Pt 5):1301-12.
Drug Discovery Handbook, edited by Shayne Cox Gad, Wiley Interscience, 2005; Chapter 27: RNA-based therapies, pp. 1259 to 1308.
Dunn et al., "Functional profiling of a human cytomegalovirus genome," Proc. Natl. Acad. Sci. USA, 2003, 100 (24):14223-14228.
Dupuis et al., "Dendritic cells internalize vaccine adjuvant after intramuscular injection", Cellular Immunology, 186:18-27 (1998).
Dupuis et al., "Distribution of DNA vaccines determines their immunogenicity after intramuscular injection in mice," Journal of Immunology, 165:2850-2858 (2000).
Durbin AF, Wang C, Marcotrigiano J, Gehrke L. "RNAs Containing Modified Nucleotides Fail To Trigger RIG-I Conformational Changes for Innate Immune Signaling," mBio. Sep. 20, 2016;7(5):e00833-16. doi: 10.1128/mBio.00833-16. PMID: 27651356; PMCID: PMC5030355. (Year: 2016).
Dwarki et al., "Cationic Liposome-Mediated RNA Transfection," Methods in Enzymology, vol. 217, (1993), pp. 644-654.
Earl and Townsend (1977) Jun. 1977 "A Chemical Synthesis of the Nucleoside I-Methylpseudouridine," J. Heterocyclic Chem, vol. 15, pp. 699-700.
Eastman et al., "Influence of Phospholipid Asymmetry on Fusion between Large Unilamellar Vesicles," Biochemistry, vol. 31, (1992), pp. 4262-4268.
Eberhardt et al. "Modulation of mRNA Stability as a Novel Therapeutic Approach," Pharmacology & Therapeutics 114 (2007) 56-73.
El Ouahabi, A. et al., "Double long-chain amidine liposome-mediated self replicating RNA transfection", FEBS Letters, 380(1-2): 108-112 (1996).
Elbashir et al., "Duplexes of 21-nucleotide RNAs mediate RNA interference in cultured mammalian cells." Nature, 2001, 411(6836), 494-498.
Elkington et al., "Ex Vivo Profiling of CD8+-T-Cell Responses to Human Cytomegalovirus Reveals Broad and Multispecific Reactivities in Healthy Virus Carriers," Journal of Virology (2003), vol. 77, No. 9, pp. 5226-5240.
Elliott et al., "Alphavirus replicon particles encoding the fusion or attachment glycoproteins of respiratory syncytial virus elicit protective immune responses in BALB/c mice and functional serum antibodies in rhesus macaques," Vaccine Elsevier LTD, GB, 25(41):7132-7144, (2007).
Encyclopedia Britannica House Mouse; 2005, p. 963.
EP12722942.5 (Moderna's submission of Jul. 9, 2018).
EP12738679.5 Third Party Observations in accordance with Article 115 EPC; Mar. 8, 2019.
ER, et al., "The encapsulation and release of guanosine from PEGylated liposomes." Journal of Liposome Research, 2009, vol. 19, No. 1, pp. 29-36.
Ernsting MJ, Murakami M, Roy A, Li SD. "Factors controlling the pharmacokinetics, biodistribution and intratumoral penetration of nanoparticles," J Control Release. Dec. 28, 2013;172(3):782-94. doi: 10.1016/j.jconrel.2013.09.013. Epub Sep. 25, 2013. PMID: 24075927; PMCID: PMC3891171. (Year: 2013).
Espuelas, Socorro, et al., "Effect of synthetic lipopeptides formulated in liposomes on the maturation of human dendritic cells," Molecular Immunology 42 (2005): 721-729, and Corrigendum, Molecular Immunology 43 (2006) 772.
Evers, M., et al, "State-of-the-Art Design and Rapid-Mixing Production Techniques of Lipid Nanoparticles for Nucleic Acid Delivery", Small Methods, 2:1-20, (2018).
Excerpt from "Chemical Book" on DLinDMA Sep. 9, 2021.
Excerpt from "Comprehensive Supermolecular Chemistry II" 2017; vol. 1.
Excerpt from PubChem: Transfectam.
Excerpt of textbook "The immune system" by Peter Parham, Third edition, (2009) Cover page, Table contents and pp. 49 and 50 common general knowledge.
Expert opinion Prof. Schubert.
F.F. Davis, F.W. Allen (1957) "Ribonucleic Acids from Yeast which Contain a Fifth Nucleotide".
Faneca, H et al., Drug Delivery Systems: Advanced Technologies Potentially Applicable in Personalised Treatment, Advances in Predictive, Preventive and Personalised Medicine 4:153-184, 2013.
Faure, et al., "Control of the in vivo Biodistribution of Hybrid Nanoparticles with Different Poly(ethylene glycol) Coatings." Small, 2009, vol. 5, No. 22, pp. 2565-2575.
Felgner, et al., "Lipofection: A Highly Efficient, Lipid-Mediated DNA-Transfection Procedure." Proc. Natl. Acad. Sci. USA; 1987pp. 7413-7417; vol. 84.
Fenske, "Liposomal Nanomedicines: An Emerging Field", Toxicologic Pathology; 2008; pp. 21-29; vol. 36, No. 1.
Final Decision and Upheld Claims from EP2591114, European Equivalent of U.S. Appl. No. 13/808,153, dated Nov. 27, 2018.
Fleeton et al., "Self-Replicative RNA Vaccines Elicit Protection against Influenza A Virus, Respiratory Syncytial Virus, and a Tickborne Encephalitis Virus", Journal of Infectious Diseases 183:1395-1398 (2001).
Fraenkel-Conrat et al., (Ed.), Virology second edition, Prentice-Hall Inc., Englewood Cliffs, New Jersey; 1988; from Chapter 3, "Enveloped Plus-strand RNA Viruses:Togaviridae", pp. 96-103.
Fraenkel-Conrat, "Togaviridae", Virology second edition, Prentice-Hall Inc.; 1988; p. 2 pp. 99.
Freddolino, et al, "Molecular Dynamics Simulations of the Complete Satellite Tobacco Mosaic Virus." Structure; 2006; pp. 437-449; vol. 14.
Freer G, Pistello M. "Varicella-zoster virus infection: natural history, clinical manifestations, immunity and current and future vaccination strategies," New Microbial. Apr. 2018;41(2):95-105. Epub Mar. 2, 2018. PMID: 29498740; 2018.
Frolov et al., "Alphavirus-based expression vectors: Strategies and applications," 93 Proceedings of the National Academy of Sciences USA (1996).
Fynan, E.F., et al., DNA vaccines: Protective immunizations by parenteral, mucosal, and gene-gun inoculations; Proc Natl Acad Sci.; 1993; pp. 11478-11482; vol. 90.
Wisse et al. "The Size of Endothelial Fenestrae in Human Liver Sinusoids: Implications for Hepatocyte-Directed Gene Transfer," Gene Therapy, 2008, vol. 15, pp. 1193-1199.
Declaration and Curriculum Vitae of Dr. Olatokumbo Ogunleye dated Mar. 1, 2022 and filed in European Patent Application Publication No. EP 3336082.

(56) References Cited

OTHER PUBLICATIONS

Patel et al., "The Importance of Apparent pKa in the Development of Nanoparticles Encapsulating siRNA and MRNA," Trends Pharmacol Sci., vol. 42, No. 6, (2021), pp. 448-460.
Patentee's Reply to Opposition in relation to European Patent No. 2591103B1 (Appln No. 11736498.4) dated Oct. 23, 2020 (28 pages).
Peng et al., "The gH-gL complex of herpes simplex virus (HSV) stimulates neutralizing antibody and protects mice against HSV type 1 challenge," J. Virol., 1998, 72(1):65-72.
Perri, S., et al., "An Alphavirus Replicon Particle Chimera Derived from Venezuelan Equine Encephalitis and Sindbis Viruses is a Potent Gene-Based Vaccine Delivery Vector." J. Virol.; 2003; pp. 10394-10403; vol. 77 (19).
Phumiamorn, et al., "Induction of humoral and cell-mediated immunity to hepatitis B surface antigen by a novel adjuvant activity of Oka varicella vaccine." Journal of General Virology; 2003; pp. 287-291; vol. 84.
Pomeroy et al., "Cyotmegalovirus: epidemiology and infection control," Am. J. Infect. Control, 1987, 15(3):107-119.
Post-filed evidence submitted on Jun. 12, 2014 during prosecution of EP2578685 B1 (D1a).
Post-filing experimental evidence submitted by the Patentee during the examination phase of EP 18 153 312.6 on Apr. 5, 2019.
Poveda C, Biter AB, Bottazzi ME, Strych U. "Establishing Preferred Product Characterization for the Evaluation of RNA Vaccine Antigens," Vaccines (Basel). Sep. 27, 2019;7(4):131. doi: 10.3390/vaccines7040131. PMID: 31569760; PMCID: PMC6963847. (Year: 2019).
Preliminary Opposition Opinion from EP2591114 (EP Appl. 11736497.6), European Equivalent of U.S. Appl. No. 13/808,153, dated Feb. 23, 2018.
Pschyrembel, Klinisches Wortenbuch Immunisiserung, Immunreaktion; 1997; pp. 747-748.
Pushko, P. et al., "Replicon-Helper Systems from Attenuated Venezuelan Equine Encephalitis Virus: Expression of Heterologous Genes in Vitro an dimmunization against Heterologous Pathogens in Vivo," Virology, 239: 389-401(1997).
Qa'Dan et al., "ph-Induced Conformational Changes in Clostridium Difficile Toxin B," Infect & Immun., vol. 68, (2000), pp. 2470-2474.
Ramana, et al, "Development of a liposomal nanodelivery system for nevirapine." Journal of Biomedical Science, 2010, 17:57, pp. 1-9.
Rayner, et al., "Alphavirus vectors and vaccination", Reviews in Medical Virology; 2002; pp. 279-296; vol. 12.
Reap et al., Development and preclinical evaluation of an alphavirus replicon particle vaccine for cytomegalovirus, Vaccine, Elsevier LTD, GB, 25(42):7441-7449, (2007).
Reap et al., "Cellular and humoral immune responses to alphavirus replicon vaccines expressing cytomegalovirus pp65, IE1 and gB proteins," Clin. Vacc. Immunol., 2007, 14(6):748-755.
Reichman et al., (1977) Feb. 1977 The Journal of Antibiotics, vol. XXX, No. 2, pp. 129-131.
Reijenga et al., "Development of Methods for the Determination of pKa Values," Analytical Chemistry Insights, vol. 8, (2013), pp. 53-71.
Ren et al., "Immunogene therapy of recurrent glioblastoma multiforme with a liposomally encapsulated replication-incompetent Semliki forest virus vector carrying the human interleukin-12 gene—a phase 1/11 clinical protocol", J. Neuro-Oncology, 2003, 64:147-154.
Rishi R Goel, et al., "Distinct antibody and memory B cell responses in SARS-COV-2 naïve and recovered individuals after mRNA vaccination," Science Immunology, vol. 6, eabi6950, Apr. 2021, pp. 1-13; 2021.
Robbins et al., (2007) Sep. 1, 2007 "2'-O-Methyl-Modified RNAs Act as TLR7 Antagonists," Mol. Ther. vol. 15, No. 9, pp. 1663-1669.
Rodrigueza, et al. "Development and Antitumor Activity of a BCL-2 Targeted Single-Stranded DNA Oligonucleotide," Cancer Chemother Pharmacol 74:151-166, 2014.

Rodriguez-Gascon et al., Development of nucleic acid vaccines: use of self-amplifying RNA in lipid nanoparticles, International Journal of Nanomedicine, 2014, vol. 9(1), 1833-1843.
Roldao A Mellado MC Castilho LR Carrondo MJ Alves PM. Virlike particles in vaccine development. Expert Rev Vaccines. Oct. 2010;9(10):1149-76.
Rubin, "Clinical approach to infection in the compromised host," In Infection in the Organ Transplant Recipient, 4th edition, R Rubin and LS Young (ed.), Kluwer Academic Press, New York, NY, 2002, pp. 573-679.
Russell Johnson Declaration.
Ryckman et al., "Characterization of the human cytomegalovirus gH/gL/UL128-131 complex that mediates entry into epithelial and endothelial cells," J. Virol., 2008, 82(1):60-70.
Ryckman et al., "Human cytomegalovirus TR strain glycoprotein O acts as a chaperone promoting gH/gL incorporation into virions, but is not present in virions," J. Virol., 2010, 84(5):2597-2609.
Sacco, et al, "The Average Body Surface Area of Adult Cancer Patients in the UK: A Multicentre Retrospective Study." PLoS ONE; 2010; pp. 1-6; vol. 5(1).
Saccoccio, Frances Maria, "Thesis: CMV Vaccine Development based on Epithelial Entry Mediators UL128, UL130, and UL131," Jun. 3, 2011, Retrieved from the Internet: URL: https//digarchiveJibrary.vcu.edu/bitstreamjhandle/10156/3452/SACCOCCIO FRANCES PhD.pdf?sequence=1-1 retrieved on Mar. 18, 2014] Impact on future vaccine design; p. 160 (2011). Chapter: Peptides to UL130 and UL131. Neutralize CMV Infection of Mucosal Epithelial Cells; p. 96.
Sadzuka et al., "Effect of Polyethyleneglycol (PEG) Chain on Cell Uptake of PEG-Modified Liposomes," J. Liposome Res., 13(2), 157-172 (2003).
Saeki, Y., et al., "Development and Characterization of Cationic Liposomes Conjugated with HVJ (Sendai Virus): reciprocal Effect of Cationic Lipid For In Vitro and In Vivo Gene Transfer", Human gene Therapy, 8(17): 2133-2141 (1997).
Saenz-Badillos, et. al., "RNA as a tumor vaccine: a review of the literature", Experimental Dermatology; 2001; pp. 143-154; vol. 10, Issue 3.
Sahin et al., Nature Reviews Drug Discovery (2014), 13, 759-780, published online on Sep. 19, 2014.
Samad et al (2007). Liposomal drug delivery systems: an updated review. Curr Drug Deliv. Oct. 2007;4(4):297-305.
Sawai et al., "A Novel Method of Cell-Specific mRNA Transfection" 64 Molecular Genetics and Metabolism 44-51 (1998).
Saxena et al., "Induction of immune responses and protection in mice against rabies using a self-replicating RNA vaccine encoding rabies virus glycoprotein," Veterinary Microbiology; vol. 136(1-2); 2009; pp. 36-44.
Schedin-Weiss et al., "Antiangiogenic Forms of Antithrombin Specifically Bind to the Anticoagulant Heparin Sequence," Biochemistry, vol. 47, (2008), pp. 13610-13619.
Scheel, et al., "Toll-like receptor-dependent activation of several human blood cell types by protamine-condensed (TRNA"; European Journal of Immunology; 2005; pp. 1557-1566.
Schirrmacher et al., "Intra-pinna anti-tumor vaccination with self-replicating infectious RNA or with DNA encoding a model tumor antigen and a cytokine" Gene Therapy; 2000; pp. 1137-1146; vol. 7.
Schlake et al., "Developing mRNA-Vaccine Technologies," RNA Biology (2012), 9 (11), 1319-1330, published in Nov. 2012.
Schleiss MR. Cytomegalovirus vaccine development. Curr Top Microbiol Immunol. 2008;325:361-82.
Schlesinger et al., "Alphavirus vectors for gene expression and vaccines," Current Opinion in Biotechnology, 1999, 10:434-439.
Schoenmaker, et al., mRNA-lipid nanoparticle COVID-19 vaccines: Structure and stability, International Journal of Pharmaceutics 601; 120586, pp. 1-13; 2021.
Search Report issued in EP Application No. 21298987.3, dated May 25, 2022.
Semple et al. Efficient encapsulation of antisense oligonucleotides in lipid vesicles using ionizable aminolipids: formation of novel small multilamellar vesicle structures. Biochimica et Biophysica Acta (BBA)—Biomembranes, vol. 1510, 2001, pp. 152-166.

(56) References Cited

OTHER PUBLICATIONS

Semple et al., "Rational design of cationic lipids for siRNA delivery," Nature Biotechnology, v. 28 :172-176 (2010).
Shade RO Blundell MC Cotmore SF Tattersall P Astell CR. unknown protein [Human parvovirus B19]. GenBank: AAA66867.1 Dep. 05171995.
Shah RA, Limmer AL, Nwannunu CE, Patel RR, Mui UN, Tyring SK. "Shingrix for Herpes Zoster: A Review," Skin Therapy Lett. Jul. 2019;24(4):5-7. PMID: 31339679. (Year: 2019).
Britt et al., "Cytomegalovirus," In Fields Virology, 3rd edition, BN Fields, DM Knipe, PM Howley (ed.), Philadelphia, PA, Lippincott-Raven, 1996, pp. 2493-2523.
Britt et al., "Human cytomegalovirus virion proteins," Hum. Immunol., 2004, 65:395-402.
Broz, et al. "Newly described pattern recognition receptors team up against intracellular pathogents", Nat. Rev. Immunol. 13:8: 551-565 (2013).
Buyens et al., "Elucidating the encapsulation of short interfering RNA in PEGylated cationic liposomes," Langmuir, 25 (9) :4886-4891 (2009).
Buza, J. et al., "CD14+ cells are required for IL-12 response in bovine blood mononuclear cells activated with Toll-like receptor (TLR) 7 and TLR8 ligands", Vet. Immunol. Immunopath. 126(3-4): 273-282 (2008)—XP025676816.
Cannon, G., et al., "RNA Based Vaccines", DNA Cell Biol., 21(12): 953-961 (2002).
Caplen, "Nucleic acid transfer using cationic lipids." Methods in Mol Biol.; 2000; pp. 1-19; vol. 133.
Carine et al., "Vaccination of calves using the BRSV nucleocapsid protein in a DNA prime-protein boost strategy stimulates cell-mediated immunity and protects the lungs against BRSV replication and pathology," Vaccine Elsevier LTD, GB, 26(37):4840-4848 (2008).
Carralot, J.P., et al., "Polarization of immunity induced by direct injection of naked sequence-stabilized mRNA vaccines", Cell. Mole. Life Sci. 61(18): 2418-2424 (2004)—XP002355208.
Cavagna, et al.; "7—Signs and Work of Man"; The National Park of the Casentine Forests; 2003; pp. 175.
Certified U.S. Appl. No. 61/223,347, filed Jul. 6, 2009.
Certified U.S. Appl. No. 61/265,653, filed Dec. 1, 2009.
Certified U.S. Appl. No. 61/361,780, filed Jul. 6, 2010.
Certified U.S. Appl. No. 61/361,794, filed Jul. 6, 2010.
Cha et al., "Human cytomegalovirus clinical isolates carry at least 19 genes not found in laboratory strains," J. Virol., 1996, 70(1):78-83.
Chambers, et al., "Vaccination of mice and cattle with plasmid DNA encoding the *Mycobacterium bovis* antigent MPB83." Clinical Infection Diseases; 2000; pp. S283-S287; vol. 30(3).
Chang et al. 2008 Nov. 19, 2007 "Synthesis and Solution Conformation Studies of 3-substituted Uridine and Pseudouridine Derivatives," Bioorganic & Medicinal Chemistry, vol. 16, pp. 2676-2686.
Chatterjee et al., (2012) Mar. 2012 "The Archaeal COG1901/DUF358 Spout-Methyltransferase Members, Together with Pseudouridine Synthase Pus10, Catalyze the Formation of 1-Methylpseudouridine at Position 54 of tRNA," RNA, vol. 18, pp. 421-433.
Chee et al, "Hypothetical Protein UL128", UniProtKB/Swiss-Prot: P16837, Dep. Feb. 1, 1991.
Chee et al., "Analysis of the protein-coding content of the sequence of human cytomegalovirus strain AD169," Curr. Top. Microbiol. Immunol., 1990, 154:125-169.
Chen et al. "An Overview of Liposome Lyophilization and its Future Potential," Journal of Controlled Release 142 (2010) 299-311.
Chen S, Tam YYC, Lin PJC, Sung MMH, Tam YK, Cullis PR. "Influence of particle size on the in vivo potency of lipid nanoparticle formulations of siRNA," J Control Release. Aug. 10, 2016;235:236-244. doi: 10.1016/j.jconrel.2016.05.059. Epub May 26, 2016. PMID: 27238441. (Year: 2016).
Cheng et al., "Enhancement of Sindbis virus self-replicating RNA vaccine potency by linkage of *Mycobacterium tuberculosis* heat shock protein 70 gene to an antigen gene", Journal of Immunology, 166:6218-6226 (2001).
Cheng WF, Hung CF, Lee CN, Su YN, Chang MC, He L, Wu TC, Chen CA, Hsieh CY. Naked RNA vaccine controls tumors with down-regulated MHC class I expression through NK cells and perforin-dependent pathways. Eur J Immunol. Jul. 2004;34(7):1892-900.
Cheng, W.F., et al, "Enhancement of Sindbis Virus Self-Replicating RNA Vaccine Potency by Linkage of Herpes Simplex Virus Type 1 VP22 Protein to Antigen", J. Viral. 75(5): 2368-2376 (2001)—XP002201711.
Chiaramoni et al "Liposome/DNA systems: correlation between hydrophobicity and DNA conformational changes" Journal of Biological Physics, 34(1-2), 179-88 (2008).
Chrai et al., "Liposomes: A Review Part I: Manufacturing Issues," Biotech Trends, Pharmaceutical Technology, 28-34 (2002).
Christ: "Gefriertrocknung mit System" (with D6a, a timestamp, showing that this document was available as of Jan. 22, 2010).
Christ: "Smart Freeze Drying" Manual Jan. 2010.
Communication of the Board of Appeal in relation to the Opposition of European Patent No. 2590676B1 Appln No. 11741348.4) (12 pages).
Communication of the Board of Appeals pursuant to Art. 15(1) of the Rules of Procedure of the Boards of Appeal dated Mar. 25, 2021, in European Patent Application Publication No. 2590676.
Compton et al., "Receptors and immune sensors: the complex entry path of human cytomegalovirus," Trends Cell. Bio., 2004, 14(1):5-8.
Corresponding parent application: U.S. Appl. No. 16/114,621, filed Aug. 28, 2018.
Cortesi et al.: Effect of DNA complexation and freeze-drying on the physicochemical characteristics of cationic liposomes, Antisense & Nucleic Acid Drug Development 10:205-215(2000).
Cox, et al., "Bovine herpesvirus 1: immune responses in mice and cattle injected with plasmid DNA." Journal of Virology; 1993; pp. 5664-5667; vol. 67(9).
CRC Handbook of Chemistry and Physics, 101st Edition, CRC Press 2020—Section 6 vapor pressure of ice.
Crooke Stanley T., (Ed.), "Antisense Drug Technology: Principles, Strategies, and Applications," 2nd ed., chapter 9 (2008), pp. 237-270.
Cui, et al., DNA Vaccine, Advances in Genetics; 2005; pp. 257-289; vol. 54.
Cullis, Pieter; WO2011140627 certified Priority Document U.S. Appl. No. 61/280,510.
CV Dr Olatokumbo Ogunleye.
D. Liu and L. Huang Journal of Liposome Research 2(1): 57-66 (1992).
Davis, et al., "DNA vaccine for hepatitis B Evidence for immunogenicity in chimpanzees and comparison with other vaccines." Proc. Natl Acad Sci USA; 1996; pp. 7213-7218; vol. 93.
Davison AJ, UL115; gL [Human Herpesvirus 5]. NCBI Reference Sequence: YP_081555.1, Dep. Sep. 16, 2004.
Davison AJ, UL130 [Human Herpesvirus 5]. NCBI Reference Sequence: YP_081565.1, Dep. Sep. 16, 2004.
Davison AJ, UL131A [Human Herpesvirus 5]. NCBI Reference Sequence: YP_081566.1, Dep. Sep. 16, 2004.
Davison AJ, UL75; gH [Human Herpesvirus 5]. NCBI Reference Sequence: YP_081523.1, Dep. Sep. 16, 2004.
Davison et al., "The human cytomegalovirus genome revisited: comparison with the chimpanzee cytomegalovirus genome," J. Gen. Virol., 2003, 84:17-28.
Declaration Andrew Geall dated Sep. 11, 2014.
Declaration by Prof. Peter Liljestrom, dated Mar. 31, 2019 submitted in EP 2591114.
Declaration by Prof. Peter Liljestrom, dated Aug. 7, 2018 submitted in EP 2591114, and attachments including Curriculum Vitae and List of Publications.
U.S. Appl. No. 17/808,519, filed Jun. 23, 2022.
U.S. Appl. No. 17/848,294, filed Jun. 23, 2022.
U.S. Appl. No. 17/848,299, filed Jun. 23, 2022.

(56) References Cited

OTHER PUBLICATIONS

U.S. Appl. No. 17/848,337, filed Jun. 23, 2022.
U.S. Appl. No. 61/494,745, filed Jun. 8, 2011.
U.S. Appl. No. 61/494,882, filed Jun. 8, 2011.
U.S. Appl. No. 61/404,413, filed Oct. 1, 2010.
U.S. Appl. No. 61/542,533, filed Oct. 2, 2011.
U.S. Appl. No. 61/570,690, filed Dec. 14, 2011.
U.S. Appl. No. 61/576,705, filed Dec. 16, 2011.
U.S. Appl. No. 61/578,271, filed Dec. 21, 2011.
U.S. Appl. No. 61/618,862, filed Apr. 2, 2012.
U.S. Appl. No. 61/361,828, filed Jul. 6, 2010.
Vadjy, et al., "Mucosal adjuvants and delivery systems for protein-, DNA- and RNA-based vaccines." Immunol. Cell Biol.; 2004; pp. 617-627; vol. 82(6).
Van Bleek et al., "RSV 2010: Recent advances in research on respiratory syncytial virus and other pneumoviruses," Vaccine, 29(43):7285-7291 (2011).
Van Der Velden, W., et al., "Vector Design for Optimal Protein Expression", Sep. 1, 2001, p. 576.
Van Winden EC, "Freeze-drying of liposomes: theory and practice "Methods Enzymol. 2003; 367:99-110.
Varnum et al., "Identification of proteins in human cytomegalovirus (HCMV) particles: the HCMV proteome," J. Virol., 2004, 78(20):10960-10966.
Vasiljeva et al., "Identification of a novel function of the alphavirus capping apparatus," Journal of Biological Chemistry, 2000; 275(23):17281-17287.
Vassilev, et al., "Microparticle-mediated RNA immunization against bovine viral diarrhea virus." Vaccine; 2001; pp. 2012-2019; vol. 19.
Vignuzzi, et al., "Naked RNA immunization with replicons derived from poliovirus and Semliki Forest virus genomes for the generation of a cytotoxic T cell response against the influenza A virus nucleoprotein." Journal of General Virology; 2001; pp. 1737-1747; vol. 82(7).
VirTis Advantage Plus marketing brochure 2008.
VirTis Advantage Plus specification sheet 2013.
Wang et al., "Human cytomegalovirus virion protein complex required for epithelial and endothelial cell tropism," Proc. Natl. Acad. Sci. USA, 2005, 102(5):18153-18158.
Wang, et al., "pH-sensitive immunoliposomes mediate target-cell-specific delivery and controlled expression of a foreign gene in mouse." Proc. Natl. Acad. Sci. USA; 1987; pp. 7851-7855; vol. 84.
Ward, et al., "Generation of CTL responses using Kunjin replicon RNA" Immunology and Cell Biology; 2003; pp. 73-78; vol. 81(1).
Weide, et al., "Direct Injection of Protamine-protected mRNA: Results of a Phase 1/2 Vaccination Trial in Metastatic Melanoma Patients." Journal of Immunotherapy; 2009; pp. 498-507; vol. 32(5).
Weide, et al., "Results of the First Phase 1111 Clinical Vaccination Trial with Direct Injection of mRNA," Journal of Immunotherapy; 2008; pp. 180-188; vol. 31(2).
Weissman et al., "HIV Gag mRNA Transfection of Dendritic Cells (DC) Delivers Encoded Antigen to MHC Class I and II Molecules, Causes DC Maturation, and Induces a Potent Human in Vitro Primary Immune Response," The Journal of Immunology, 2000, 165 (8), 4710, published on Oct. 15, 2000.
Whitehead et al., "Knocking down barriers: advances in siRNA delivery" Nature Reviews Drug Discovery; 2009; pp. 129-138; vol. 8.
Wille et al., "A human cytomegalovirus gO-null mutant fails to incorporate gH/gL into the virion envelope and is unable to enter fibroblasts and epithelial and endothelial cells," J. Virol., 2010, 84(5):2585-2596.
Willis et al., "Liposome-Anchored Vascular Endothelial Growth Factor Aptamers," Bioconjugate Chem., vol. 9, (1998), pp. 573-582.
Wilson et al., "Biological properties of poliovirus encapsulated in lipid vesicles: Antibody resistance and infectivity in virus-resistant cells", Proc. Natl. Acad. Sci. USA; 1977; pp. 3471-3475; vol. 74, No. 8.
Wilson, et al., "The Introduction of Poliovirus RNA into Cells via Lipid Vesicles (Liposomes)." Cell, 1979, vol. 17, pp. 77-84.
Wilson, Kaley et al.; "The combination of stabilized plasmid lipid particles and lipid nanoparticle encapsulated CpG containing oligodexoynucleotides as a systemic genetic vaccine", The Journal of Gene Medicine; 11; p. 14-25; 2009.
Wisse et al. 2008.
Wloch, et al., "Safety and Immunogenicity of A Bivalent of CMV DNA Vaccine in Healthy in Healthy Adult Subjects." J Infect Dis; 2008; pp. 1634-1642; vol. 197(12).
Woodward M, Marko A, Galea S, Eagel B, Straus W, "Varicella Virus Vaccine Live: A 22-Year Review of Postmarketing Safety Data," Open Forum Infect Dis. Aug. 1, 2019;6(8):ofz295. doi: 10.1093/ofid/ofz295. PMID: 31392326; PMCID: PMC6685817. (Year: 2019).
Xiong et al., "Sindbis virus: an efficient, broad host range vector for gene expression in animal cells," Science, 243:1188-1191 (1989).
Xu et al., "Characterization of immune Responses Elicited in Macaques Immunized Sequentially with Chimeric VEE/SIN Alphavirus Replicon Particles Expressing SIVGag and/or HIVEnv and with Recombinant HIVgp 140Env Protein," Aids Research and Human Retroviruses, Mary Ann Liebert, 22(10):1022-1030 (2006).
Xu et al., "Sequential priming and boosting with heterologous HIV immunogens predominantly stimulated T cell immunity against conserved epitopes," Aids; 20(18); 2293-2303; Nov. 28, 2006.
Xu, et al., "Clinical Trials and Translational Medicine Commentary: Drug Delivery Trends in Clinical Trials and Translational Medicine: Challenges and Opportunities in the Delivery of Nucleic Acid-Based Therapeutics," Journal of Pharmaceutical Sciences, vol. 100, No. 1, (2011), pp. 38-52.
Xu, Y., et al., Physicochemical characterization and purification of cationic lipoplexes, Biophys J., 1999, 77(1):341-53.
Xue HY, Guo P, Wen WC, Wong HL. "Lipid-Based Nanocarriers for RNA Delivery," Curr Pharm Des. 2015;21(22):3140-7. doi: 10.2174/1381612821666150531164540. PMID: 26027572; PMCID: PMC4618487. (Year: 2015).
Yadava et al., Effect of lyophilization and freeze-thawing on the stability of siRNA-liposome complexes. AAPS Pharm Sci Tech, vol. 9. No. 2, Jun. 2008.
Yamamoto, et al. "Current prospects for mRNA gene delivery". Eur. J. of Pharma and Biopharm 71, 484-489 (2009).
Yang, J-P., et al., "Overcoming the inhibitory effect of serum on lipofection by increasing the charge ratio of cationic liposome to DNA," Gene Therapy, vol. 4, 1997, pp. 950-960; 1997.
Yarian et al., (1999) Sep. 1, 1999 "Structural and Functional Roles of the N1- and N3-Protons of ψ at tRNA's Position 39," Nucleic Acids Research, vol. 27, No. 17, pp. 3542-3549.
Yi, et al., "A Cationic Lipid Emulsion/DNA Complex as a Physically Stable and Serum-Resistant Gene Delivery." Pharmaceutical Research; 2000; pp. 314-320; vol. 17.
Ying et al. "Cancer therapy using a self-replicating RNA vaccine" Nat. Med.; vol. 5; pp. 823-827; 1999.
U.S. Appl. No. 61/223,347, filed Jul. 6, 2009, Geall et al.
U.S. Appl. No. 61/280,510, filed Nov. 4, 2009, Cullis et al.
U.S. Appl. No. 61/223,347, priority document to WO2011005799.
Aberle, "Humeral and Cellular Immune Response to RNA Immunization with Flavivirus Replicons Derived from Tick-Borne Encephalitis Virus", Journal of Virology; 2005; pp. 15107-15113; vol. 79(24).
Acheampong, Samuel et al.; "Ionization and transfection activity of n-methyl-substituted carbamoyl-cholesterol derivatives", Journal of Biophysical Chemistry, vol. 2, No. 2, 53-62; 2011.
Adler et al., "Role of human cytomegalovirus UL131A in cell type-specific virus entry and release," J. Gen. Virol., 2006, 87:2451-2460.
Agris et al., (1999) "Thermodynamic Contribution of Nucleoside Modifications to Yeast tRNAphe Anticodon Stem Loop Analogs," Acta Biochimica Polonica, vol. 46, No. 1, pp. 163-172.
Aissaoui et al: "Efficient topical delivery of plasmid DNA to lung in vivo mediated by putative triggered, PEGylated pDNA nanoparticles", Journal of Controlled Release, Elsevier, Amsterdam, NL, vol. 154, No. 3, Jun. 4, 2011 Jun. 4, 2011), pp. 275-284.
Amidi et al. "Antigen-expressing immunostimulatory liposomes as a genetically programmable synthetic vaccine." Systems and Synthetic Biology, vol. 5, 2011, pp. 21-31. (Year: 2011).

(56) References Cited

OTHER PUBLICATIONS

Amidi et al. "Optimization and quantification of protein synthesis inside liposomes." Journal of Liposome Research, vol. 20(1), 2010, pp. 73-83. (Year: 2010).

Amidi, "Induction of humoral and cellular immune responses by antigen-expressing immunostimulatory liposomes." Journal of Controlled Release; Aug. 1, 2012; p. 3, left-hand column p. 20, lines 13-14 example 1.

Anderson et al. "Incorporation of pseudouridine into mRNA enhances translation by diminishing PKR activation," Nucleic Acids Research, 38(17):5884-5892 (2010).

Anderson et al., Nucleic Acids Research (2011), 39(21), 9329, published online on Aug. 3, 2011.

Andries et al., (2015) Sep. 3, 2015 "N(1)-Methylpseudouridine-Incorporated mRNA Outperforms Pseudouridine-Incorporated mRNA by Providing Enhanced Protein Expression and Reduced Immunogenicity in Mammalian Cell Lines and Mice," Journal of Controlled Release, vol. 217, pp. 337-344.

Annex to the communication in Opposition against EP 3 492 109 B1 by the Opposition Division dated Apr. 13, 2022.

Anonymous, "Mengovirus", Wikipedia, (Apr. 25, 2020), pp. 1-2, URL: https://en.wikipedia.org/wiki/Mengovirus.

A-Plus™ Poly(A) Polymerase Tailing Kit Protocol Nov. 16, 2006 (Capture Date).

Applicant's Jun. 26, 2017 response in opposition of European Patent Application 12738679.5.

Application underlying the present patent as filed with the application No. EP 18 153 312.6.

Arvin AM, Gershon AA. Live attenuated varicella vaccine. Annu Rev Microbial. 1996;50:59-100.

Aso and Yoshioka: "Effect of freezing rate on physical stability of lyophilized cationic liposomes", Chem Pharm. Bull. 53(3) 301-204 (2005).

Atwood, et al., "Comprehensive Supramolecular Chemistry II" Gen. Prin. of SupraMol. Chem. and Mol. Recogn.; pp. 141-143.

Ausubel et al., Short protocols in molecular biology.

Auxiliary requests 1, 2 and 3 (claims 1-13) filed in relation to the Opposition of European Patent No. 2590676B1 Appln No. 11741348.4) (6 pages).

Babiuk, S., et al., "Electroporation improves the efficacy of DNA vaccines in large animals," Vaccine; 2002, pp. 3399-3408; vol. 20(27-28).

Bagarazzi, M. L., et al., "Immunotherapy against HPV16118 generates potent TH1 and cytotoxic cellular immune responses," Science Translational Medicine; 2012; vol. 4(155), pp. 1-14.

Bahl K, Senn JJ, Yuzhakov 0, Bulychev A, Brito LA, Hassett KJ, Laska ME, et. al. "Preclinical and Clinical Demonstration of Immunogenicity by mRNA Vaccines against H10N8 and H7N9 Influenza Viruses," Mol Ther. Jun. 7, 2017;25(6):1316-1327. Epub Apr. 27, 2017. Erratum in: Mol Ther. Aug. 3, 2022;30(8):2874. (Year: 2017).

Bai et al., "Gene Transfer to Vein Graft Wall by HVJ-Liposome Method: Time Course and Localization fo Gene Expression," Ann Thorac Surg, vol. 66, (1998), pp. 814-820.

Bailey et al., "Modulation of membrane fusion by asymmetric transbilayer distributions of amino lipids," Biochemistry, 33:12573-80 (1994).

Balasuriya et al., "Expression of the two major envelope proteins of equine arteritis virus as a heterodimer is necessary for induction of neutralizing antibodies in mice immunized with recombinant venezuelan equine encephalitis virus replicon particles," J. Virol., 2000, 74(22): 10623-10630.

Barai, V.N. et al. Production of highly purified RNA from yeast using calcium. Applied Biochemistry and Microbiology. 1995; 31(5): 421-424.

Barichello JM, et al., Complexation of siRNA and pDNA with cationic liposomes: the important aspects in lipoplex preparation, Methods Mil. Biol., 2010, 605: 461-72 (Nov. 21, 2009).

Barnett et al., "Antibody-Mediated Protection against Mucosa! Simian-Human Immunodeficiency Virus Challenge of Macaques Immunized with Alphavirus Replicon Particles and Boosted with Trimeric Envelope Glycoprotein in MF59 Adjuvant," Journal of Virology, 84(12):5975-5985 (2010).

Barratt, "Therapeutic applications of colloidal drug carriers." PSTT, 2000, vol. 3, No. 5, pp. 163-171.

Bauer et al., "Toll-like receptors (TLRs) and innate immunity", Handbook of Experimental Pharmacology, ISBN 978-3-540-72166-6, 2008, pp. i-xi, 1-240, and a cover page (2008).

Bernstein et al., "Randomized, double-blind, Phase 1 trial of an alphavirus replicon vaccine for cytomegalovirus in CMV seronegative adult volunteers," Vaccine, 28:484-493 (2010).

Bettinger T et al. "Peptide-Mediated RNA Delivery: A Novel Approach for Enhanced Transfection of Primary and Post-Mitotic Cells," (2001) Nucleic Acids Research 29(18): 3882-3891.

Bettinger, T., et al., "Recent Developments in RNA-Based strategies for cancer gene therapy", Current Opinion in Molecular Therapeutics, Current Drugs, London, GB, vol. 3, No. 2, Apr. 1, 2001, pp. 116-124.

Biochemistry/Lubert Stryer (1995) 4th Ed.: title pages and p. 23.

BioRad Product catalog post-published evidence.

Birdi, K.S., (Ed.), Handbook of Surface and Colloidal Chemistry, CRC Press., Boca Raton, pp. 119-156.

Blakney, "The next generation of RNA vaccines: self-amplifying RNA." Document obtained from https://portlandpress.com/biochemist/article/43/4/14/229206/The-next-generation-of-RNA-vaccines-self on Sep. 20, 2021, originally published Aug. 2021, pp. 14-17. (Year: 2021).

BMGF Report, "Summary of stability data for licensed vaccines," Working in Tandem Ltd, 2012, pp. 1-17.

Bogers, et al., "Macaques Primed with Self-Amplifying RNA Vaccines Expressing HIV-1 Envelope and Boosted with Recombinant Protein Show Potent T- and B-Cell Responses" poster at the AIDS Vaccine 2012 meeting; Sep. 9-12, 2012; Boston, MA USA.

Bogers, et al., "Potent Immune Responses in Rhesus Macaques Induced by Nonviral Delivery of a Self-amplifying RNA Vaccines Expressing HIV Type 1 Envelope With a Cationic Nanoemulsion." J. Infectious Disease; 2015; pp. 947-955; vol. 211.

Boxus, M., et al., "DNA immunization with plasmids encoding fusion and nucleocapsid proteins of bovine respiratory synctial virus induces a strong cell-mediated immunity and protects calves against challenge," Journal of Virology; 2007; pp. 6879-6889, vol. 81(13).

Bramwell, "The rational design of vaccines," (DDT. 2005; 10(22): 1527-1534).

Brand et al., Biochem. J. (1978), 169, 71-77.

Bringmann et al., "RNA Vaccines in Cancer Treatment," Journal of Biomedicine and Biotechnology, 2010:1-12 (2010).

Brito et al., "Self-Amplifying mRNA Vaccines", Advances in Genetics, vol. 89; p. 179-233; 2015.

Brito et al., "A Cationic Nanoemulsion for the delivery of next-generation RNA vaccines," Molecular Therapy, 2014; pp. 2118-2129, vol. 22.

Britt et al., "Cell surface expression of human cytomegalovirus (HCMV) gp55-116 (gB): use of HCMV-recombinant vaccinia virus-infected cells in analysis of the human neutralizing antibody response," J. Virol., 1990, 64(3):1079-1085.

Ju J., et al., "Novel Cholesterol-Based Cationic Lipids as Transfecting Agents of DNA for Efficient Gene Delivery," Int. J. Mol. Sci. 16:5666-5681; 2015.

Kamrud KI, Alterson K, Custer M, Dudek J, Goodman C, Owens G, Smith JF. Development and characterization of promoterless helper RNAs for the production of alphavirus replicon particle. J Gen Virol. Jul. 2010; 91(Pt 7):1723-7. Epub Feb. 24, 2010.

Kariko (2008) "Incorporation of Pseudouridine into mRNA yields Superior Nonimmunogenic Vector with Increased Translational Capacity and Biological Stability," Mol Ther., vol. 16, No. 11, pp. 1833-1840.

Kariko and Weissman, (2007) "Naturally Occurring Nucleoside Modifications Suppress the Immunostimulatory Activity of RNA: Implication for Therapeutic RNA Development," Curr Opin Drug Disc & Dev., vol. 10, No. 5, pp. 524-532.

Kariko et al., (2005) "Suppression of RNA Recognition by Toll-Like Receptors: The Impact of Nucleoside Modification and the Evolutionary Origin of RNA," Immunity, vol. 23, pp. 165-175.

(56) References Cited

OTHER PUBLICATIONS

Kariko et al., (2012) "Increased Erythropoiesis in Mice Injected with Submicrogram Quantities of Pseudouridine-Containing mRNA Encoding Erythropoietin," Mal Ther 20(5):948-53.
Kariko et al., Nucleic Acids Research (2011), 39 (21), e142, published online on Sep. 2, 2011.
Kariko, et al., "mRNA Is an Endogenous Ligand for Toll-like Receptor 3*"; The Journal of Biological Chemistry; 2004; vol. 279, No. 13; pp. 12542-12550.
Kariko, et al., "Suppression of RNA Recognition by Toll-like Receptors: The Impact of Nucleoside Modification and the Evolutionary Origin of RNA"; Immunity; 2005; vol. 23; pp. 165-175.
Kariko, Muramatsu, Welsh, Ludwig, Kato, Akira and Weissman (2008) Incorporation of Pseudouridine Into mRNA Yields Superior Nonimmunogenic Vector With Increased Translational Capacity and Biological Stability. Molecular Therapy vol. 16 No. 11, 1833-1840.
Kawano, et al., "Effects of Polyethylene Glycol Spacer Length and Ligand Density on Folate Receptor Targeting of Liposomal Doxorubicin In Vitro." Journal of Drug Delivery, 2011, vol. 2011, No. 160967, pp. 1-6.
Kawauchi et al., "Gene Therapy for Attenuating Cardiac Allograft Arteriopathy using Ex Vivo E2F Decoy Transfection by HVJ-AVE-Liposome Method in Mice and Nonhuman Primates," Circulation Research, (2000), pp. 1063-1068.
Khan, K. H., "DNA vaccines: roles against diseases," Germs; 2013; pp. 26-35; vol. 3(1).
Kierzek & Kierzek et al., (2001) Jun. 21, 2001 "Influence of N6-Isopentenyladenosine (k6A) on Thermal Stability of RNA Duplexes," Biophysical Chemistry, vol. 91, pp. 135-140.
Kimura et al. "Recombinant Varicella-Zoster Virus Glycoproteins E and I: Immunologic Responses and Clearance of Virus in a Guinea Pig Model of Chronic Uveitis", 1998 Journal of Infectious Diseases 178:310-317.
Kimura et al. "Varicella-Zoster Virus Glycoproteins E and I Expressed in Insect Cells Form a Heterodimer That Requires the N-Terminal Domain of Glycoprotein I", 1997 Virology 233:382-391.
Kinnan, et al., "Enhanced Immunogenicity to *Mycobacterium tuberculosis* by Vaccination with an Alphavirus Plasmid Replicon Expressing Antigen 85A" Infection and Immunity; 2003; pp. 575-579; vol. 71(1).
Kirman, et al., "Enhanced Immunogenicity to *Mycobacterium tuberculosis* by Vaccination with an Alphavirus Plasmid Replicon Expressing Antigen BSA" Infection and Immunity; 2003; pp. 575-579; vol. 71(1).
Kit Protocol Nov. 16, 2006 (Capture Date).
Kita et al: "Replication of Genetic Information with Self-Encoded Replicase in Liposomes", Chembiochem, vol. 9, No. 15,Oct. 13, 2008 (Oct. 13, 2008), pp. 2403-2410.
Kitajima et al., "Efficient Transfer of Synthetic Ribozymes into Cells using Hemagglutinating Virus of Japan (HVJ)-Cationic Liposomes," The Jounral of Biological Chemistry, vol. 272, No. 43, (1997), pp. 27099-27106.
Klibanov A L et al: "Amphipathic polyethyleneglycols effectively prolong the circulation time of liposomes", FEBS Letters, Elsevier, Amsterdam, NL, vol. 268, No. 1,Jul. 30, 1990 (Jul. 30, 1990), pp. 235-237.
Knipe et al., "Fields Virology," 4th edition, Lippincott Williams & Wilkins, 2001; pp. 690-692; vol. 1, p. 2.
Kofler, et al. "Mimicking live flavivirus immunization with a noninfectious RNA vaccine." Proc. Natl. Acad. Sci. USA; 2004; pp. 1951-1956; vol. 101(7).
Kornbluth at al. "Immunostimulatory combinations: designing the next generation of vaccine adjuvants," Journal of Leukocyte Biology, 2006, vol. 80, pp. 1084-1102.
Kreiter et al., "Tumor Vaccination using Messenger RNA: Prospects of a Future Therapy," Current Opinion in Immunology, vol. 23, (2011), pp. 399-406.
Kulkarni, et al, "Factors affecting microencapsulation of drugs in liposomes", Journal of Microencapsulation, 12(3), 229-46. (1995).

Kumar et al., "Toll-like receptors and innate immunity," Biochemical and Biophysical Research Communications, 388:621-625 (2009).
Kumar, et al., "Single histidine residue in head-group region is sufficient to impart remarkable gene transfection properties to cationic lipids: evidence for histidine-mediated membrane fusion at acidic pH". Gene Therapy; 2003; vol. 10; pp. 1206-1215.
Kumar, et al., "New Histidylated Cationic Lipids for DNA- and mRNA-Based Lipofection," Molecular Therapy 9(S1): S258-S259, 2004.
Kutinova et al., "Immune response to vaccinia virus recombinants expressing glycoproteins gE, gB, gH, and gL of varicella-zoster virus," Virol., 2001, 280:211-220.
Kutzler, et al., "DNA vaccines; ready for prime time?" Nature Reviews; Genetics; 2008; pp. 776-788; vol. 9(10).
Lazzaro et al., "CD8 T-cell priming upon mRNA vaccination is restricted to bone-marrow-derived antigen-presenting cells and may involve antigen transfer from myocytes," Immunology, 146:312-326 (2015).
Lee et al., "Multiagent vaccines vectored by Venezuelan equine encephalitis virus replicon elicits immune responses to Marburg virus and protection against anthrax and botulinum neurotoxin in mice," Vaccine, Elsevier, Amsterdam, NL, vol. 24, No. 47-48; pp. 6886-6892; Nov. 17, 2006.
Lee, et al., "Venezuelan Equine Encephalitis Virus-Vectored Vaccines Protect Mice Against Anthrax Spore Challenge." Infection and Immunity; 2003; pp. 1491-1496; vol. 71.
Leitner et al. "DNA and RNA-based vaccines: principles, progress and prospects" Vaccine 18:765-77 (1999).
Leroueil PR, et. al., "Wide varieties of cationic nanoparticles induce defects in supported lipid bilayers" Nano Lett. Feb. 2008;8(2):420-4. Epub Jan. 25, 2008. (Year: 2008).
Levine, et al., Vaccine development strategies for improving immunization: the role of modern immunology. Nature Immunol.; 2004; pp. 460-464; vol. 5(5).
Levy; "Quantitation of supercoiled circular content in plasmid DNA solutions using a fluorescence based method", Nucleic Acids Res.; 2000; 28:e57.
Li et al., "Protection against Respiratory Syncytial Virus Infection by DNA Immunization," J Exp Med., vol. 188, (1998), pp. 681-688.
Liljestrom, et al., "A new generation of animal cell expression vectors based on the Semliki Forest virus replicon," Biotechnology, 9:1356-1361 (1991).
Liljestrom, et. al., "In vitro mutagenesis of a full-length cDNA clone of Semliki Forest virus: the small 6,000-molecular-weight membrane protein modulates virus release," Journal of Virology, Aug. 1991; 65(8): 4107-4113.
Liu Y & Huang L "Designer Lipids Advance Systemic siRNA Delivery," (2010) Molecular therapy 18(4): 669-670.
Ljungberg et al., "Increased Immunogenicity of a DNA-Launched Venezuelan Equine Encephalitis Virus-Based Replicon DNA Vaccine," Journal of Virology, Dec. 2007, p. 13412-13423.
Ljungman et al., "Definitions of cytomegalovirus infection and disease in transplant recipients," Clin. Infect. Dis., 2002, 34:1094-1097.
Lobue, et al. "Multivalent norovirus vaccines induce strong mucosal and systemic blocking antibodies against multiple strains." Vaccine; 2006; pp. 5220-5234; vol. 24.
Lonez, et al., "Cationic liposomal lipids: From gene carriers to cell signaling." Progress in Lipid Research; 2008; pp. 340-347; vol. 47(5).
Lorenzi, et al. "Intranasal vaccination with messenger RNA as a new approach in gene therapy: use against tuberculosis," BMC Biotechnology 10.1 (2010): 1-11.
Lu, et al., "Optimization of methods to achieve mRNA-mediated transfection of tumor cells in vitro and in vivo employing cationic liposome vectors," Cancer Gene Ther., 1(4):245-252 (1994) (abstract).
Lundstrom et al., "Biology and application of alphaviruses in gene therapy", Gene Therapy; vol. 12; Suppl 1; pp. S92-S97, 2005.
Sharma, et al., "To scale or not to scale: the principles of does extrapolation." British Journal of Pharmacology; 2009; pp. 907-921; vol. 157.

(56) References Cited

OTHER PUBLICATIONS

Shimamura et al., "Human cytomegalovirus infection elicits a glycoprotein M (gM)/gN-specific virus-neutralizing antibody response," J. Virol., 2006, 80(9):4591-4600.
Silva, et al "Effect of ultrasound parameters for unilamellar liposome preparation" Ultrasonics Sonochemistry, 17(3), 628-32 (2010).
Singh et al., "The Effect of CTAB Concentration in Cationic PLG Microparticles on DNA Adsorption and in Vivo Performance," Pharmaceutical Research, (2003), vol. 20, pp. 247-251.
Singh, et al., "Cationic microparticles: A potent delivery system for DNA vaccines" Proc Natl Acad Sci USA; 2000; pp. 811-816; vol. 97(2).
Size Homogeneity of a Liposome Preparation is Crucial for Liposome Biodistribution in Vivo.
Smerdou, et al., "Non-viral amplification systems for gene transfer: Vectors based on alphaviruses," Curr Opin Mal Ther; 1999; pp. 244-251; vol. 1(2).
Smith Korsholm, Karen, et al. "The adjuvant mechanism of cationic dimethyldioctadecylammonium liposomes," Immunology 121(2) (2007): 216-226.
Soong et al., "PEG Molecular Weight and Lateral Diffusion of PEG-ylated Lipids in Magnetically Aligned Bicelles," BBA, (2007), pp. 1805-1814.
Spelios et al., "Effect of Spacer Attachment Sites and pH-Sensitive Headgroup Expansion on Cationic Lipid-Mediated Gene Delivery of Three Novel Myristoyl Derivatives," Biophys. Chem. 129 (2007), 137-147.
Sriwongsitanont, et al. "Physiochemical Properties of PEG-Grafted Liposomes." Chem Pharm Bull; 2002; pp. 1238-1244; vol. 50(9).
Stagno et al., "Cytomegalovirus," In Infectious Diseases of the Fetus and Newborn Infant, 6th edition, JS Remington and JO Klein (ed.), WB Saunders, Philadelphia, PA, 1995, pp. 312-353.
Stedman's Medical Dictionary; 27th Edition; Lippincott, Williams & Wilkins; published 2000, p. 1963.
Strauss, J. H. et al., "The Alphaviruses: Gene Expression, Replication, and Evolution," Microbiological Reviews, 58 (3): 491-562 (1994) (excerpt).
Strejan, "Suppression of Chronic-Relapsing Experimental Allergic Encephalomyelitis in Strain-13 Guinea Pigs by Administration of Liposome-Associated Myelin Basic Protein", Journal of Neuroimmunology; vol. 7; 1984; pp. 27-41.
Stuart, et al, "A new liposomal formulation for antisense oligodeoxynucleotides with small size, high incorporation efficiency and good stability", Biochimica et Biophysica Acta, 1463(2), 219-29 (2000).
Su et al In Vitro and in Vivo mRNA Delivery using Lipid-Enveloped pH-Responsive Polymer Nanoparticles, Molecular Pharmaceutics, vol. 8, (2011) pp. 774-787.
Submitted claims to the EPO on Sep. 30, 2008 in the case EP 06 81 3536.7 (EP1979364) prior art under Art. 54 (2) EPC.
Sugiyama, T., "Immunoadjuvant effects of polyadenylic:polyuridylic acids through TLR3 and TLR7", Int. Immunolo. 20 (1): 1-9 (2008)—XP002665154.
Szebeni J, et. al., "Activation of complement by therapeutic liposomes and other lipid excipient-based therapeutic products: prediction and prevention," Adv Drug Deliv Rev. Sep. 16, 2011;63(12):1020-30. Epub Jul. 14, 2011. (Year: 2011).
Szebeni J, Storm G. "Complement activation as a bioequivalence issue relevant to the development of generic liposomes and other nanoparticulate drugs," Biochem Biophys Res Commun. Dec. 18, 2015;468(3):490-7. doi: 10.1016/j.bbrc.2015.06.177. Epub Jul. 14, 2015. PMID: 26182876. (Year: 2015).
Szebeni J., "Complement activation-related pseudoallergy: a stress reaction in blood triggered by nanomedicines and biolocials," Mol Immunol. Oct. 2014;61(2):163-73. Epub Aug. 12, 2014. (Year: 2014).
Szoka, et al., "Procedure for preparation of liposomes with large internal aqueous space and high capture by reverse-phase evaporation," Proc Natl Acad Sci U S A, 75(9) (1978): 4194-4198.

Tang et al. "Design of Freeze-Drying Processes for Pharmaceuticals: Practical Advice," Pharmaceutical Research, vol. 21, No. 2, Feb. 2004.
Tannous, et al., Secreted blood reporters: Insights and applications, Biotechnol. Adv., 2011, 29(6):997-1003.
Taylor, et al., "DNA vaccination against respiratory syncytial virus in young calves." Vaccine; 2005; pp. 1242-1250; vol. 23(10).
Tcherepanova et al, "Ectopic Expression of a Truncated CD40L Protein from Synthetic Post-Transcriptionally Capped RNA in Dendritic Cells Induces High Levels of IL-12 Secretion," BMC Molecular Biology 2008, 9:90.
The International Association for the Properties of Water and Steam, Pizer Czech Republic, Sep. 2011.
ThermoFisher Scientific, "Ribosomal RNA Sizes", submitted in EP Opposition against Application No. EP 2591103 on Jan. 14, 2022, 1 page.
Third Party Observations under Art. 115 EPC Nov. 3, 2016, from EP Appl. No. 11736499.2; pp. 1-17.
Thompson et al., "Mucosal and systemic adjuvant activity of alphavirus replicon particles," Proceedings of the National Academy of Sciences, 103{10):3722-3727 (2006).
Tonkin, D. R. et al., "Alphavirus Replicon-Based Enhancement of Mucosal and Systemic Immunity is Linked to the Innate Response Generated by Primary Immunization," Vaccine, 28(18): 3238-3246 (2010).
Torchilin, et al., "Poly(ethylene glycol) on the liposome surface: on the mechanism of polymer-coated liposome longevity." Biochimica et Biophysica Acta, 1994, vol. 1195, pp. 11-20.
Tranchant, I et al. "Physicochemical Optimisation of Plasmid Delivery by Cationic Lipids," (2004) J Gene Med 6: S24-S35.
Tseng et al., "Liposomes incorporated with cholesterol for drug release triggered by magnetic field," Journal of Medical and Biological Engineering, vol. 27, No. 1 (2007), 29-34.
Tubulekas et al., "Alphavirus expression vectors and their use as recombinant vaccines: a minireview" 190 Gene 191-195 (1997).
U.S. Appl. No. 17/560,019, filed Dec. 22, 2021.
U.S. Appl. No. 17/511,762, filed Oct. 27, 2021.
U.S. Appl. No. 17/512,258, filed Oct. 27, 2021.
U.S. Appl. No. 17/560,052, filed Dec. 22, 2021.
U.S. Appl. No. 17/560,059, filed Dec. 22, 2021.
U.S. Appl. No. 17/560,092, filed Dec. 22, 2021.
U.S. Appl. No. 17/560,116, filed Dec. 22, 2021.
U.S. Appl. No. 17/560,138, filed Dec. 22, 2021.
U.S. Appl. No. 61/529,878, filed Aug. 31, 2011.
Uddin SN, "Cationic Lipids Used in Non-Viral Gene Delivery Systems," Biotechnology and Molecular Biology Review 2(3): 058-067, 2007.
Ulmer, et al., "Heterologous Protection Against Influenza by Injection of DNA Encoding a Viral Protein." Science; 1993; pp. 1745-1749; vol. 259.
U.S. Appl. No. 61/505,088.
U.S. Appl. No. 16/714,877, filed Dec. 16, 2019.
Veerle Noe and Christian Soltmann, "mRNA Technologies: Insight Report", European Patent Office, published online on Oct. 25, 2023 (retrieved Oct. 27, 2023 at https://link.epo.org/web/business/patent-insight-reports/mrna_technologies_2023_EN.pdf) and announcement of the report, which memorializes the Oct. 25, 2023 publication date) (retrieved Oct. 27, 2023 at https://www.epo.org/en/news-events/news/epo-publishes-report-life-saving-mrna-technologies).
Office Action, dated Jan. 20, 2023, issued in U.S. Appl. No. 17/512,258.
Office Action, dated Mar. 3, 2023, issued in U.S. Appl. No. 18/080,101.
Office Action, dated Mar. 13, 2023, issued in U.S. Appl. No. 18/080,075.
Office Action, dated Mar. 13, 2023, issued in U.S. Appl. No. 18/080,090.
Office Action, dated Mar. 16, 2023, issued in U.S. Appl. No. 18/065,111.
Office Action, dated Mar. 16, 2023, issued in U.S. Appl. No. 18/065,106.
Office Action, dated Mar. 16, 2023, issued in U.S. Appl. No. 18/065,069.

(56) References Cited

OTHER PUBLICATIONS

Office Action, dated Mar. 16, 2023, issued in U.S. Appl. No. 18/065,076.
Office Action, dated Mar. 16, 2023, issued in U.S. Appl. No. 18/065,100.
Office Action, dated Mar. 16, 2023, issued in U.S. Appl. No. 18/065,089.
Office Action, dated Apr. 6, 2023, issued in U.S. Appl. No. 18/065,095.
Office Action, dated Apr. 4, 2023, issued in U.S. Appl. No. 18/065,109.
Office Action, dated Apr. 4, 2023, issued in U.S. Appl. No. 18/065,083.
Gamvrellis A. et al. Vaccines that facilitate antigen entry into dendritic cells. Immunol Cell Biol. Oct. 2004; 82(5): 506-516.
Gao & Hui, "Synthesis of a Novel Series of Cationic Lipids that can act as Efficient Gene Delivery Vehicles Through Systematic Heterocyclic Substitution of Cholesterol Derivatives," Gene Therapy 8 (2001), 855-863.
Garcia-Valcarcel M, Fowler WJ, Harper DR, Jeffries DJ, Layton GT. Induction of neutralizing antibody and T-cell responses to varicella-zoster virus (VZV) using Ty-virus-like particles carrying fragments of glycoprotein E (gE). Vaccine. Apr.-May 1997; 15(6-7): 709-19.
Geall, A. et al, "Nonviral delivery of self-amplifying RNA vaccines." Proceedings of the National Academy of Sciences of the United States of America, 2012, 109(36), 14604-14609.
Geall, et al. "Using self-amplifying mRNA vaccines to facilitate a rapid response to pandemic influenza" Eur. Pharm. Review 19:3 20-23 (2014).
Geisbert, et al., "Postexposure Protection of Guinea Pigs against a Lethal Ebola Virus Challenge Is Conferred by RNA Interference", Journal of Infectious Diseases; 2006; pp. 1650-1657; vol. 193.
Geldmacher et al: "Therapeutic vaccination for cancer immunotherapy: Antigen selection and clinical responses", Human Vaccines, vol. 7, No. sup1, Jan. 1, 2011 (Jan. 1, 2011), pp. 115-119.
Genini et al., "Serum antibody response to the gH/gL/pUL 128-131 five protein complex of Serum antibody response to the gH/gL/pUL 128-131 five-protein complex of human cytomegalovirus (HCMV) in primary and reactivated HCMV infections," Journal of Clinical Virology, 52:113-118 (2011).
Giraud A, Ataman-Onal Y, Battail N, Piga N, Brand D, Mandrand B, Verrier B. Generation of monoclonal antibodies to native human immunodeficiency virus type 1 envelope glycoprotein by immunization of mice with naked RNA. J Virol Methods. Apr. 1999;79(1):75-84.
Giuliani et al., "A universal vaccine for serogroup B meningococcus," Proc. Natl. Acad. Sci. U. S. A, 2006, vol. 103, No. 29, pp. 10834-10839.
Glaxosmithkline, SAM/Protein Mixed Modality Study Data, PowerPoint presentation (2019).
Goncalves, et al The effect of liposome size on the final lipid/DNA ratio of cationic lipoplexes. Biophysical Journal, 86 (3), 1554-63 (2004).
Graham, Barney, "Biological challenges and technological opportunities for respiratory syncytial virus vaccine development," Immunological Reviews, 239(1):149-166 (2011).
Graham, et al., "Priming Immunization Determines T Helper Cytokine mRNA Expression Patterns in Lungs of Mice Challenged with Respiratory Syncytial Virus." The Journal of Immunology; Aug. 15, 1993; pp. 2032-2040; vol. 151, No. 4.
Granstein, et al., "Induction of Anti-Tumor Immunity with Epidermal Cells Pulsed with Tumor-Derived RNA or Intradermal Administration of RNA." Journal of Investigative Dermatology; 2000; pp. 632-636; vol. 114(4).
Greer, C, et al., "A chimeric alphavirus RNA replicon gene-based vaccine for human parainfluenza virus type 3 induces protective immunity against intranasal virus challenge", Vaccine 25(3): 481-489 (2007)—XP005798901.
Hahn et al, "Deletion Mapping of the Encephalomyocarditis Virus Primary Cleavage Site". J. Virol. Aug. 2001; 75 (15):7215-8.

Hamm et al., "Immunostimulatory RNA is a potent inducer of antigen-specific cytotoxic and hum oral immune response in vivo," International Immunology, 2007, vol. 19(3); 297-304.
Harvey et al. Kunjin Virus Replicon Vectors for Human Immunodeficiency Virus Vaccine Development 2003 Journal of Virology vol. 77 No. 14 pp. 7796-7803.
Hassett KJ, Benenato KE, Jacquinet E, Lee A, Woods A, Yuzhakov 0, Himansu S, Deterling J, Geilich BM, Ketova T, Mihai C, Lynn A, McFadyen I, et al., "Optimization of Lipid Nanoparticles for Intramuscular Administration of mRNA Vaccines," Mol Ther Nucleic Acids. Apr. 15, 2019;15:1-11. Epub Feb. 7, 2019. (Year: 2019).
Hatakeyama, et al., "Systemic delivery of siRNA to tumors using a lipid nanoparticle containing a tumor-specific cleavable PEG-lipid." Biomaterials, 2011, vol. 32, pp. 4306-4316.
Heidel, J.D., et al., "Administration in non-human primates of escalating intravenous doses of targeted nanoparticles containing ribonucleotide reductase subunit M2 siRNA," Proc. Natl Acad Sci USA; 2007; pp. 5715-5721; vol. 104(14).
Herweijer et al., "Self-amplifying vectors for gene delivery," Advanced Drug Delivery Reviews, 27; 1997; pp. 5-16.
Heyes et al., "Cationic lipid saturation influences intracellular delivery of encapsulated nucleic acids," J Control Release; vol. 107; 2005; pp. 276-287.
Hidmark et al., "Humoral Responses against Coimmunized Protein Antigen but Not against Alphavirus-Encoded Antigens Require Alpha/Beta Interferon Signaling," Journal of Virology, 80(14):7100-7110 (2006).
Hiroshi, et al., "Replication of Genetic Information with Self-Encoded Replicase in Liposomes." ChemBioChem; Oct. 13, 2008; pp. 2403-2410; vol. 9(15).
Ho, "Cytomegalovirus," In Principles and Practice of Infectious Diseases, GL Mandell, RG Douglas, and JE Bennett (ed.), Wiley, New York, NY, 1979, pp. 1307-1323.
Hobo et al., "Immunogenicity of Dendritic Cells Pulsed with MAGE3, Survivin and B-Cell Maturation Antigen mRNA for Vaccination of Multiple Myeloma Patients," Cancer Immunol Immunother, vol. 62, (2013), pp. 1381-1392.
Hobo et al., "Improving Dendritic Cell Vaccine Immunogenicity by Silencing PD-1 Ligands using siRNA-lipid Nanoparticles Combined with Antigen mRNA Electroporation," Cancer Immunol Immunother, vol. 62, (2013), pp. 285-297.
Hobom et al., "Fast screening procedures for random transposon libraries of cloned herpesvirus genomes: mutational analysis of human cytomegalovirus envelope glycoprotein genes," J. Virol., 2000, 74(17):7720-7729.
Hoerr et al. "In vivo application of RNA leads to induction of specific cytotoxic T lymphocytes and antibodies" Eur. J. Immunol. 30; pp. 1-7; 2000.
Hoerr, I, "Plenary Lectures and Oral Presentations: Stabilized Messenger RNA (RNActive™) as a Tool for Innovative Gene Delivery," Tissue Engineering 13(4): 886-887; 2007.
Hofmann et al., "Physiochemical Properties of Bile Acids and their Relationship to Biological Properties: An Overview of the Problem," J Lip Res., vol. 25, (1984), pp. 1477-1489.
Hope, et al., "Chapter 8: Reduction of Liposome Size and Preparation of unilamellar Vesicles by Extrusion Techniques," Liposome Technology; 1993; pp. 123-139; vol. 1.
Hornung, et al., "5'-Triphosphate RNA Is the Ligand for RIG-I" Science; 2006; vol. 314; pp. 994-997.
https://www.convertunits.com/from/atmosphere+[standard]/to/mtorr.
Huang, et al., "Immunization with a bovine herpesvirus 1 glycoprotein B Dna vaccine induces cytotoxic T-lymphocyte responses in mice and cattle," Journal of General Virology; 2005; pp. 887-898; vol. 86(4).
Hwang et al., "Alpha-Methylprednisolone Conjugated Cyclodextrin Polymer-Based Nanoparticles for Rheumatoid Arthritis Therapy," International Journal of Nanomedicine, 2008, 3(3), 359-371.
Iavarone et al., "A Point Mutation in the Amino Terminus of TLR7 Abolishes Signaling without Affecting Ligand Binding", J. Immunol, (2011), vol. 186, pp. 4213-4222.
Imagines Immunization Merriam Webster's Medical Desk Dictionary; 1993; pp. 326-327.

(56) References Cited

OTHER PUBLICATIONS

Immordino, et al., "Stealth liposomes: review of the basic science, rationala, and clinical application, existing and potential." International Journal of Nanomedicine, 2006, vol. 1, pp. 297-315.
International Search Report for International Application No. PCT/2012/045847 dated Oct. 10, 2012.
International Search Report for International Application No. PCT/2012/045854 dated May 9, 2014.
Janeway CA Jr, Travers P, Walport M, et al. Immunobiology: The Immune System in Health and Disease. 5th edition. New York: Garland Science; 2001. Induced innate responses to infection. Part I, Chapter 2, "Induced innate responses to infection" pp. 87-106. Available from: https://www.ncbi.nlm.nih.oov/books/NBK27122/.
Jeffs et al., "A Scalable, Extrusion-Free Method for Efficient Liposomal Encapsulation of Plasmid DNA," Pharmaceutical Research (Mar. 2005), vol. 22, No. 3, pp. 362-372.
Johanning et al., "A Sindbis virus mRNA polynucleotide vector achieves prolonged and high level heterologous gene expression in vivo," Nucleic Acids Res, (1995), vol. 23, pp. 1495-1501.
Johnson signed Declaration dated Oct. 22, 2020 (9 pages).
Johnson, T, et al., "TLR9 agonist, but not TLR7/8, functions as an adjuvant to diminish FI-RSV vaccine-enhanced disease, while either agonist used as therapy during primary RSV infection increases disease severity", Vaccine 27 (23): 3045-3052 (2009).
Jones et al. "DNA vaccination protects against an influenza challenge in a double-blind randomised placebo-controlled phase 1b clinical trial" Vaccine 27 (2009): 2506-2512.
Jones et al.: "Long-term storage of DNA-free RNA for use in vaccine studies", BioTechniques 43:675-681 (Nov. 2007).
Ausubel et al., "Short Protocols in Molecular Biology," Chapter 11, John Wiley and Sons, New York, New York, 1999. Abstract enclosed.
BioRad catalog submitted on Sep. 1, 2022 in European Patent Application No. 19216461.
Declaration and Curriculum Vitae of Russell Johnson dated Aug. 6, 2018 submitted in opposition proceedings against European Patent No. 2591114.
Declaration and Curriculum Vitae of Russell Johnson dated May 6, 2021 submitted in opposition proceedings against European Patent No. 2750707.
Declaration of Russell Johnson dated Sep. 21, 2022 submitted in opposition proceedings against European Patent No. 2591103.
Declaration entitled "Annex A" by Russell Johnson filed on Sep. 23, 2021 in opposition of European Patent No. EP2729126.

FIG. 3
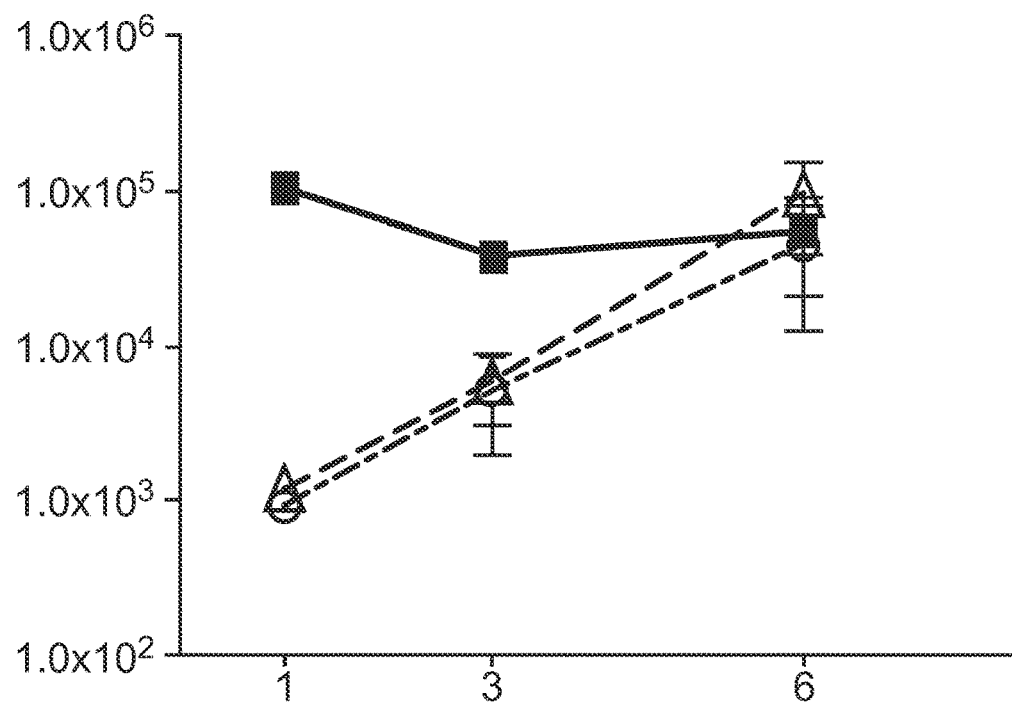
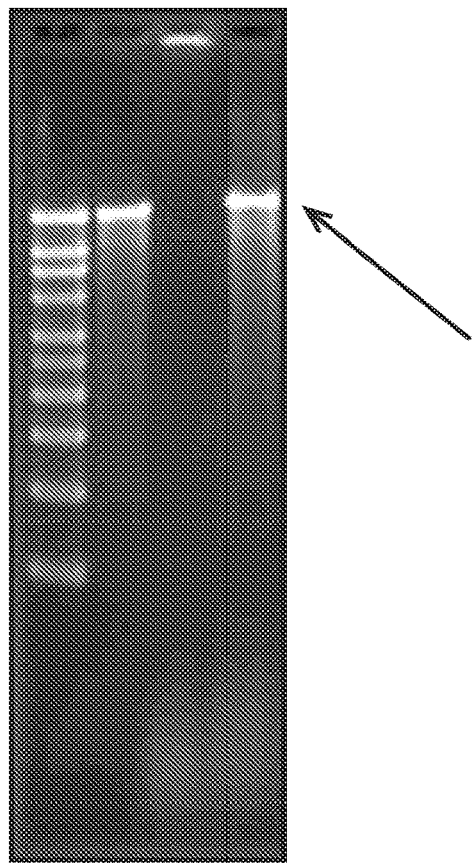
FIG. 4

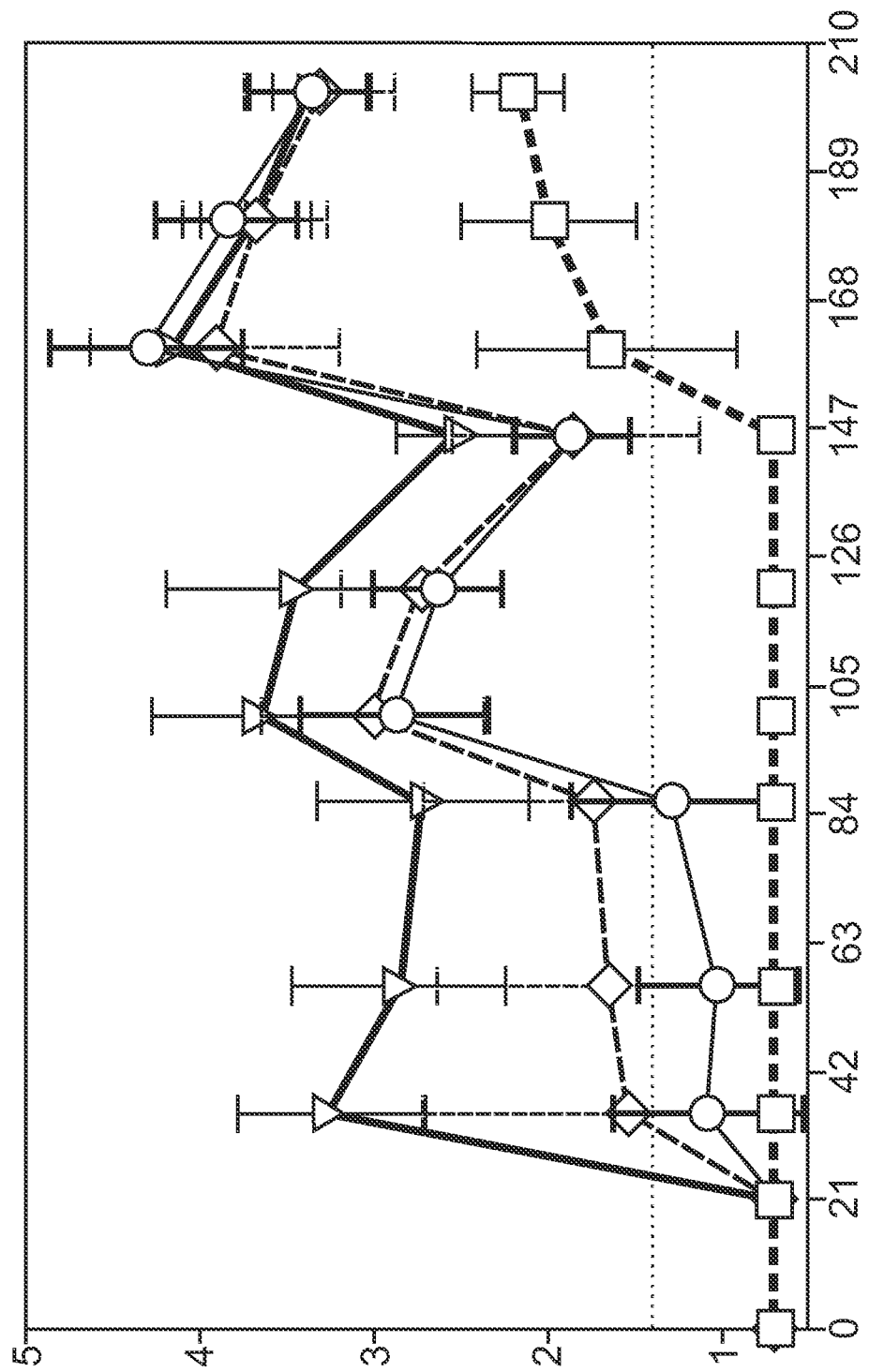

IMMUNIZATION OF LARGE MAMMALS WITH LOW DOSES OF RNA

This application is a continuation of U.S. application Ser. No. 16/656,929, filed Oct. 18, 2019, which is a continuation of U.S. application Ser. No. 13/808,153, filed Feb. 26, 2013, now U.S. Pat. No. 10,487,332, which issued Nov. 26, 2019, which is a National Stage Application under 35 U.S.C. § 371 of PCT/US2011/043096, filed Jul. 6, 2011, which claims the benefit of U.S. Provisional Application No. 61/361,794, filed Jul. 6, 2010. The complete contents of the above-listed applications are hereby incorporated herein by reference in their entireties for all purposes.

TECHNICAL FIELD

This invention is in the field of non-viral delivery of RNA for immunization.

BACKGROUND ART

The delivery of nucleic acids for immunizing animals has been a goal for several years. Various approaches have been tested, including the use of DNA or RNA, of viral or non-viral delivery vehicles (or even no delivery vehicle, in a "naked" vaccine), of replicating or non-replicating vectors, or of viral or non-viral vectors.

Various different doses of nucleic acids have been delivered in previous in vivo studies. Reference 1 delivered 50 µg of lipoplexed mRNA or DNA to mice, but also used intraglossal 1 µg and 10 µg doses to analyze luciferase expression in tongue tissue. Reference 2 delivered 12 µg of mRNA encoding influenza virus nucleoprotein to mice. Reference 3 delivered 0.1 µg, 1 µg or 10 µg of self-replicating RNA encoding β-galactosidase to mice. Reference 4 delivered 10 µg of self-replicating RNA encoding rabies virus glycoprotein to mice. Reference 5 delivered a total of 2 µg or 4 µg of DNA encoding influenza haemagglutinin to humans but did not deliver RNA.

Experience with DNA vaccines was encouraging in early work with small animals (e.g., mice) but as the technology moved into large animals (e.g., humans) it became clear that potency decreased. Thus, very high doses would be required (e.g., milligrams rather than micrograms), but clinical-grade DNA is expensive to manufacture.

There remains a need for further and improved nucleic acid vaccines.

DISCLOSURE OF THE INVENTION

According to a first aspect of the invention, RNA encoding an immunogen is delivered to a large mammal at a dose of between 2 µg and 100 µg. As shown below, a dose of 66 µg is immunogenic in calves. An adult cow has a body weight ~10× that of an adult human and so the inventor has shown that a human dose of 5-10 µg RNA is realistic.

According to a second aspect of the invention, RNA encoding an immunogen is delivered to a large mammal at a dose of 0.1 µg/kg to 1.5 µg/kg. As shown below, a dose of ~0.94 µg/kg is immunogenic in cattle. Prior art studies have used 100 ng to 10 µg RNA in mice which, with a ~20 g body weight, is 5 µg/kg to 500 µg/kg.

Thus, the invention provides a method of raising an immune response in a large mammal, comprising administering to the mammal a dose of between 2 µg and 100 µg of immunogen-encoding RNA.

The invention also provides an immunogen-encoding RNA for use in an in vivo method of raising an immune response in a large mammal, wherein the method comprises administering between 2 µg and 100 µg of the RNA to the mammal.

The invention also provides the use of an immunogen-encoding RNA in the manufacture medicament for raising an in vivo immune response in a large mammal, wherein the medicament has between 2 µg and 100 µg of immunogen-encoding RNA per unit dose.

The invention also provides a pharmaceutical composition for a large mammal, comprising between 2 µg and 100 µg of immunogen-encoding RNA per unit dose. In a typical dosage volume of 0.5 ml the concentration of the immunogen-encoding RNA will thus be between 4 µg/ml and 200 µg/ml.

The invention also provides a unit dose of a pharmaceutical composition for administration to a large mammal, wherein the unit dose comprises between 2 µg and 100 µg of immunogen-encoding RNA.

The invention also provides a delivery device (e.g., syringe, nebulizer, sprayer, inhaler, dermal patch, etc.) containing a pharmaceutical composition for administration to a large mammal, wherein the composition in the device contains between 2 µg and 100 µg of immunogen-encoding RNA.

The invention also provides a hermetically sealed container containing a pharmaceutical composition for administration to a large mammal, wherein the composition in the container contains between 2 µg and 100 µg of immunogen-encoding RNA.

The invention also provides a method of raising an immune response in a large mammal, comprising administering to the mammal between 0.1 µg and 1.5 µg RNA per kg of the mammal's body weight.

The invention also provides an immunogen-encoding RNA for use in an in vivo method of raising an immune response in a large mammal, wherein the method comprises administering between 0.1 µg and 1.5 µg RNA per kg of the mammal's body weight.

The invention also provides the use of an immunogen-encoding RNA in the manufacture medicament for raising an in vivo immune response in a large mammal, wherein the medicament has between 0.1 µg and 1.5 µg of immunogen-encoding RNA per kg of the mammal's body weight.

Administration

The invention involves administration of RNA to a large mammal. The site of administration will usually be muscle tissue, such as skeletal muscle. Alternatives to intramuscular administration include, but are not limited to: intradermal, intranasal, intraocular, subcutaneous, intraperitoneal, intravenous, interstitial, buccal, transdermal, or sublingual administration. Intradermal and intramuscular administration are two preferred routes.

Administration can be achieved in various ways. For instance, injection via a needle (e.g., a hypodermic needle) can be used, particularly for intramuscular, subcutaneous, intraocular, intraperitoneal, or intravenous administration. Needle-free injection can be used as an alternative.

Intramuscular injection is the preferred way of administering RNA according to the invention. Injection into the upper arm, deltoid, or thigh muscle (e.g., anterolateral thigh) is typical.

The administration site can include both immune cells (such as macrophages, e.g., bone marrow derived macrophages), dendritic cells (e.g., bone marrow derived plasmacytoid dendritic cells and/or bone marrow derived myeloid dendritic cells), monocytes (e.g., human peripheral blood monocytes), etc.) and non-immune cells (such as muscle cells, which may be multinucleated and may be arranged into fascicles, and/or fibroblasts). The immune cells can be present at the time of administration but will usually infiltrate the site after administration. For example, the tissue damage caused by invasive administration (e.g., caused by a needle at the administration site) can cause immune cells to infiltrate the damaged area.

RNA enters the cytoplasm of the immune cells and/or the non-immune cells. Entry can be via endocytosis. Inside the endosomes of immune cells the RNA can bind to TLR7 (ssRNA), TLR8 (ssRNA), or TLR3 (dsRNA), thereby triggering innate immune pathways. When RNA escapes from the endosomes into the cytoplasm of immune and non-immune cells, it can bind to RNA helicases (e.g., in the RIG-I-like receptor family, i.e., RLRs) such as RIG-I (RLR-1), MDA5 (RLR-2), and/or LGP2 (RLR-3), also triggering innate immune pathways. The RNA can also be translated in the immune and/or non-immune cells, leading to expression of the immunogen, and ultimately to presentation of the expressed immunogen via the MHC system. The cells can also secrete type I interferons and/or pro-inflammatory cytokines to provide a local adjuvant effect.

The RNA can be delivered as naked RNA (e.g., merely as an aqueous solution of RNA), but to enhance both entry to immune and non-immune cells and also subsequent intercellular effects, and also to reduce the amount of RNA required for a good immunogenic effect, the RNA is preferably administered in combination with a delivery system, such as a particulate or emulsion delivery system. Three useful delivery systems of interest are: (i) liposomes, (ii) non-toxic and biodegradable polymer microparticles, (iii) cationic submicron oil-in-water emulsions. Liposomes are a preferred delivery system.

According to a first aspect of the invention, RNA encoding an immunogen is delivered to a large mammal at a dose of between 2 μg and 100 μg. For instance, the dose can be between 5 μg and 75 μg, between 6 μg and 50 g, between 7 μg and 25 μg, between 8 μg and 20 μg, or between 9 μg and 15 μg. Specific doses can be 5 μg, 6 μg, 7 μg, 8 μg, 9 μg, 10 μg, 11 μg, 12 μg, 13 μg, 14 μg, 15 μg, 20 μg, 25 μg, 30 μg, 35 μg, 40 μg, 45 μg, 50 μg, 60 μg, 70 μg, 80 μg, 90 μg, or 100 μg. A human dose may be 5-10 μg.

According to a second aspect of the invention, RNA encoding an immunogen is delivered to a large mammal at a dose of between 0.1 μg RNA per kg of body weight to 1.5 μg RNA per kg of body weight. For instance, the dose can be between 0.2 μg/kg to 1.2 μg/kg, between 0.3 μg/kg to 1.1 μg/kg, between 0.4 μg/kg to 1.0 μg/kg, between 0.5 μg/kg to 1.0 μg/kg, or between 0.5 μg/kg to 1.5 μg/kg. Specific doses can be 0.1 μg/kg, 0.15 μg/kg, 0.2 μg/kg, 0.25 μg/kg, 0.3 μg/kg, 0.4 μg/kg, 0.5 μg/kg, 1 μg/kg, or 1.2 μg/kg.

Liposomes

Various amphiphilic lipids can form bilayers in an aqueous environment to encapsulate a RNA-containing aqueous core as a liposome. These lipids can have an anionic, cationic or zwitterionic hydrophilic head group. Formation of liposomes from anionic phospholipids dates back to the 1960s, and cationic liposome-forming lipids have been studied since the 1990s. Some phospholipids are anionic whereas other are zwitterionic and others are cationic. Suitable classes of phospholipid include, but are not limited to, phosphatidylethanolamines, phosphatidylcholines, phosphatidylserines, and phosphatidyl-glycerols, and some useful phospholipids are listed in Table 1. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethy1-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC, and dodecylphosphocholine. The lipids can be saturated or unsaturated. The use of at least one unsaturated lipid for preparing liposomes is preferred. If an unsaturated lipid has two tails, both tails can be unsaturated, or it can have one saturated tail and one unsaturated tail.

Liposomes can be formed from a single lipid or from a mixture of lipids. A mixture may comprise: (i) a mixture of anionic lipids, (ii) a mixture of cationic lipids, (iii) a mixture of zwitterionic lipids, (iv) a mixture of anionic lipids and cationic lipids, (v) a mixture of anionic lipids and zwitterionic lipids, (vi) a mixture of zwitterionic lipids and cationic lipids, or (vii) a mixture of anionic lipids, cationic lipids, and zwitterionic lipids. Similarly, a mixture may comprise both saturated and unsaturated lipids. For example, a mixture may comprise DSPC (zwitterionic, saturated), DlinDMA (cationic, unsaturated), and/or DMG (anionic, saturated). Where a mixture of lipids is used, not all of the component lipids in the mixture need to be amphiphilic; e.g., one or more amphiphilic lipids can be mixed with cholesterol.

The hydrophilic portion of a lipid can be PEGylated (i.e., modified by covalent attachment of a polyethylene glycol). This modification can increase stability and prevent non-specific adsorption of the liposomes. For instance, lipids can be conjugated to PEG using techniques such as those disclosed in references 6 and 7. Various lengths of PEG can be used, e.g., between 0.5-8 kDa.

A mixture of DSPC, DlinDMA, PEG-DMG, and cholesterol is used in the examples.

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter ≤50 nm, and LUVs have a diameter >50 nm. Liposomes useful with and of the invention are ideally LUVs with a diameter in the range of 50-220 nm. For a composition comprising a population of LUVs with different diameters: (i) at least 80% by number should have diameters in the range of 20-220 nm, (ii) the average diameter (Zav, by intensity) of the population is ideally in the range of 40-200 nm, and/or (iii) the diameters should have a polydispersity index <0.2. The liposome/RNA complexes of reference 1 are expected to have a diameter in the range of 600-800 nm and to have a high polydispersity.

Techniques for preparing suitable liposomes are well known in the art, e.g., see references 8 to 10. One useful method is described in reference 11 and involves mixing (i) an ethanolic solution of the lipids, (ii) an aqueous solution of the nucleic acid, and (iii) buffer, followed by mixing, equilibration, dilution, and purification. Preferred liposomes of the invention are obtainable by this mixing process.

RNA is preferably encapsulated within the liposomes, and so the liposome forms an outer layer around an aqueous RNA-containing core. This encapsulation has been found to protect RNA from RNase digestion. The liposomes can include some external RNA (e.g., on the surface of the liposomes), but at least half of the RNA (and ideally all of it) is encapsulated.

Polymeric Microparticles

Various polymers can form microparticles to encapsulate or adsorb RNA. The use of a substantially non-toxic polymer means that a recipient can safely receive the particles, and the use of a biodegradable polymer means that the particles can be metabolized after delivery to avoid long-term persistence. Useful polymers are also sterilizable, to assist in preparing pharmaceutical grade formulations.

Suitable non-toxic and biodegradable polymers include, but are not limited to, poly(α-hydroxy acids), polyhydroxy butyric acids, polylactones (including polycaprolactones), polydioxanones, polyvalerolactone, polyorthoesters, polyanhydrides, polycyanoacrylates, tyrosine-derived polycarbonates, polyvinyl-pyrrolidinones or polyester-amides, and combinations thereof.

In some embodiments, the microparticles are formed from poly(α-hydroxy acids), such as a poly(lactides) ("PLA"), copolymers of lactide and glycolide such as a poly(D,L-lactide-co-glycolide) ("PLG"), and copolymers of D,L-lactide and caprolactone. Useful PLG polymers include those having a lactide/glycolide molar ratio ranging, for example, from 20:80 to 80:20, e.g., 25:75, 40:60, 45:55, 50:50, 55:45, 60:40, 75:25. Useful PLG polymers include those having a molecular weight between, for example, 5,000-200,000 Da, e.g., between 10,000-100,000, 20,000-70,000, 30,000-40,000, 40,000-50,000 Da.

The microparticles ideally have a diameter in the range of 0.02 μm to 8 μm. For a composition comprising a population of microparticles with different diameters at least 80% by number should have diameters in the range of 0.03-7 μm.

Techniques for preparing suitable microparticles are well known in the art; e.g., see references 10, 12 (in particular chapter 7), and 13. To facilitate adsorption of RNA, a microparticle may include a cationic surfactant and/or lipid, e.g., as disclosed in references 14 & 15. An alternative way of making polymeric microparticles is by molding and curing, e.g., as disclosed in reference 16.

Microparticles of the invention can have a zeta potential of between 40-100 mV.

One advantage of microparticles over liposomes is that they are readily lyophilized for stable storage.

RNA can be adsorbed to the microparticles, and adsorption is facilitated by including cationic materials (e.g., cationic lipids) in the microparticle.

Oil-In-Water Cationic Emulsions

Oil-in-water emulsions are known for adjuvanting influenza vaccines, e.g., the MF59™ adjuvant in the FLUAD™ product, and the AS03 adjuvant in the PREPANDRIX™ product. RNA delivery according to the present invention can utilize an oil-in-water emulsion, provided that the emulsion includes one or more cationic molecules. For instance, a cationic lipid can be included in the emulsion to provide a positive droplet surface to which negatively-charged RNA can attach.

The emulsion comprises one or more oils. Suitable oil(s) include those from, for example, an animal (such as fish) or a vegetable source. The oil is ideally biodegradable (metabolizable) and biocompatible. Sources for vegetable oils include nuts, seeds, and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil, and the like. In the grain group, corn oil is the most readily available, but the oil of other cereal grains such as wheat, oats, rye, rice, teff, triticale, and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification, and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Preferred emulsions comprise squalene, a shark liver oil which is a branched, unsaturated terpenoid ($C_{30}H_{50}$; [$(CH_3)_2C$[=$CHCH_2CH_2C(CH_3)$]$_2$=$CHCH_2$-]$_2$; 2,6,10,15,19,23-hexamethyl-2,6,10,14,18,22-tetracosahexaene; CAS RN 7683-64-9). Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil phase of an emulsion includes a tocopherol, any of the α-, β-, γ-, δ-, ε-, or ξ-tocopherols can be used, but α-tocopherols are preferred. D-α-tocopherol and DL-α-tocopherol can both be used. A preferred α-tocopherol is DL-α-tocopherol. An oil combination comprising squalene and a tocopherol (e.g., DL-α-tocopherol) can be used.

The oil in the emulsion may comprise a combination of oils, e.g., squalene and at least one further oil.

The aqueous component of the emulsion can be plain water (e.g., w.f.i.) or can include further components, e.g., solutes. For instance, it may include salts to form a buffer, e.g., citrate or phosphate salts, such as sodium salts. Typical buffers include: a phosphate buffer; a Tris buffer; a borate buffer; a succinate buffer; a histidine buffer; or a citrate buffer. A buffered aqueous phase is preferred, and buffers will typically be included in the 5-20 mM range.

The emulsion also includes a cationic lipid. Preferably this lipid is a surfactant so that it can facilitate formation and stabilization of the emulsion. Useful cationic lipids generally contain a nitrogen atom that is positively charged under physiological conditions, e.g., as a tertiary or quaternary amine. This nitrogen can be in the hydrophilic head group of an amphiphilic surfactant. Useful cationic lipids include, but are not limited to: 1,2-dioleoyloxy-3-(trimethylammonio) propane (DOTAP), 3'[N—(N',N'-Dimethylaminoethane)-carbamoyl]Cholesterol (DC Cholesterol), dimethyldioctadecyl-ammonium (DDA, e.g., the bromide), 1,2-Dimyristoyl-3-Trimethyl-AmmoniumPropane (DMTAP), dipalmitoyl(C16:0)trimethyl ammonium propane (DPTAP), distearoyltrimethylammonium propane (DSTAP). Other useful cationic lipids are: benzalkonium chloride (BAK), benzethonium chloride, cetramide (which contains tetradecyltrimethylammonium bromide and possibly small amounts of dedecyltrimethylammonium bromide and hexadecyltrimethyl ammonium bromide), cetylpyridinium chloride (CPC), cetyl trimethylammonium chloride (CTAC), N,N',N'-polyoxyethylene (10)-N-tallow-1,3-diaminopropane, dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N,trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate, N-alkyl pyridinium salts (e.g., cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L (or D)-lysine conjugated to N-glutarylphosphatidylethanolamine, didodecyl glutamate ester with pendant amino group ($C_{12}GluPhC_n$, $N^+$), ditetradecyl glutamate ester with pendant amino group ($C_{12}GluPhC_n,N^+$), cationic derivatives of cholesterol, including but not limited to cholesteryl-3 β-oxysuccinamidoethylenetrimethylammonium salt, cholesteryl-3 β-oxysuccinamidoethylene-dimethylamine, cholesteryl-3 β-carboxyamidoethylenetrimethylammonium salt, and cholesteryl-3 β-carboxyamidoethylenedimethylamine. Other useful cationic lipids are described in refs. 17 & 18.

The cationic lipid is preferably biodegradable (metabolizable) and biocompatible.

In addition to the oil and cationic lipid, an emulsion can include a non-ionic surfactant and/or a zwitterionic surfactant. Such surfactants include, but are not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl, and oleyl alcohols (known as Brij surfactants), such as triethyleneglycol monolauryl ether (Brij 30); polyoxyethylene-9-lauryl ether; and sorbitan esters (commonly known as the Spans), such as sorbitan trioleate (Span 85) and sorbitan monolaurate. Preferred surfactants for including in the emulsion are polysorbate 80 (Tween 80; polyoxyethylene sorbitan monooleate), Span 85 (sorbitan trioleate), lecithin, and Triton X-100.

Mixtures of these surfactants can be included in the emulsion, e.g., Tween 80/Span 85 mixtures, or Tween 80/Triton-X100 mixtures. A combination of a polyoxyethylene sorbitan ester such as polyoxyethylene sorbitan monooleate (Tween 80) and an octoxynol such as t-octylphenoxy-polyethoxyethanol (Triton X-100) is also suitable. Another useful combination comprises laureth 9 plus a polyoxyethylene sorbitan ester and/or an octoxynol. Useful mixtures can comprise a surfactant with a HLB value in the range of 10-20 (e.g., polysorbate 80, with a HLB of 15.0) and a surfactant with a HLB value in the range of 1-10 (e.g., sorbitan trioleate, with a HLB of 1.8).

Preferred amounts of oil (% by volume) in the final emulsion are between 2-20%, e.g., 5-15%, 6-14%, 7-13%, 8-12%. A squalene content of about 4-6% or about 9-11% is particularly useful.

Preferred amounts of surfactants (% by weight) in the final emulsion are between 0.001% and 8%. For example: polyoxyethylene sorbitan esters (such as polysorbate 80) 0.2 to 4%, in particular between 0.4-0.6%, between 0.45-0.55%, about 0.5% or between 1.5-2%, between 1.8-2.2%, between 1.9-2.1%, about 2%, or 0.85-0.95%, or about 1%; sorbitan esters (such as sorbitan trioleate) 0.02 to 2%, in particular about 0.5% or about 1%; octyl- or nonylphenoxy polyoxyethanols (such as Triton X-100) 0.001 to 0.1%, in particular 0.005 to 0.02%; polyoxyethylene ethers (such as laureth 9) 0.1 to 8%, preferably 0.1 to 10% and in particular 0.1 to 1% or about 0.5%.

The absolute amounts of oil and surfactant, and their ratio, can be varied within wide limits while still forming an emulsion. A skilled person can easily vary the relative proportions of the components to obtain a desired emulsion, but a weight ratio of between 4:1 and 5:1 for oil and surfactant is typical (excess oil).

An important parameter for ensuring immunostimulatory activity of an emulsion, particularly in large animals, is the oil droplet size (diameter). The most effective emulsions have a droplet size in the submicron range. Suitably the droplet sizes will be in the range 50-750 nm. Most usefully the average droplet size is less than 250 nm, e.g., less than 200 nm, less than 150 nm. The average droplet size is usefully in the range of 80-180 nm. Ideally, at least 80% (by number) of the emulsion's oil droplets are less than 250 nm in diameter, and preferably at least 90%. Apparatuses for determining the average droplet size in an emulsion, and the size distribution, are commercially available. These typically use the techniques of dynamic light scattering and/or single-particle optical sensing, e.g., the ACCUSIZER™ and NICOMP™ series of instruments available from Particle Sizing Systems (Santa Barbara, USA), or the ZETASIZER™ instruments from Malvern Instruments (UK), or the Particle Size Distribution Analyzer instruments from Horiba (Kyoto, Japan).

Ideally, the distribution of droplet sizes (by number) has only one maximum, i.e., there is a single population of droplets distributed around an average (mode), rather than having two maxima. Preferred emulsions have a polydispersity of <0.4, e.g., 0.3, 0.2, or less.

Suitable emulsions with submicron droplets and a narrow size distribution can be obtained by the use of microfluidization. This technique reduces average oil droplet size by propelling streams of input components through geometrically fixed channels at high pressure and high velocity. These streams contact channel walls, chamber walls, and each other. The results shear, impact, and cavitation forces cause a reduction in droplet size. Repeated steps of microfluidization can be performed until an emulsion with a desired droplet size average and distribution are achieved.

As an alternative to microfluidization, thermal methods can be used to cause phase inversion, as disclosed in reference 19. These methods can also provide a submicron emulsion with a tight particle size distribution.

Preferred emulsions can be filter sterilized, i.e., their droplets can pass through a 220 nm filter. As well as providing a sterilization, this procedure also removes any large droplets in the emulsion.

In certain embodiments, the cationic lipid in the emulsion is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc. In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml, or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc. In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml. In an exemplary embodiment, the cationic oil-in-water emulsion comprises from about 0.73 mg/ml to about 1.45 mg/ml DDA, such as 1.45 mg/ml.

Certain preferred compositions of the invention for administration to a patient comprise squalene, span 85, polysorbate 80, and DOTAP. For instance: squalene may be present at 5-15 mg/m1; span 85 may be present at 0.5-2 mg/m1; polysorbate 80 may be present at 0.5-2 mg/ml; and DOTAP may be present at 0.1-10 mg/ml. The emulsion can include the same amount (by volume) of span 85 and polysorbate 80. The emulsion can include more squalene than surfactant. The emulsion can include more squalene than DOTAP.

The RNA

The invention involves in vivo delivery of RNA which encodes an immunogen. The RNA can trigger innate immunity pathways and is also translated, leading to expression of the immunogen.

The RNA is +-stranded, and so it can be translated without needing any intervening replication steps such as reverse transcription.

Preferred +-stranded RNAs are self-replicating. A self-replicating RNA molecule (replicon) can, when delivered to a mammalian cell even without any proteins, lead to the production of multiple daughter RNAs by transcription from itself (via an antisense copy which it generates from itself). A self-replicating RNA molecule is thus typically a +-strand molecule which can be directly translated after delivery to a cell, and this translation provides a RNA-dependent RNA polymerase which then produces both antisense and sense transcripts from the delivered RNA. Thus, the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall results of this sequence of transcriptions is a huge amplification in the number of the introduced replicon RNAs and so the encoded immunogen becomes a major polypeptide product of the cells.

One suitable system for achieving self-replication is to use an alphavirus-based RNA replicon. These +-stranded replicons are translated after delivery to a cell to give of a replicase (or replicase-transcriptase). The replicase is translated as a polyprotein which auto-cleaves to provide a replication complex which creates genomic −-strand copies of the +-strand delivered RNA. These −-strand transcripts can themselves be transcribed to give further copies of the +-stranded parent RNA and also to give a subgenomic transcript which encodes the immunogen. Translation of the subgenomic transcript thus leads to in situ expression of the immunogen by the infected cell. Suitable alphavirus replicons can use a replicase from a Sindbis virus, a Semliki Forest virus, an eastern equine encephalitis virus, a Venezuelan equine encephalitis virus (VEEV), etc. Mutant or wild-type viruses sequences can be used, e.g., the attenuated TC83 mutant of VEEV has been used in replicons (see reference [20]).

A preferred self-replicating RNA molecule thus encodes (i) a RNA-dependent RNA polymerase which can transcribe RNA from the self-replicating RNA molecule and (ii) an immunogen. The polymerase can be an alphavirus replicase, e.g., comprising one or more of alphavirus proteins nsP1, nsP2, nsP3 and nsP4.

Whereas natural alphavirus genomes encode structural virion proteins in addition to the non-structural replicase polyprotein, it is preferred that a self-replicating RNA molecule of the invention does not encode alphavirus structural proteins. Thus, a preferred self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins.

Thus, a self-replicating RNA molecule useful with the invention may have two open reading frames. The first (5') open reading frame encodes a replicase; the second (3') open reading frame encodes an immunogen. In some embodiments the RNA may have additional (e.g., downstream) open reading frames, e.g., to encode further immunogens (see below) or to encode accessory polypeptides.

A self-replicating RNA molecule can have a 5' sequence which is compatible with the encoded replicase.

Self-replicating RNA molecules can have various lengths, but they are typically 5000-25000 nucleotides long, e.g., 8000-15000 nucleotides, or 9000-12000 nucleotides. Thus, the RNA is longer than seen in siRNA delivery.

A RNA molecule useful with the invention may have a 5' cap (e.g., a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding.

A RNA molecule may have a 3' poly-A tail. It may also include a poly-A polymerase recognition sequence (e.g., AAUAAA) near its 3' end.

A RNA molecule useful with the invention will typically be single-stranded. Single-stranded RNAs can generally initiate an adjuvant effect by binding to TLR7, TLR8, RNA helicases, and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

A RNA molecule useful with the invention can conveniently be prepared by in vitro transcription (IVT). IVT can use a (cDNA) template created and propagated in plasmid form in bacteria or created synthetically (for example, by gene synthesis and/or polymerase chain-reaction (PCR) engineering methods). For instance, a DNA-dependent RNA polymerase (such as the bacteriophage T7, T3, or SP6 RNA polymerases) can be used to transcribe the RNA from a DNA template.

Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

As discussed in reference 21, the self-replicating RNA can include (in addition to any 5' cap structure) one or more nucleotides having a modified nucleobase. Thus, the RNA can comprise m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2'-O-methyladenosine); ms2-m6A (2-methylthio-N6-methyladenosine); i6A (N6-isopentenyladenosine); ms2i6A (2-methylthio-N6-isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4-acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyluridine); ncm5Um (5-carbamoylmethyl-2'-O-methyluridine); cmnm5U (5-carboxymethylaminomethyluridine); cnmm5Um (5-carboxymethylaminomethyl-2-L-O-methyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O- dimethylcytidine); hm5C (5-hydroxymethylcytidine); m3U (3-methyluridine); cm5U (5-carboxymethyluridine); m6Am (N6,T-O-dimethyladenosine); m62Am (N6,N6,O-2-trimethyladenosine); m2'7G (N2,7-dimethylguanosine); m2'2'7G (N2,N2,7-trimethylguanosine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine); irinomethyluridine; tm5s2U (S-taurinomethyl-2-thiouridine)); imG-14 (4-demethyl guanosine); imG2 (isoguanosine); or ac6A (N6-acetyladenine), hypoxanthine, inosine, 8-oxo-adenine, 7-substituted derivatives thereof, dihydrouracil, pseudouracil, 2-thiouracil, 4-thiouracil, 5-aminouracil, 5-(C1-C6)-alkyluracil, 5-methyluracil, 5-(C2-C6)-alkenyluracil, 5-(C2-C6)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, or an abasic nucleotide. For instance, a self-replicating RNA can include one or more modified pyrimidine nucleobases, such as pseudouridine and/or 5-methylcytosine residues. In some embodiments, however, the RNA includes no modified nucleobases, and may include no modified nucleotides; i.e., all of the nucleotides in the RNA are standard A, C, G, and U ribonucleotides (except for any 5' cap structure, which may include a 7-methylguanosine). In other embodiments, the RNA may include a 5' cap comprising a 7-methylguanosine, and the first 1, 2, or 3 5' ribonucleotides may be methylated at the 2' position of the ribose.

A RNA used with the invention ideally includes only phosphodiester linkages between nucleosides, but in some embodiments, it can contain phosphoramidate, phosphorothioate, and/or methylphosphonate linkages. Ideally, administered RNA includes fewer than 10 different species of RNA, e.g., 5, 4, 3, or 2 different species; most preferably, a composition includes a single RNA species; i.e., all RNA molecules in the composition (e.g., within a liposome) have the same sequence and same length.

The Immunogen

RNA molecules used with the invention encode a polypeptide immunogen. After administration of the RNA, the immunogen is translated in vivo and can elicit an immune response in the recipient. The immunogen may elicit an immune response against a bacterium, a virus, a fungus, or a parasite (or, in some embodiments, against an allergen; and in other embodiments, against a tumor antigen). The immune response may comprise an antibody response (usually including IgG) and/or a cell-mediated immune response. The polypeptide immunogen will typically elicit an immune response which recognizes the corresponding bacterial, viral, fungal, or parasite (or allergen or tumor) polypeptide, but in some embodiments the polypeptide may act as a mimotope to elicit an immune response which recognizes a bacterial, viral, fungal, or parasite saccharide. The immunogen will typically be a surface polypeptide, e.g., an adhesin, a hemagglutinin, an envelope glycoprotein, a spike glycoprotein, etc.

RNA molecules can encode a single polypeptide immunogen or multiple polypeptides. Multiple immunogens can be presented as a single polypeptide immunogen (fusion polypeptide) or as separate polypeptides. If immunogens are expressed as separate polypeptides, then one or more of these may be provided with an upstream IRES or an additional viral promoter element. Alternatively, multiple immunogens may be expressed from a polyprotein that encodes individual immunogens fused to a short autocatalytic protease (e.g., foot-and-mouth disease virus 2A protein), or as inteins.

Unlike references 1 and 22, the RNA encodes an immunogen. For the avoidance of doubt, the invention does not encompass RNA that encodes a firefly luciferase or that encodes a fusion protein of E. coli β-galactosidase or that encodes a green fluorescent protein (GFP). Also, the RNA is not total mouse thymus RNA.

In some embodiments the immunogen elicits an immune response against one of these bacteria:

Neisseria meningitidis: useful immunogens include, but are not limited to, membrane proteins such as adhesins, autotransporters, toxins, iron acquisition proteins, and factor H binding protein. A combination of three useful polypeptides is disclosed in reference 23.

Streptococcus pneumoniae: useful polypeptide immunogens are disclosed in reference 24. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

Streptococcus pyogenes: useful immunogens include, but are not limited to, the polypeptides disclosed in references 25 and 26.

Moraxella catarrhalis.

Bordetella pertussis: Useful pertussis immunogens include, but are not limited to, pertussis toxin or toxoid (PT), filamentous haemagglutinin (FHA), pertactin, and agglutinogens 2 and 3.

Staphylococcus aureus: Useful immunogens include, but are not limited to, the polypeptides disclosed in reference 27, such as a hemolysin, esxA, esxB, ferrichrome-binding protein (sta006), and/or the sta011 lipoprotein.

Clostridium tetani: the typical immunogen is tetanus toxoid.

Cornynebacterium diphtheriae: the typical immunogen is diphtheria toxoid.

Haemophilus influenzae: Useful immunogens include, but are not limited to, the polypeptides disclosed in references 28 and 29.

Pseudomonas aeruginosa

Streptococcus agalactiae: useful immunogens include, but are not limited to, the polypeptides disclosed in reference 25.

Chlamydia trachomatis: Useful immunogens include, but are not limited to, PepA, LcrE, ArtJ, DnaK, CT398, OmpH-like, L7/L12, OmcA, AtoS, CT547, Eno, HtrA, and MurG (e.g., as disclosed in reference 30. LcrE (see reference [31]) and HtrA (see reference [32]) are two preferred immunogens.

Chlamydia pneumoniae: Useful immunogens include, but are not limited to, the polypeptides disclosed in reference 33.

Helicobacter pylori: Useful immunogens include, but are not limited to, CagA, VacA, NAP, and/or urease (see reference [34]).

Escherichia coli: Useful immunogens include, but are not limited to, immunogens derived from enterotoxigenic E. coli (ETEC), enteroaggregative E. coli (EAggEC), diffusely adhering *E. coli* (DAEC), enteropathogenic *E. coli* (EPEC), extraintestinal pathogenic *E. coli* (ExPEC), and/or enterohemorrhagic *E. coli* (EHEC). ExPEC strains include uropathogenic *E. coli* (UPEC) and meningitis/sepsis-associated *E. coli* (MNEC). Useful UPEC polypeptide immunogens are disclosed in references 35 and 36. Useful MNEC immunogens are disclosed in reference 37. A useful immunogen for several *E. coli* types is AcfD (see reference [38]).

*Bacillus anthracis*

*Yersinia pestis*: Useful immunogens include, but are not limited to, those disclosed in references 39 and 40.

*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In some embodiments the immunogen elicits an immune response against one of these viruses:

Orthomyxovirus: Useful immunogens can be from an influenza A, B, or C virus, such as the hemagglutinin, neuraminidase, or matrix M2 proteins. Where the immunogen is an influenza A virus hemagglutinin it may be from any subtype, e.g., H1, H2, H3, H4, H5, H6, H7, H8, H9, H10, H11, H12, H13, H14, H15, or H16.

Paramyxoviridae viruses: Viral immunogens include, but are not limited to, those derived from Pneumoviruses (e.g., respiratory syncytial virus, RSV), Rubulaviruses (e.g., mumps virus), Paramyxoviruses (e.g., parainfluenza virus), Metapneumoviruses and Morbilliviruses (e.g., measles virus).

Poxviridae: Viral immunogens include, but are not limited to, those derived from Orthopoxvirus such as *Variola vera*, including but not limited to, *Variola major* and *Variola minor.*

Picornavirus: Viral immunogens include, but are not limited to, those derived from Picornaviruses, such as Enteroviruses, Rhinoviruses, Heparnavirus, Cardioviruses, and Aphthoviruses. In one embodiment, the enterovirus is a poliovirus, e.g., a type 1, type 2, and/or type 3 poliovirus. In another embodiment, the enterovirus is an EV71 enterovirus. In another embodiment, the enterovirus is a coxsackie A or B virus.

Bunyavirus: Viral immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: Viral immunogens include, but are not limited to, those derived from a Heparnavirus, such as hepatitis A virus (HAV).

Filovirus: Viral immunogens include, but are not limited to, those derived from a filovirus, such as an Ebola virus (including a Zaire, Ivory Coast, Reston, or Sudan ebolavirus) or a Marburg virus.

Togavirus: Viral immunogens include, but are not limited to, those derived from a Togavirus, such as a Rubivirus, an Alphavirus, or an Arterivirus. This includes rubella virus.

Flavivirus: Viral immunogens include, but are not limited to, those derived from a Flavivirus, such as Tick-borne encephalitis (TBE) virus, Dengue (types 1, 2, 3, or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: Viral immunogens include, but are not limited to, those derived from a Pestivirus, such as Bovine viral diarrhea (BVDV), Classical swine fever (CSFV), or Border disease (BDV).

Hepadnavirus: Viral immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: Viral immunogens include, but are not limited to, those derived from a Rhabdovirus, such as a Lyssavirus (e.g., a Rabies virus) and Vesiculovirus (VSV).

Caliciviridae: Viral immunogens include, but are not limited to, those derived from Calciviridae, such as Norwalk virus (Norovirus), and Norwalk-like Viruses, such as Hawaii Virus and Snow Mountain Virus.

Coronavirus: Viral immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: Viral immunogens include, but are not limited to, those derived from an Oncovirus, a Lentivirus (e.g., HIV-1 or HIV-2), or a Spumavirus.

Reovirus: Viral immunogens include, but are not limited to, those derived from an Orthoreovirus, a Rotavirus, an Orbivirus, or a Coltivirus.

Parvovirus: Viral immunogens include, but are not limited to, those derived from Parvovirus B19.

Herpesvirus: Viral immunogens include, but are not limited to, those derived from a human herpesvirus, such as, by way of example only, Herpes Simplex Viruses (HSV) (e.g., HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: Viral immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63, or 65, e.g., from one or more of serotypes 6, 11, 16, and/or 18.

Adenovirus: Viral immunogens include those derived from adenovirus serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of Atlantic salmon), landlocked salmon virus (LSV), Atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: Epidermophytonfloccusum, *Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon spp., Septata intestinalis* and *Enterocytozoon bieneusi*; the less common are *Brachiola* spp., *Microsporidium* spp., *Nosema* spp., *Pleistophora* spp., *Trachipleistophora* spp., *Vittaforma* spp., *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

In some embodiments, the immunogen elicits an immune response against a parasite from the *Plasmodium* genus, such as *P. falciparum, P. vivax, P. malariae*, or *P. ovale*. Thus, the invention may be used for immunizing against malaria. In some embodiments the immunogen elicits an immune response against a parasite from the Caligidae family, particularly those from the *Lepeophtheirus* and *Caligus* genera, e.g., sea lice such as *Lepeophtheirus salmonis* or *Caligus rogercresseyi*.

In some embodiments, the immunogen elicits an immune response against: pollen allergens (tree-, herb-, weed-, and grass-pollen allergens); insect or arachnid allergens (inhalant, saliva, and venom allergens, e.g., mite allergens, cockroach, and midges allergens, hymenoptera venom allergens); animal hair and dandruff allergens (from, e.g., dog, cat, horse, rat, mouse, etc.); and food allergens (e.g., a gliadin). Important pollen allergens from trees, grasses, and herbs are such originating from the taxonomic orders of Fagales, Oleales, Pinales, and platanaceae including, but not limited to, birch (*Betula*), alder (*Alnus*), hazel (*Corylus*), hornbeam (*Carpinus*), and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and *Sorghum*, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite, e.g., *Lepidoglyphys, Glycyphagus*, and *Tyrophagus*, those from cockroaches, midges, and fleas, e.g., *Blatella, Periplaneta, Chironomus*, and *Ctenocepphalides*, and those from mammals such as cat, dog, and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE, and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer, and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) overexpressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung, and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1, and tyrosinase related protein-2/TRP2 (associated with, e.g., melanoma); (e) prostate associated antigens such as PAP, PSA, PSMA, PSH-P1, PSM-P1, PSM-P2, associated with, e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

RNA will be administered as a component in a pharmaceutical composition for immunizing subjects against various diseases. These compositions will typically include a pharmaceutically acceptable carrier in addition to the RNA, often as part of a delivery system as described above. A thorough discussion of pharmaceutically acceptable carriers is available in reference 41.

A pharmaceutical composition of the invention may include one or more small molecule immunopotentiators. For example, the composition may include a TLR2 agonist (e.g., Pam3CSK4), a TLR4 agonist (e.g., an aminoalkyl glucosaminide phosphate, such as E6020), a TLR7 agonist (e.g., imiquimod), a TLR8 agonist (e.g., resiquimod), and/or a TLR9 agonist (e.g., IC31). Any such agonist ideally has a molecular weight of <2000 Da. Where a RNA is encapsulated, in some embodiments such agonist(s) are also encapsulated with the RNA, but in other embodiments they are unencapsulated. Where a RNA is adsorbed to a particle, in some embodiments such agonist(s) are also adsorbed with the RNA, but in other embodiments they are unadsorbed.

Pharmaceutical compositions of the invention may include the particles in plain water (e.g., w.f.i.) or in a buffer, e.g., a phosphate buffer, a Tris buffer, a borate buffer, a succinate buffer, a histidine buffer, or a citrate buffer. Buffer salts will typically be included in the 5-20 mM range.

Pharmaceutical compositions of the invention may have a pH between 5.0 and 9.5, e.g., between 6.0 and 8.0.

Compositions of the invention may include sodium salts (e.g., sodium chloride) to give tonicity. A concentration of 10±2 mg/ml NaCl is typical, e.g., about 9 mg/ml.

Compositions of the invention may include metal ion chelators. These can prolong RNA stability by removing ions which can accelerate phosphodiester hydrolysis. Thus, a composition may include one or more of EDTA, EGTA, BAPTA, pentetic acid, etc. Such chelators are typically present at between 10-500 μM, e.g., 0.1 mM. A citrate salt, such as sodium citrate, can also act as a chelator, while advantageously also providing buffering activity.

Pharmaceutical compositions of the invention may have an osmolality of between 200 mOsm/kg and 400 mOsm/kg, e.g., between 240-360 mOsm/kg, or between 290-310 mOsm/kg.

Pharmaceutical compositions of the invention may include one or more preservatives, such as thiomersal or 2-phenoxyethanol. Mercury-free compositions are preferred, and preservative-free vaccines can be prepared.

Pharmaceutical compositions of the invention are preferably sterile.

Pharmaceutical compositions of the invention are preferably non-pyrogenic, e.g., containing <1 EU (endotoxin unit, a standard measure) per dose, and preferably <0.1 EU per dose.

Pharmaceutical compositions of the invention are preferably gluten free.

Pharmaceutical compositions of the invention may be prepared in unit dose form. In some embodiments a unit dose may have a volume of between 0.1-1.0 ml, e.g., about 0.5 ml.

The compositions may be prepared as injectables, either as solutions or suspensions. The composition may be prepared for pulmonary administration, e.g., by an inhaler, using a fine spray. The composition may be prepared for nasal, aural, or ocular administration, e.g., as spray or drops. Injectables for intramuscular administration are typical.

The RNA content of compositions of the invention is expressed in terms of the amount of RNA per unit dose. RNA is readily quantified using available techniques.

RNAs are not delivered in combination with ribosomes and so pharmaceutical compositions of the invention are ribosome-free.

Methods of Treatment and Medical Uses

RNA delivery according to the invention is for eliciting an immune response in vivo against an immunogen of interest. The immune response is preferably protective and preferably involves antibodies and/or cell-mediated immunity. The method may raise a booster response.

By raising an immune response, the mammal can be protected against various diseases and/or infections, e.g., against bacterial and/or viral diseases as discussed above. RNA-containing compositions are immunogenic and are more preferably vaccine compositions. Vaccines according to the invention may either be prophylactic (i.e., to prevent infection) or therapeutic (i.e., to treat infection) but will typically be prophylactic.

The mammal immunized according to the present invention is a large mammal, such as a human or a large veterinary mammal (e.g., horses, cattle, deer, goats, pigs, camels, antelope, elephants). Where the vaccine is for prophylactic use, the human is preferably a child (e.g., a toddler or infant) or a teenager; where the vaccine is for therapeutic use, the human is preferably a teenager or an adult. A vaccine intended for children may also be administered to adults, e.g., to assess safety, dosage, immunogenicity, etc. Vaccines prepared according to the invention may be used to treat both children and adults. Thus, a human patient may be less than 1 year old, less than 5 years old, 1-5 years old, 5-15 years old, 15-55 years old, or at least 55 years old. Preferred patients for receiving the vaccines are the elderly (e.g., ≥50 years old, ≥60 years old, and preferably ≥65 years), the young (e.g., ≤5 years old), hospitalized patients, healthcare workers, armed service and military personnel, pregnant women, the chronically ill, or immunodeficient patients. The vaccines are not suitable solely for these groups, however, and may be used more generally in a population.

Compositions of the invention will generally be administered directly to a patient. Direct delivery may be accomplished by parenteral injection (e.g., subcutaneously, intraperitoneally, intravenously, intramuscularly, or to the interstitial space of a tissue; unlike reference 1, intraglossal injection is not typically used with the present invention), or mucosally, such as by rectal, oral (e.g., tablet, spray), vaginal, topical, transdermal or transcutaneous, intranasal, ocular, aural, pulmonary, or other mucosal administration. Injection may be via a needle (e.g., a hypodermic needle), but needle-free injection may alternatively be used. A typical intramuscular dose is 0.5 ml.

The invention may be used to elicit systemic and/or mucosal immunity, preferably to elicit an enhanced systemic and/or mucosal immunity.

Dosage can be by a single unit dose schedule or a multiple unit dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.). In one embodiment, unit doses may be administered approximately 6 weeks, 10 weeks, and 14 weeks after birth, e.g., at an age of 6 weeks, 10 weeks, and 14 weeks, as often used in the World Health Organization's Expanded Program on Immunization ("EPI"). In an alternative embodiment, two primary unit doses are administered about two months apart, e.g., about 7, 8, or 9 weeks apart, followed by one or more booster unit doses about 6 months to 1 year after the second primary dose, e.g., about 6, 8, 10, or 12 months after the second primary dose. In a further embodiment, three primary doses are administered about two months apart, e.g., about 7, 8, or 9 weeks apart, followed by one or more booster doses about 6 months to 1 year after the third primary dose, e.g., about 6, 8, 10, or 12 months after the third primary dose.

GENERAL EMBODIMENTS

In some embodiments of the invention, the RNA includes no modified nucleotides (see above). In other embodiments the RNA can optionally include at least one modified nucleotide, provided that one or more of the following features (already disclosed above) is also required:
A. Where the RNA is delivered with a liposome, the liposome comprises DSDMA, DODMA, DLinDMA and/or DLenDMA.
B. Where the RNA is encapsulated in a liposome, the hydrophilic portion of a lipid in the liposome is PEGylated.
C. Where the RNA is encapsulated in a liposome, at least 80% by number of the liposomes have diameters in the range of 20-220 nm.
D. Where the RNA is delivered with a microparticle, the microparticle is a non-toxic and biodegradable polymer microparticle.
E. Where the RNA is delivered with a microparticle, the microparticles have a diameter in the range of 0.02 μm to 8 μm.
F. Where the RNA is delivered with a microparticle, at least 80% by number of the microparticles have a diameter in the range of 0.03-7 μm.
G. Where the RNA is delivered with a microparticle, the composition is lyophilized.
H. Where the RNA is delivered with an emulsion, the emulsion comprises a biodegradable oil (e.g., squalene).
I. Where the RNA is delivered with an emulsion, the emulsion includes one or more cationic molecules, e.g., one or more cationic lipids.
J. The RNA has a 3' poly-A tail, and the immunogen can elicit an immune response in vivo against a bacterium, a virus, a fungus, or a parasite.
K. The RNA is delivered in combination with a metal ion chelator with a delivery system selected from: (i) liposomes, (ii) non-toxic and biodegradable polymer microparticles, (iii) cationic submicron oil-in-water emulsions.

General

The practice of the present invention will employ, unless otherwise indicated, conventional methods of chemistry, biochemistry, molecular biology, immunology, and pharmacology, within the skill of the art. Such techniques are explained fully in the literature. See, e.g., references 42-48, etc.

The term "comprising" encompasses "including" as well as "consisting", e.g., a composition "comprising" X may consist exclusively of X or may include something additional, e.g., X+Y.

The term "about" in relation to a numerical value x is optional and means, for example, x±10%.

The word "substantially" does not exclude "completely", e.g., a composition which is "substantially free" from Y may be completely free from Y. Where necessary, the word "substantially" may be omitted from the definition of the invention.

References to charge, to cations, to anions, to zwitterions, etc., are taken at pH 7.

TLR3 is the Toll-like receptor 3. It is a single membrane-spanning receptor which plays a key role in the innate immune system. Known TLR3 agonists include poly(I:C). "TLR3" is the approved HGNC name for the gene encoding this receptor, and its unique HGNC ID is HGNC:11849. The RefSeq sequence for the human TLR3 gene is GI:2459625.

TLR7 is the Toll-like receptor 7. It is a single membrane-spanning receptor which plays a key role in the innate immune system. Known TLR7 agonists include, e.g., imiquimod. "TLR7" is the approved HGNC name for the gene encoding this receptor, and its unique HGNC ID is HGNC:15631. The RefSeq sequence for the human TLR7 gene is GI:67944638.

TLR8 is the Toll-like receptor 8. It is a single membrane-spanning receptor which plays a key role in the innate immune system. Known TLR8 agonists include, e.g., resiquimod. "TLR8" is the approved HGNC name for the gene encoding this receptor, and its unique HGNC ID is HGNC:15632. The RefSeq sequence for the human TLR8 gene is GI:20302165.

The RIG-I-like receptor ("RLR") family includes various RNA helicases which play key roles in the innate immune system (see reference [49]). RLR-1 (also known as RIG-I or retinoic acid inducible gene I) has two caspase recruitment domains near its N-terminus. The approved HGNC name for the gene encoding the RLR-1 helicase is "DDX58" (for DEAD (Asp-Glu-Ala-Asp) box polypeptide 58) and the unique HGNC ID is HGNC:19102. The RefSeq sequence for the human RLR-1 gene is GI:77732514. RLR-2 (also known as MDA5 or melanoma differentiation-associated gene 5) also has two caspase recruitment domains near its N-terminus. The approved HGNC name for the gene encoding the RLR-2 helicase is "IFIH1" (for interferon induced with helicase C domain 1) and the unique HGNC ID is HGNC:18873. The RefSeq sequence for the human RLR-2 gene is GI: 27886567. RLR-3 (also known as LGP2 or laboratory of genetics and physiology 2) has no caspase recruitment domains. The approved HGNC name for the gene encoding the RLR-3 helicase is "DHX58" (for DEXH (Asp-Glu-X-His) box polypeptide 58) and the unique HGNC ID is HGNC:29517. The RefSeq sequence for the human RLR-3 gene is GI: 149408121.

PKR is a double-stranded RNA-dependent protein kinase. It plays a key role in the innate immune system. "EIF2AK2" (for eukaryotic translation initiation factor 2-alpha kinase 2) is the approved HGNC name for the gene encoding this enzyme, and its unique HGNC ID is HGNC:9437. The RefSeq sequence for the human PKR gene is GI:208431825.

BRIEF DESCRIPTION OF DRAWINGS

FIG. 3 shows protein expression (as relative light units, RLU) at days 1, 3, and 6 after delivery of RNA as a virion-packaged replicon (squares), naked RNA (triangles), or as microparticles (circles).

FIG. 4 shows a gel with stained RNA. Lanes show: (1) markers, (2) naked replicon, (3) replicon encapsulated in liposome, (4) liposome treated with RNase then subjected to phenol/chloroform extraction.

FIGS. 14A & 14B show F-specific IgG titers (mean $\log_{10}$ titers±std dev) over 63 days (FIG. 14A) and 210 days (FIG. 14B) after immunization of calves. The four lines are easily distinguished at day 63 and are, from bottom to top: PBS negative control; liposome-delivered RNA; emulsion-delivered RNA; and the "Triangle 4" product.

MODES FOR CARRYING OUT THE INVENTION

RNA Replicons

Figure 1:
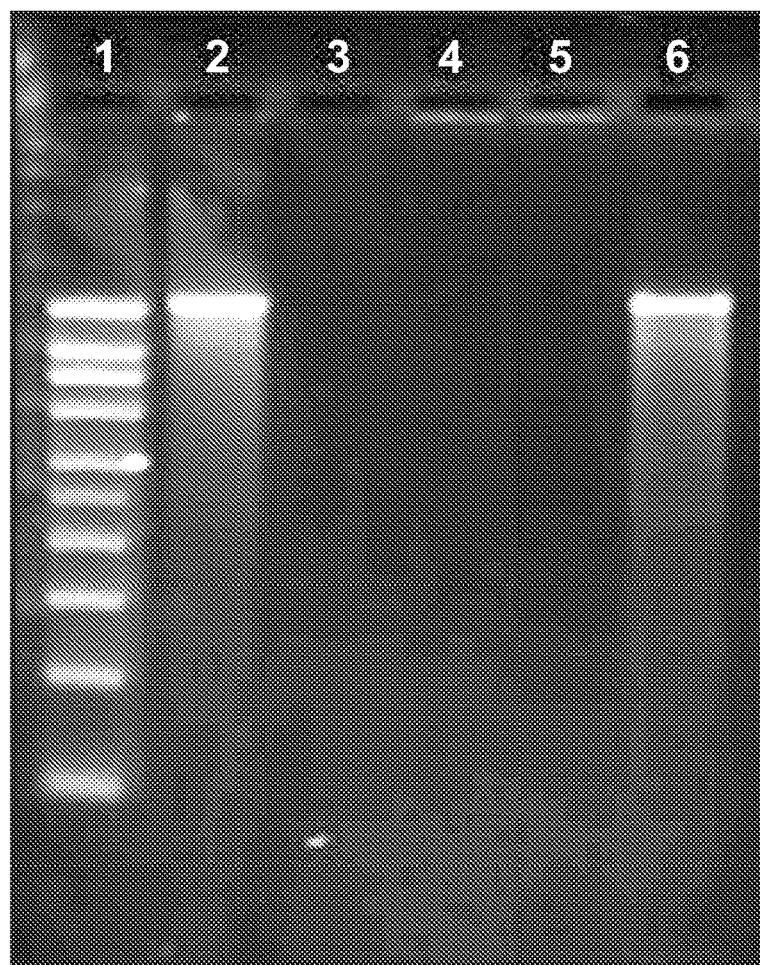
FIG. 1 shows a gel with stained RNA. Lanes show: (1) markers, (2) naked replicon, (3) replicon after RNase treatment, (4) replicon encapsulated in liposome, (5) liposome after RNase treatment, (6) liposome treated with RNase then subjected to phenol/chloroform extraction.

Various replicons are used below. In general, these are based on a hybrid alphavirus genome with non-structural proteins from Venezuelan equine encephalitis virus (VEEV), a packaging signal from Sindbis virus, and a 3' UTR from Sindbis virus or a VEEV mutant. The replicon is about 10 kb long and has a poly-A tail.

Plasmid DNA encoding alphavirus replicons (named: pT7-mVEEV-FL.RSVF or A317; pT7-mVEEV-SEAP or A306; pSP6-VCR-GFP or A50) served as a template for synthesis of RNA in vitro. The replicons contain the alphavirus genetic elements required for RNA replication but lack those encoding gene products necessary for particle assembly; the structural proteins are instead replaced by a protein of interest (either a reporter, such as SEAP or GFP, or an immunogen, such as full-length RSV F protein) and so the replicons are incapable of inducing the generation of infectious particles. A bacteriophage (T7 or SP6) promoter upstream of the alphavirus cDNA facilitates the synthesis of the replicon RNA in vitro and a hepatitis delta virus (HDV) ribozyme immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP, and UTP) following the instructions provided by the manufacturer (Ambion). Following transcription, the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the SCRIPTCAP™ m7G Capping System (Epicentre Biotechnologies) as outlined in the user manual; replicons capped in this way are given the "v" prefix, e.g., vA317 is the A317 replicon capped by VCE. Post-transcriptionally capped RNA was precipitated with LiCl and reconstituted in nuclease-free water. The concentration of the RNA samples was determined by measuring $OD_{260\ nm}$. Integrity of the in vitro transcripts was confirmed by denaturing agarose gel electrophoresis.

PLG Adsorption

Microparticles were made using 500 mg of PLG RG503 (50:50 lactide/glycolide molar ratio, MW ~30 kDa) and 20 mg DOTAP using an Omni Macro Homogenizer. The particle suspension was shaken at 150 rpm overnight and then filtered through a 40 µm sterile filter for storage at 2-8° C. Self-replicating RNA was adsorbed to the particles. To prepare 1 mL of PLG/RNA suspension the required volume of PLG particle suspension was added to a vial and nuclease-free water was added to bring the volume to 900 µL. 100 µL RNA (10 µg/mL) was added dropwise to the PLG suspension, with constant shaking. PLG/RNA was incubated at room temperature for 30 min. For 1 mL of reconstituted suspension, 45 mg mannitol, 15 mg sucrose, and 250-500 µg of PVA were added. The vials were frozen at −80° C. and lyophilized.

To evaluate RNA adsorption, 100 µL particle suspension was centrifuged at 10,000 rpm for 5 min and supernatant was collected. PLG/RNA was reconstituted using 1 mL nuclease-free water. To 100 µL particle suspension (1 µg RNA), 1 mg heparin sulfate was added. The mixture was vortexed and allowed to sit at room temperature for 30 min for RNA desorption. Particle suspension was centrifuged and supernatant was collected.

For RNAse stability, 100 µL particle suspension was incubated with 6.4 mAU of RNase A at room temperature for 30 min. RNAse was inactivated with 0.126 mAU of Proteinase K at 55° C. for 10 min. 1 mg of heparin sulfate was added to desorb the RNA followed by centrifugation. The supernatant samples containing RNA were mixed with formaldehyde load dye, heated at 65° C. for 10 min, and analyzed using a 1% denaturing gel (460 ng RNA loaded per lane).

To assess expression, BALB/c mice were immunized with 1 µg RNA in 100 µL intramuscular injection volume (50 µL/leg) on day 0. Sera were collected on days 1, 3, and 6. Protein expression was determined using a chemiluminescence assay. As shown in FIG. 3, expression was higher when RNA was delivered by PLG (triangles) than without any delivery particle (circles).

Cationic Nanoemulsion

An oil-in-water emulsion was prepared by microfluidizing squalene, span 85, polysorbate 80, and varying amounts of DOTAP. Briefly, oil soluble components (squalene, span 85, cationic lipids, lipid surfactants) were combined in a beaker, lipid components were dissolved in organic solvent. The resulting lipid solution was added directly to the oil phase. The solvent was allowed to evaporate at room temperature for 2 hours in a fume hood prior to combining the aqueous phase and homogenizing the sample to provide a homogeneous feedstock. The primary emulsions were passed three to five times through a MICROFLUIDIZER™ with an ice bath cooling coil. The batch samples were removed from the unit and stored at 4° C.

This emulsion is thus similar to the commercial MF59™ adjuvant, but supplemented by a cationic DOTAP to provide a cationic nanoemulsion ("CNE"). The final composition of emulsion "CNE17" was squalene (4.3% by weight), span 85 (0.5% by weight), polysorbate 80 (0.5% by weight), DOTAP (1.4 mg/ml), in 10 mM citrate buffer, pH 6.5.

RNA adsorbs to the surface of the oil droplets in these cationic emulsions. To adsorb RNA, a RNA solution is diluted to the appropriate concentration in RNase free water and then added directly into an equal volume of emulsion while vortexing lightly. The solution is allowed to sit at room temperature for approximately 2 hours to allow adsorption. The resulting solution is diluted to the required RNA concentration prior to administration.

Liposomal Encapsulation

RNA was encapsulated in liposomes made by the method of references 11 and 50. The liposomes were made of 10% DSPC (zwitterionic), 40% DlinDMA (cationic), 48% cholesterol, and 2% PEG-conjugated DMG (2 kDa PEG). These proportions refer to the % moles in the total liposome.

DlinDMA (1,2-dilinoleyloxy-N,N-dimethyl-3-aminopropane) was synthesized using the procedure of reference 6. DSPC (1,2-diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt), and DC-chol (38-[N—(N',N'-dimethylaminoethane)-carbamoyl]cholesterol hydrochloride) were from Avanti Polar Lipids.

Briefly, lipids were dissolved in ethanol (2 mL), a RNA replicon was dissolved in buffer (2 mL, 100 mM sodium citrate, pH 6), and these were mixed with 2 mL of buffer followed by 1 hour of equilibration. The mixture was diluted with 6 mL buffer then filtered. The resulting product contained liposomes, with ~95% encapsulation efficiency.

For example, in one particular method, fresh lipid stock solutions were prepared in ethanol. 37 mg of DlinDMA, 11.8 mg of DSPC, 27.8 mg of cholesterol, and 8.07 mg of PEG-DMG were weighed and dissolved in 7.55 mL of ethanol. The freshly prepared lipid stock solution was gently rocked at 37° C. for about 15 min to form a homogenous mixture. Then, 755 µL of the stock was added to 1.245 mL ethanol to make a working lipid stock solution of 2 mL. This amount of lipids was used to form liposomes with 250 µg RNA. A 2 mL working solution of RNA was also prepared from a stock solution of ~1 µg/µL in 100 mM citrate buffer (pH 6). Three 20 mL glass vials (with stir bars) were rinsed with RNASE AWAY™ solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3cc LUER-LOK™ syringes. 2 mL citrate buffer (pH 6) was loaded in another 3 cc syringe. Syringes containing RNA and the lipids were connected to a T mixer (PEEK™ 500 µm ID junction, Idex Health Science) using FEP tubing (fluorinated ethylene-propylene; all FEP tubing used had a 2 mm internal diameter and a 3 mm outer diameter; obtained from Idex Health Science). The outlet from the T mixer was also FEP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. 4 mL of the mixture was loaded into a 5 cc syringe, which was connected to a piece of FEP tubing and in another 5 cc syringe connected to an equal length of FEP tubing, an equal amount of 100 mM citrate buffer (pH 6) was loaded. The two syringes were driven at 7 mL/min flow rate using the syringe pump and the final mixture collected in a 20 mL glass vial (while stirring). Next, the mixture collected from the second mixing step (liposomes) were passed through a Mustang Q membrane (an anion-exchange support that binds and removes anionic molecules, obtained from Pall Corporation). Before using this membrane for the liposomes, 4 mL of 1 M NaOH, 4 mL of 1 M NaCl, and 10 mL of 100 mM citrate buffer (pH 6) were successively passed through it. Liposomes were warmed for 10 min at 37° C. before passing through the membrane. Next, liposomes were concentrated to 2 mL and dialyzed against 10-15 volumes of 1×PBS using by tangential flow filtration before recovering the final product. The TFF system and hollow fiber filtration membranes were purchased from Spectrum Labs (Rancho Dominguez) and were used according to the manufacturer's guidelines. Polysulfone hollow fiber filtration membranes with a 100 kDa pore size cutoff and 8 cm² surface area were used. For in vitro and in vivo experiments formulations were diluted to the required RNA concentration with 1×PBS.

Figure 2:
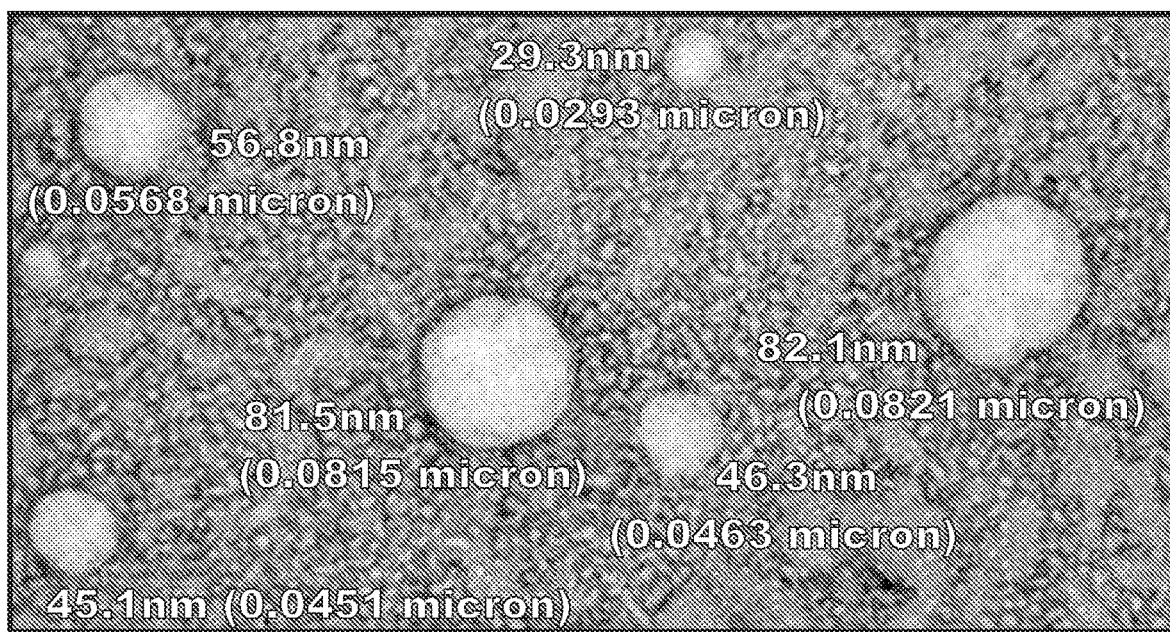
FIG. 2 is an electron micrograph of liposomes.

FIG. 2 shows an example electron micrograph of liposomes prepared by these methods. These liposomes contain encapsulated RNA encoding full-length RSV F antigen. Dynamic light scattering of one batch showed an average diameter of 141 nm (by intensity) or 78 nm (by number).

The percentage of encapsulated RNA and RNA concentration were determined by QUANT-IT™ RIBOGREEN™ RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

Encapsulation in liposomes was shown to protect RNA from RNase digestion. Experiments used 3.8 mAU of RNase A per microgram of RNA, incubated for 30 minutes at room temperature. RNase was inactivated with Proteinase K at 55° C. for 10 minutes. A 1:1 v/v mixture of sample to 25:24:1 v/v/v, phenol:chloroform:isoamyl alcohol was then added to extract the RNA from the lipids into the aqueous phase. Samples were mixed by vortexing for a few seconds and then placed on a centrifuge for 15 minutes at 12k RPM. The aqueous phase (containing the RNA) was removed and used to analyze the RNA. Prior to loading (400 ng RNA per well), all the samples were incubated with formaldehyde loading dye, denatured for 10 minutes at 65° C., and cooled to room temperature. Ambion MILLENNIUM™ markers were used to approximate the molecular weight of the RNA construct. The gel was run at 90 V. The gel was stained using 0.1% SYBR™ gold according to the manufacturer's guidelines in water by rocking at room temperature for 1 hour. FIG. 1 shows that RNase completely digests RNA in the absence of encapsulation (lane 3). RNA is undetectable after encapsulation (lane 4), and no change is seen if these liposomes are treated with RNase (lane 4). After RNase-treated liposomes are subjected to phenol extraction, undigested RNA is seen (lane 6). Even after 1 week at 4° C., the RNA could be seen without any fragmentation (FIG. 4, arrow). Protein expression in vivo was unchanged after 6 weeks at 4° C. and one freeze-thaw cycle. Thus, liposome-encapsulated RNA is stable.

To assess in vivo expression of the RNA, a reporter enzyme (SEAP; secreted alkaline phosphatase) was encoded in the replicon, rather than an immunogen. Expression levels were measured in sera diluted 1:4 in 1× Phospha-Light dilution buffer using a chemiluminescent alkaline phosphate substrate. 8-10 week old BALB/c mice (5/group) were injected intramuscularly on day 0, 50 L per leg with 0.1 μg or 1 μg RNA dose. The same vector was also administered without the liposomes (in RNase free 1×PBS) at 1 μg. Virion-packaged replicons were also tested. Virion-packaged replicons used herein (referred to as "VRPs") were obtained by the methods of reference 51, where the alphavirus replicon is derived from the mutant VEEV or a chimera derived from the genome of VEEV engineered to contain the 3' UTR of Sindbis virus and a Sindbis virus packaging signal (PS), packaged by co-electroporating them into BHK cells with defective helper RNAs encoding the Sindbis virus capsid and glycoprotein genes.

Figure 5:
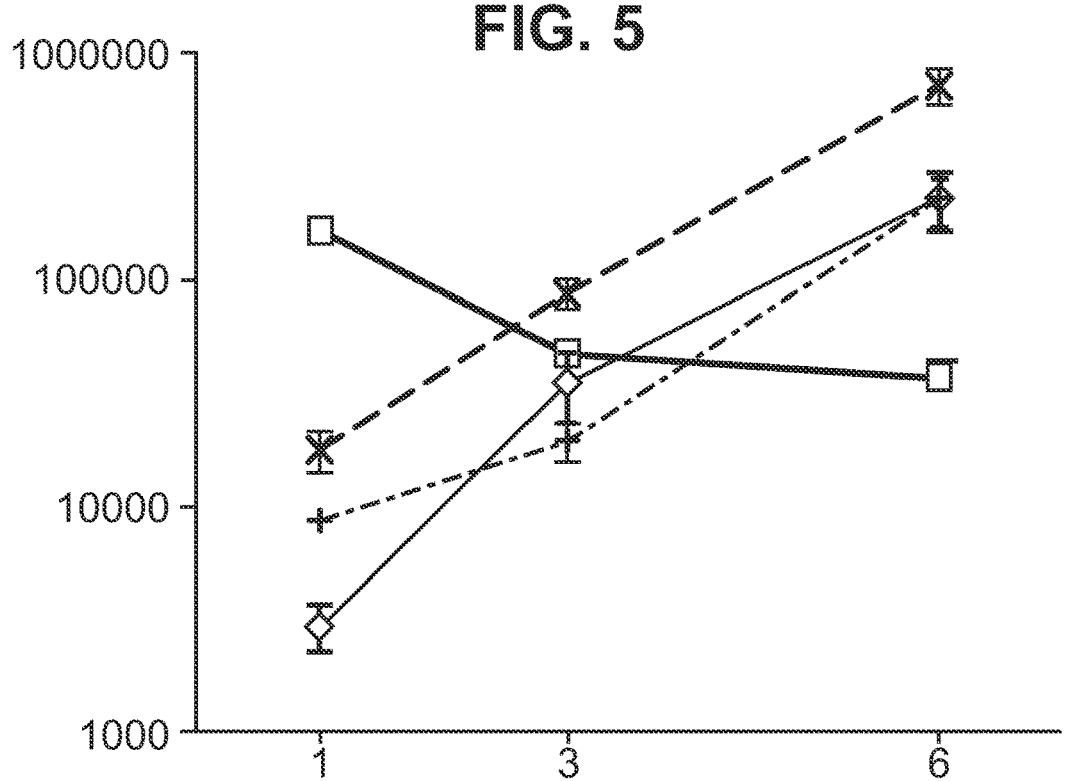
FIG. 5 shows protein expression at days 1, 3, and 6 after delivery of RNA as a virion-packaged replicon (squares), as naked RNA (diamonds), or in liposomes (+=0.1 µg, x=1 µg).

As shown in FIG. 5, encapsulation increased SEAP levels by about ½ log at the 1 μg dose, and at day 6 expression from a 0.1 μg encapsulated dose matched levels seen with 1 μg unencapsulated dose. By day 3, expression levels exceeded those achieved with VRPs (squares). Thus, expression increased when the RNA was formulated in the liposomes relative to the naked RNA control, even at a 10× lower dose. Expression was also higher relative to the VRP control, but the kinetics of expression were very different (see FIG. 5). Delivery of the RNA with electroporation resulted in increased expression relative to the naked RNA control, but these levels were lower than with liposomes.

Figure 10:
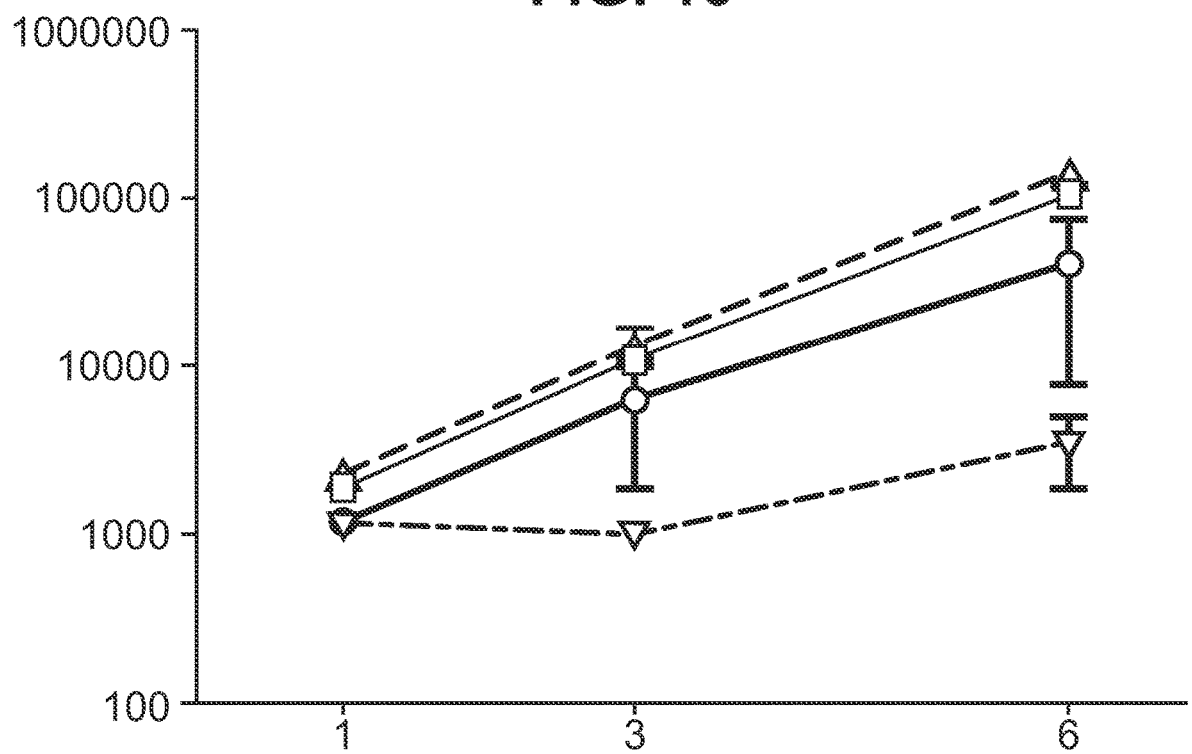
FIG. 10 shows expression levels after delivery of a replicon as naked RNA (circles), liposome-encapsulated RNA (triangle & square), or as a lipoplex (inverted triangle).

To assess whether the effect seen in the liposome groups was due merely to the liposome components, or was linked to the encapsulation, the replicon was administered in encapsulated form (with two different purification protocols, 0.1 μg RNA), or mixed with the liposomes after their formation (a non-encapsulated "lipoplex", 0.1 μg RNA), or as naked RNA (1 μg). FIG. 10 shows that the lipoplex gave the lowest levels of expression, showing that encapsulation is essential for potent expression.

Figure 6:
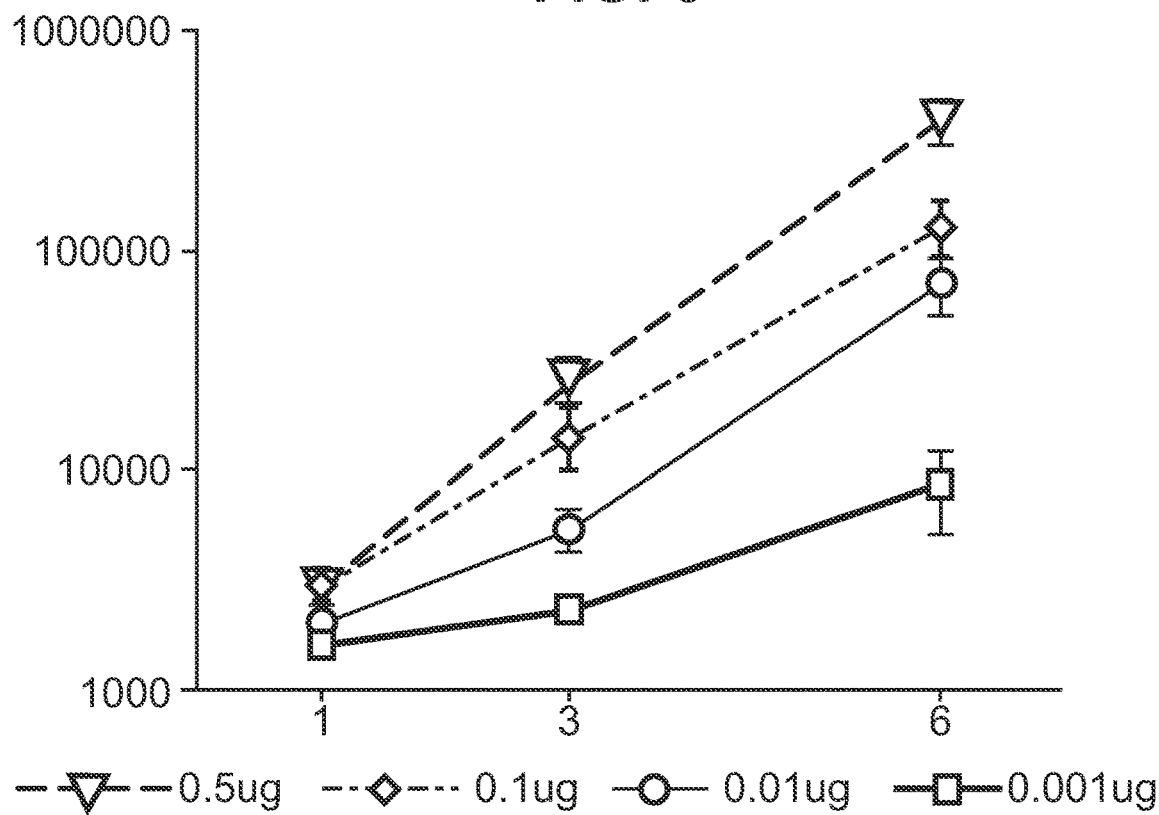
FIG. 6 shows protein expression at days 1, 3, and 6 after delivery of four different doses of liposome-encapsulated RNA.

Further SEAP experiments showed a clear dose response in vivo, with expression seen after delivery of as little as 1 ng RNA (FIG. 6). Further experiments comparing expression from encapsulated and naked replicons indicated that 0.1 μg encapsulated RNA was equivalent to 1 μg of naked RNA. At a 0.5 μg dose of RNA, the encapsulated material gave a 12-fold higher expression at day 6; at a 0.1 μg dose, levels were 24-fold higher at day 6.

Rather than looking at average levels in the group, individual animals were also studied. Whereas several animals were non-responders to naked replicons, encapsulation eliminated non-responders.

Further experiments replaced DlinDMA with DOTAP. Although the DOTAP liposomes gave better expression than naked replicon, they were inferior to the DlinDMA liposomes (2- to 3-fold difference at day 1).

Figure 7:
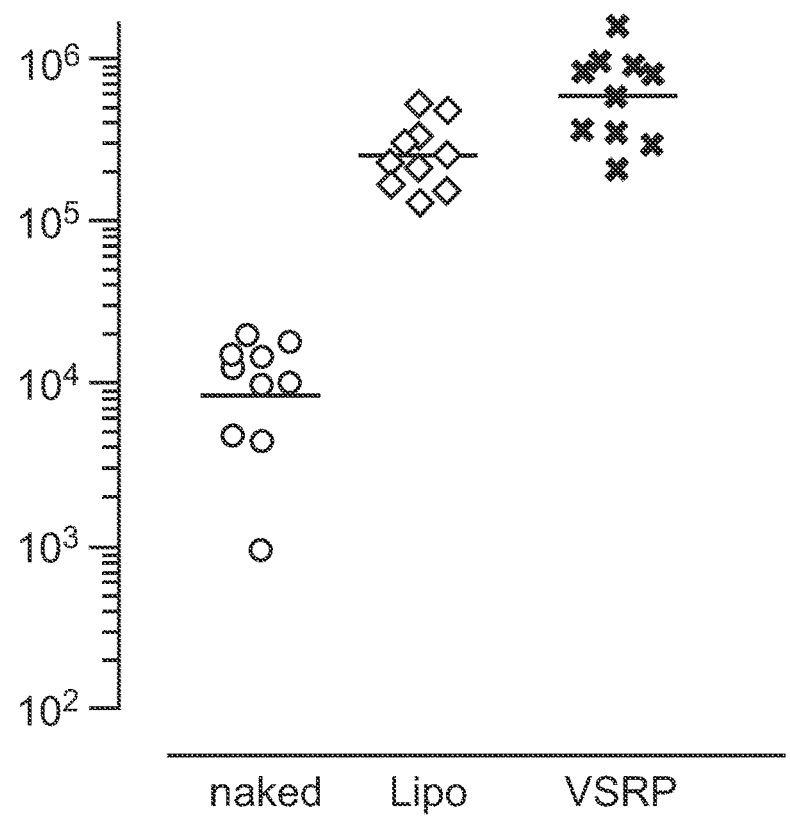
FIG. 7 shows anti-F IgG titers in animals receiving virion-packaged replicon (VRP or VSRP), 1 µg naked RNA, and 1 µg liposome-encapsulated RNA.
Figure 8:
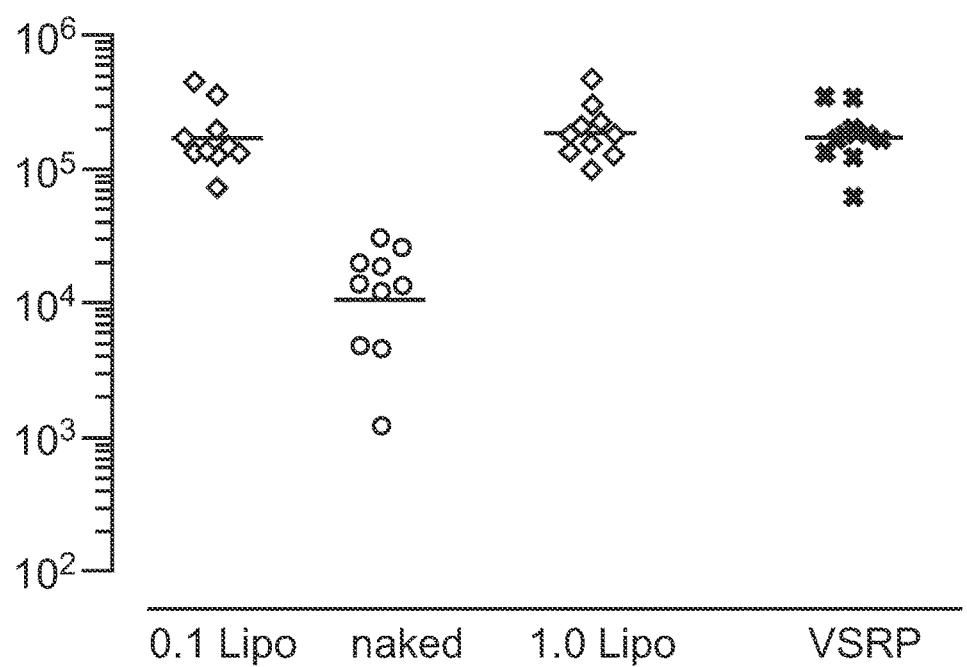
FIG. 8 shows anti-F IgG titers in animals receiving VRP, 1 µg naked RNA, and 0.1 µg or 1 µg liposome-encapsulated RNA.
Figure 9:
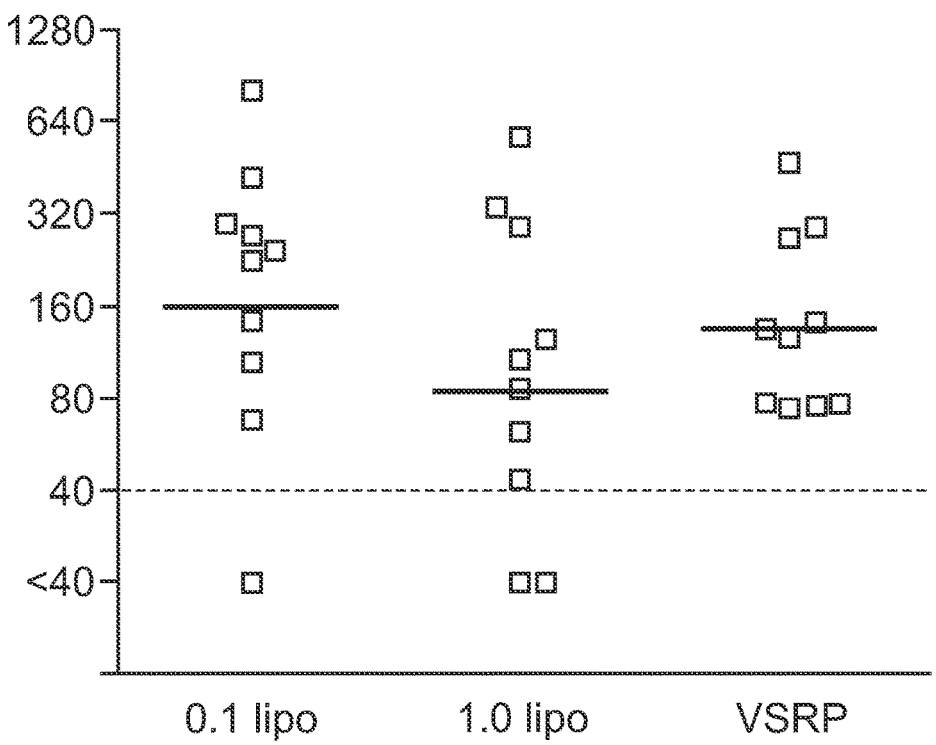
FIG. 9 shows neutralizing antibody titers in animals receiving VRP or either 0.1 µg or 1 µg liposome-encapsulated RNA.
Figure 12:
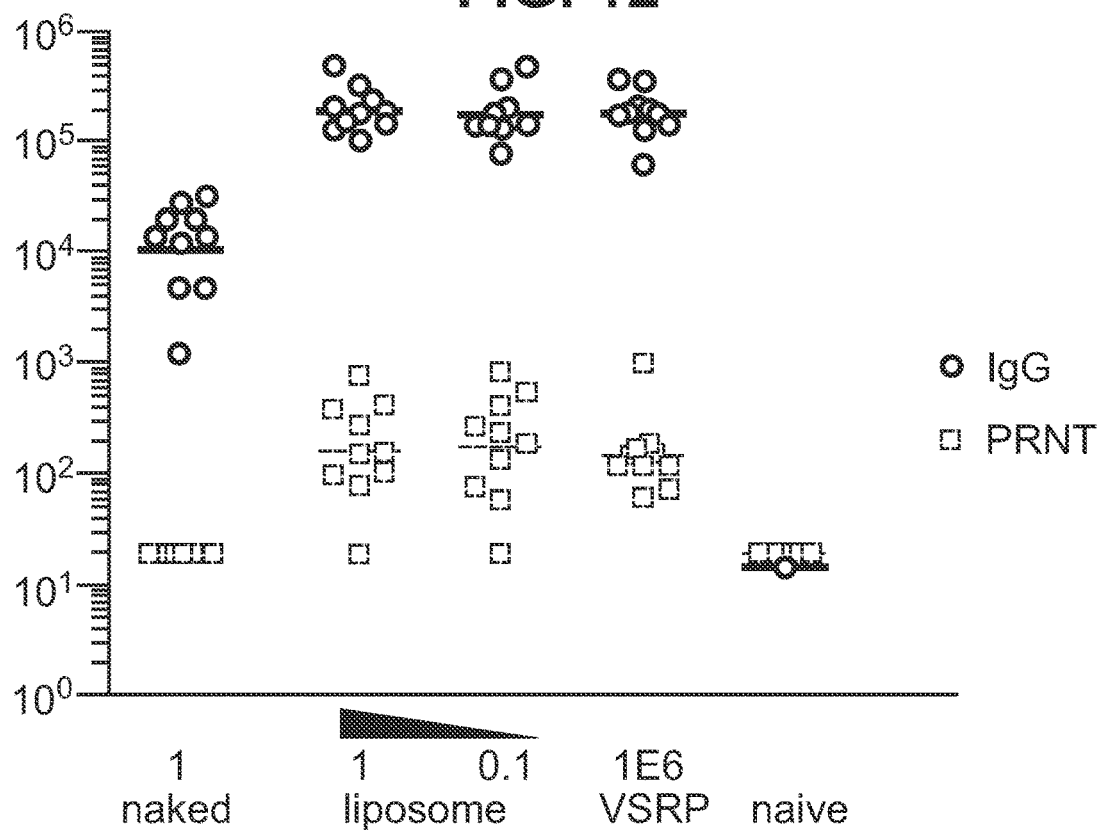
FIG. 12 shows F-specific IgG titers (circles) and PRNT titers (squares) after delivery of a replicon as naked RNA (1 µg), liposome-encapsulated RNA (0.1 or 1 µg), or packaged as a virion (VRP, $10^6$ IU). Titers in naïve mice are also shown. Solid lines show geometric means.

To assess in vivo immunogenicity, a replicon was constructed to express full-length F protein from respiratory syncytial virus (RSV). This was delivered naked (1 μg), encapsulated in liposomes (0.1 or 1 μg), or packaged in virions ($10^6$ IU; "VRP") at days 0 and 21. FIG. 7 shows anti-F IgG titers 2 weeks after the second dose, and the liposomes clearly enhance immunogenicity. FIG. 8 shows titers 2 weeks later, by which point there was no statistical difference between the encapsulated RNA at 0.1 μg, the encapsulated RNA at 1 μg, or the VRP group. Neutralization titers (measured as 60% plaque reduction, "PRNT60") were not significantly different in these three groups 2 weeks after the second dose (FIG. 9). FIG. 12 shows both IgG and PRNT titers 4 weeks after the second dose.

Figure 13:
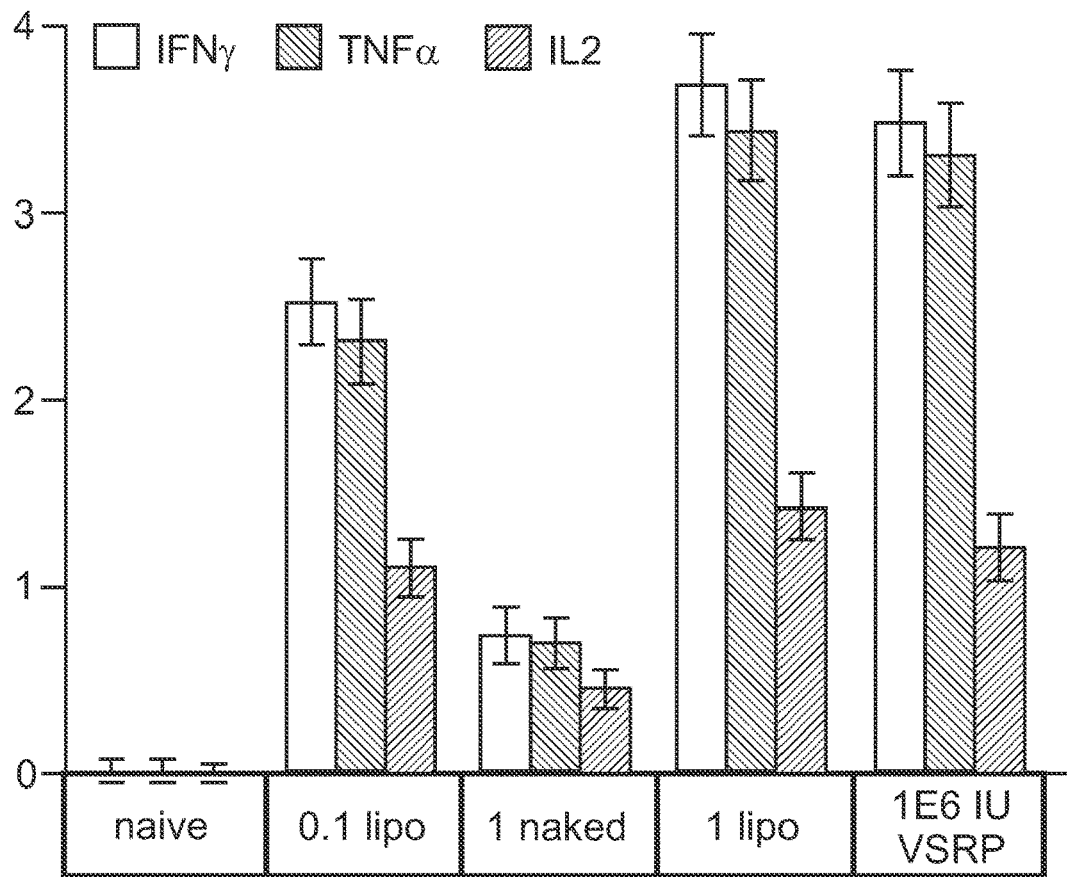
FIG. 13 shows intracellular *cytokine production after restimulation with synthetic peptides representing the major epitopes in the F protein,* 4 weeks after a second dose. The y-axis shows the % cytokine+ of CD8+CD4−.

FIG. 13 confirms that the RNA elicits a robust CD8 T cell response.

Further experiments compared F-specific IgG titers in mice receiving VRP, 0.1 μg liposome-encapsulated RNA, or 1 μg liposome-encapsulated RNA. Titer ratios (VRP:liposome) at various times after the second dose were as follows:

| | 2 weeks | 4 weeks | 8 weeks |
|---|---|---|---|
| 0.1 μg | 2.9 | 1.0 | 1.1 |
| 1 μg | 2.3 | 0.9 | 0.9 |

Thus, the liposome-encapsulated RNA induces essentially the same magnitude of immune response as seen with virion delivery.

Figure 11:
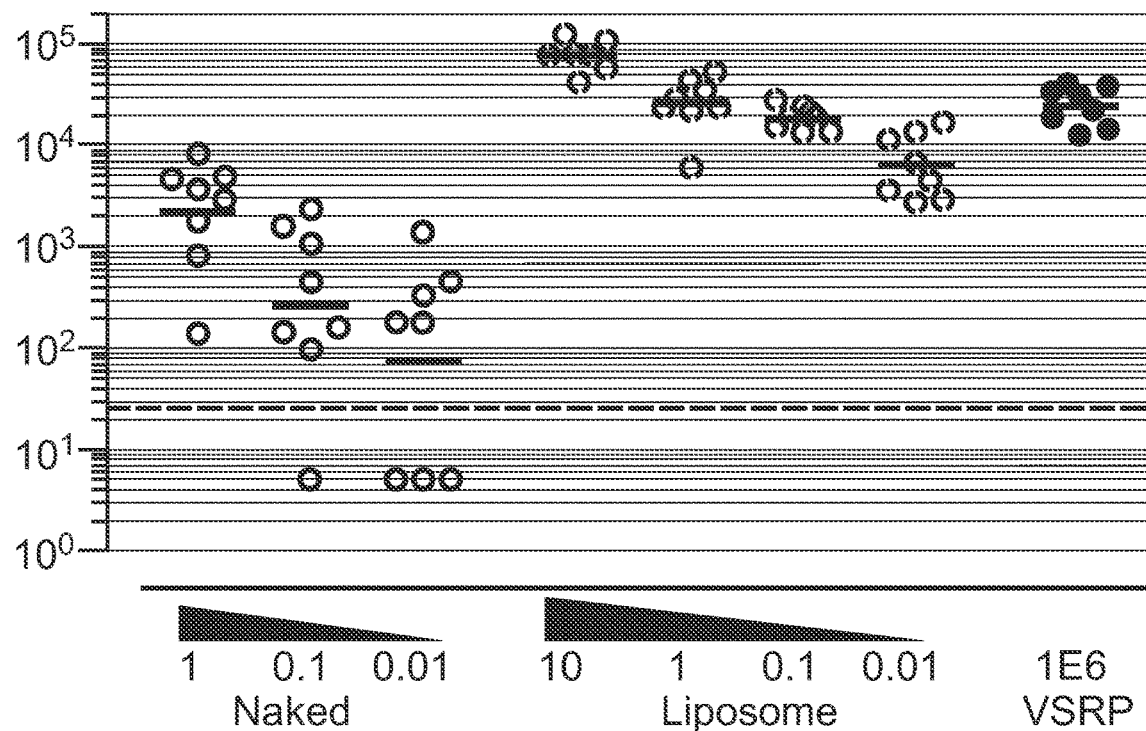
FIG. 11 shows F-specific IgG titers (2 weeks after second dose) after delivery of a replicon as naked RNA (0.01-1 µg), liposome-encapsulated RNA (0.01-10 µg), or packaged as a virion (VRP, $10^6$ infectious units or IU).

Further experiments showed superior F-specific IgG responses with a 10 μg dose, equivalent responses for 1 μg and 0.1 μg doses, and a lower response with a 0.01 μg dose. FIG. 11 shows IgG titers in mice receiving the replicon in naked form at 3 different doses, in liposomes at 4 different doses, or as VRP ($10^6$ IU). The response seen with 1 μg liposome-encapsulated RNA was statistically insignificant (ANOVA) when compared to VRP, but the higher response seen with 10 μg liposome-encapsulated RNA was statistically significant ($p<0.05$) when compared to both of these groups.

A further study confirmed that the 0.1 μg of liposome-encapsulated RNA gave much higher anti-F IgG responses (15 days post-second dose) than 0.1 μg of delivered DNA, and even was more immunogenic than 20 μg plasmid DNA encoding the F antigen, delivered by electroporation (EL-GEN™ DNA Delivery System, Inovio).

A further study was performed in cotton rats (*Sigmodon hispidis*) instead of mice. At a 1 μg dose liposome encapsulation increased F-specific IgG titers by 8.3-fold compared to naked RNA and increased PRNT titers by 9.5-fold. The magnitude of the antibody response was equivalent to that induced by $5\times10^6$ IU VRP. Both naked and liposome-encapsulated RNA were able to protect the cotton rats from RSV challenge (1×10⁵ plaque forming units), reducing lung viral load by at least 3.5 logs. Encapsulation increased the reduction by about 2-fold.

Host Defense Responses at Higher RNA Doses

Mice were used to see if host defense responses (innate or adaptive immunity) might limit the immune response to encoded antigens at higher RNA doses.

Three different RNAs were used for this study: (i) 'vA317' replicon that expresses RSV-F, i.e., the surface fusion glycoprotein of RSV; (ii) 'vA17' replicon that expresses GFP; and (iii) 'vA336' that is replication-defective and encodes GFP.

RNAs were delivered either naked or with liposomes made with 40% DlinDMA, 10% DSPC, 48% Chol, and 2% PEG-DMG (proportions are % moles of total liposome). These liposomes were prepared in 75 μg batches. Fresh lipid stock solutions in ethanol were prepared. 37 mg of DlinDMA, 11.8 mg of DSPC, 27.8 mg of cholesterol, and 8.07 mg of PEG-DMG were weighed and dissolved in 7.55 mL of ethanol. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. This amount of lipids was used to form liposomes with 75 μg RNA. A 2 mL working solution of RNA was also prepared from a stock solution of ~1 μg/μL in 100 mM citrate buffer (pH 6). Three 20 mL glass vials (with stir bars) were rinsed with RNASE AWAY™ solution (Molecular BioProducts) and washed with plenty of MilliQ water before use to decontaminate the vials of RNases. One of the vials was used for the RNA working solution and the others for collecting the lipid and RNA mixes (as described later). The working lipid and RNA solutions were heated at 37° C. for 10 min before being loaded into 3cc syringes. 2 mL of citrate buffer (pH 6) was loaded in another 3 cc syringe. Syringes containing RNA and the lipids were connected to a T mixer (PEEK™ 500 μm ID junction) using FEP tubing. The outlet from the T mixer was also FEP tubing. The third syringe containing the citrate buffer was connected to a separate piece of tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. Then, the mixture was loaded in a 5 cc syringe, which was fitted to a piece of FEP tubing and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, liposomes were concentrated to 2 mL and dialyzed against 10-15 volumes of 1×PBS using TFF before recovering the final product. The TFF system and hollow fiber filtration membranes were purchased from Spectrum Labs and were used according to the manufacturer's guidelines. Polyethersulfone (PES) hollow fiber filtration membranes (part number P-C1-100E-100-01N) with a 100 kDa pore size cutoff and 20 $cm^2$ surface area were used. For in vitro and in vivo experiments, formulations were diluted to the required RNA concentration with 1×PBS.

The four liposome formulations had the following characteristics:

| RNA | Particle Size Zav (nm) | Polydispersity | RNA Encapsulation |
|---|---|---|---|
| vA317 | 155.7 | 0.113 | 86.6% |
| vA17 | 148.4 | 0.139 | 92% |
| vA336 | 145.1 | 0.143 | 92.9% |
| Empty | 147.9 | 0.147 | — |

BALB/c mice, 5 animals per group, were given bilateral intramuscular vaccinations (50 μL per leg) on days 0 and 21 with:

- Group 1 naked self-replicating RSV-F RNA (vA317, 0.1 μg)
- Group 2 self-replicating RSV-F RNA (vA317, 0.1 μg) encapsulated in liposomes
- Group 3 self-replicating RSV-F RNA (vA317, 0.1 μg) added to empty liposomes
- Group 4 a mixture of self-replicating RSV-F RNA (vA317, 0.1 μg) and self-replicating GFP RNA (vA17, 10 μg)
- Group 5 a mixture of self-replicating RSV-F RNA (vA317, 0.1 μg) and replication-defective GFP RNA (vA336, 10 μg)
- Group 6 a mixture of self-replicating RSV-F RNA formulated in liposomes (vA317, 0.1 μg) and self-replicating GFP RNA (vA17, 10 μg)
- Group 7 a mixture of self-replicating RSV-F RNA formulated in liposomes (vA317, 0.1 μg) and replication-defective GFP RNA (vA336, 10 μg)
- Group 8 a mixture of self-replicating RSV-F RNA formulated in liposomes (vA317, 0.1 μg) and self-replicating GFP RNA formulated in liposomes (vA17, 1 μg)
- Group 9 a mixture of self-replicating RSV-F RNA formulated in liposomes (vA317, 0.1 μg) and replication-defective GFP RNA formulated in liposomes (vA336, 1 μg)
- Group 10 F subunit protein (5 μg)

Serum was collected for antibody analysis on days 14, 35, and 51. F-specific serum IgG titers (GMT) were measured; if an individual animal had a titer of <25 (limit of detection), it was assigned a titer of 5. In addition, spleens were harvested from mice at day 51 for T cell analysis, to determine cells which were cytokine-positive and specific for RSV F51-66 peptide (CD4+) or for RSV F peptides F85-93 and F249-258 (CD8+).

IgG titers were as follows in the 10 groups and in non-immunized control mice:

| Day | 1 | 2 | 3 | 4 | 5 | 6 | 7 | 8 | 9 | 10 | — |
|---|---|---|---|---|---|---|---|---|---|---|---|
| 14 | 22 | 1819 | 5 | 5 | 24 | 174 | 1130 | 44 | 347 | 5 | 5 |
| 35 | 290 | 32533 | 9 | 5 | 746 | 6887 | 13171 | 773 | 4364 | 19877 | 5 |
| 51 | 463 | 30511 | 18 | 10 | 1076 | 7201 | 14426 | 922 | 4697 | 20853 | 5 |

RSV serum neutralization titers at day 51 were as follows:

| Day | 1  | 2  | 3  | 4  | 5  | 6  | 7  | 8  | 9  | 10 |
|-----|----|----|----|----|----|----|----|----|----|----|
| 51  | 35 | 50 | 24 | 25 | 31 | 31 | 54 | 34 | 24 | 38 |

Animals showing RSV F-specific CD4+ splenic T cells on day 51 were as follows, where a number (% positive cells) is given only if the stimulated response was statistically significantly above zero:

| Cytokine | 1    | 2    | 3 | 4 | 5    | 6    | 7    | 8    | 9    | 10   |
|----------|------|------|---|---|------|------|------|------|------|------|
| TFN-γ    |      | 0.04 |   |   | 0.02 | 0.02 |      |      |      |      |
| IL2      | 0.02 | 0.06 |   |   | 0.02 | 0.02 |      |      | 0.02 | 0.02 |
| IL5      |      |      |   |   |      |      |      | 0.01 |      |      |
| TNFα     | 0.03 | 0.05 |   |   |      | 0.02 |      |      | 0.02 |      |

Animals showing RSV F-specific CD8+ splenic T cells on day 51 were as follows, where a number is given only if the stimulated response was statistically significantly above zero:

| Cytokine | 1    | 2    | 3 | 4 | 5    | 6    | 7    | 8    | 9    | 10   |
|----------|------|------|---|---|------|------|------|------|------|------|
| IFN-γ    | 0.37 | 0.87 |   |   | 0.37 | 0.40 | 0.49 | 0.06 | 0.54 |      |
| IL2      | 0.11 | 0.40 |   |   | 0.15 | 0.18 | 0.20 | 0.03 | 0.23 | 0.04 |
| IL5      |      |      |   |   |      |      |      |      |      |      |
| TNFα     | 0.29 | 0.79 |   |   | 0.35 | 0.42 | 0.40 |      | 0.53 | 0.06 |

These results show that host defense responses can limit the immune response to the delivered vector. For instance, groups 2 and 6-9 used the same self-replicating antigen-encoding vector, delivered in liposomes, but groups 6-9 also had a 100-fold or 10-fold excess of GFP-encoding vector, delivered either naked or inside liposomes, and either self-replicating or replication-defective. The extra RNA reduced anti-RSV responses, particularly if it was self-replicating and/or encapsulated.

Further experiments aimed to see if host responses to RNA might limit protein expression. Thus, expression was followed for only 6 days, before an adaptive response (antibodies, T cells) would be apparent. The "vA306" replicon encodes SEAP; the "vA17" replicon encodes GFP; the "vA336" replicon encodes GFP but cannot self-replicate; the "vA336*" replicon is the same as vA336 but was prepared with 10% of uridines replaced with 5-methyluridine; the "vA336**" replicon is the same as va336 but 100% of its uridine residues are MSU. BALB/c mice were given bilateral intramuscular vaccinations (50 μL per leg) on day 0. Animals, 35 total, were divided into 7 groups (5 animals per group) and were immunized as follows:

Group 1 Naïve control.

Group 2 were given bilateral intramuscular vaccinations (50 μL per leg) on day 0 with RNA (vA306, 0.1 μg, SEAP) formulated in liposomes mixed with self-replicating RNA (vA17, 1.0 μg, GFP) formulated in liposomes.

Group 3 were given bilateral intramuscular vaccinations (50 μL per leg) on day 0 with RNA (vA306, 0.1 μg, SEAP) formulated in liposomes mixed with non-replicating RNA (vA336, 1.0 μg, GFP) formulated in liposomes.

Group 4 were given bilateral intramuscular vaccinations (50 μL per leg) on day 0 with RNA (vA306, 0.1 μg, SEAP) formulated in liposomes mixed with non-replicating RNA (vA336*, 1.0 μg, GFP) formulated in liposomes.

Group 5 were given bilateral intramuscular vaccinations (50 μL per leg) on day 0 with RNA (vA306, 0.1 μg, SEAP) formulated in liposomes mixed with non-replicating RNA (vA336**, 1.0 μg, GFP) formulated in liposomes.

Group 6 were given bilateral intramuscular vaccinations (50 μL per leg) on day 0 with RNA (vA306, 0.1 μg, SEAP) formulated in liposomes mixed with empty liposomes at the same lipid dose as groups 2-5.

Group 7 were given bilateral intramuscular vaccinations (50 μL per leg) on day 0 with RNA (vA306, 0.1 μg, SEAP) formulated in liposomes mixed with self-replicating RNA (vA17, 1.0 μg, GFP) formulated in liposomes.

Serum SEAP activity (relative light units) at days 0, 3, and 6 were as follows (GMT):

|   | Day 1 | Day 3 | Day 6  |
|---|-------|-------|--------|
| 1 | 898   | 1170  | 2670   |
| 2 | 1428  | 4219  | 28641  |
| 3 | 1702  | 9250  | 150472 |
| 4 | 1555  | 8005  | 76043  |
| 5 | 1605  | 8822  | 91019  |
| 6 | 10005 | 14640 | 93909  |
| 7 | 1757  | 6248  | 53497  |

Replication-competent RNA encoding GFP suppressed the expression of SEAP more than replication-defective GFP RNA, suggesting a strong host defense response against replicating RNA which leads to suppression of SEAP expression. It is possible that interferons induced in response to the GFP RNA suppressed the expression of SEAP. Under the host response/suppression model, blocking host recognition of RNA would be expected to lead to increased SEAP expression, but 5' methylation of U residues in the GFP RNA was not associated with increased SEAP, suggesting that host recognition of RNA was insensitive to 5' methylation.

Delivery Volume

Hydrodynamic delivery employs the force generated by the rapid injection of a large volume of solution to overcome the physical barriers of cell membranes which prevent large and membrane-impermeable compounds from entering cells. This phenomenon has previously been shown to be useful for the intracellular delivery of DNA vaccines.

A typical mouse delivery volume for intramuscular injection is 50 μL into the hind leg, which is a relatively high volume for a mouse leg muscle. In contrast, a human intramuscular dose of ~0.5 mL is relatively small. If immunogenicity in mice would be volume-dependent, then the replicon vaccines' efficacy might be due, at least in part, on hydrodynamic forces, which would not be encouraging for use of the same vaccines in humans and larger animals.

The vA317 replicon was delivered to BALB/c mice, 10 per group, by bilateral intramuscular vaccinations (5 or 50 μL per leg) on day 0 and 21:

Group 1 received naked replicon, 0.2 μg in 50 μL per leg
Group 2 received naked replicon, 0.2 μg in 5 μL per leg
Group 3 received emulsion-formulated replicon (0.2 μg, 50 μL per leg)
Group 4 received emulsion-formulated replicon (0.2 μg, 5 μL per leg)
Group 5 received liposome-formulated replicon (0.2 μg, 50 μL per leg)
Group 6 received liposome-formulated replicon (0.2 μg, 5 μL per leg)

Serum was collected for antibody analysis on days 14 and 35. F-specific serum IgG GMTs were:

| Day | 1 | 2 | 3 | 4 | 5 | 6 |
| --- | --- | --- | --- | --- | --- | --- |
| 14 | 42 | 21 | 783 | 760 | 2669 | 2610 |
| 35 | 241 | 154 | 2316 | 2951 | 17655 | 18516 |

Thus, immunogenicity of the formulated replicon did not vary according to the delivered volume, thus indicating that these RNA vaccines do not rely on hydrodynamic delivery for their efficacy.

Large Mammal Study

A large-animal study was performed in cattle. Calves (4-6 weeks old, ~60-80 kg, 5 per group) were immunized with 66 μg of replicon vA317 encoding full-length RSV F protein at days 0, 21, 86, and 146. The replicons were formulated either inside liposomes or with the CNE17 emulsion. PBS alone was used as a negative control, and a licensed vaccine was used as a positive control ("Triangle 4" from Fort Dodge, containing killed virus). All calves received 15 μg F protein adjuvanted with the MF59™ emulsion on day 146. One cow was mistakenly vaccinated with the CNE17-based vaccine on day 86 instead of Triangle 4 and so its data were excluded from day 100 onwards.

The RNA vaccines encoded human RSV F whereas the "Triangle 4" vaccine contains bovine RSV F, but the RSV F protein is highly conserved between BRSV and HRSV.

The liposomes had the same proportion of DlinDMA, DSPC, cholesterol, and PEG-DMG as mentioned above. Fresh lipid stock solutions in ethanol were prepared. 37 mg of DlinDMA, 11.8 mg of DSPC, 27.8 mg of cholesterol, and 8.07 mg of PEG-DMG were weighed and dissolved in 7.55 mL of ethanol. The freshly prepared lipid stock solution was gently rocked at 37° C. for about 15 min to form a homogenous mixture. Then, 226.7 μL of the stock was added to 1.773 mL ethanol to make a working lipid stock solution of 2 mL. A 2 mL working solution of RNA was also prepared from a stock solution of ~1 μg/μL in 100 mM citrate buffer (pH 6). Three 20 mL glass vials (with stir bars) were rinsed with RNASE AWAY™ solution (Molecular BioProducts) and washed with plenty of MilliQ water before use to decontaminate the vials of RNAses. One of the vials was used for the RNA working solution and the others for collecting the lipid and RNA mixes (as described later). The working lipid and RNA solutions were heated at 37° C. for 10 min before being loaded into 3cc syringes. 2 mL of citrate buffer (pH 6) was loaded in another 3 cc syringe. Syringes containing RNA and the lipids were connected to a T mixer (PEEK™ 500 μmID junction) using FEP tubing. The outlet from the T mixer was also FEP tubing. The third syringe containing the citrate buffer was connected to a separate piece of FEP tubing. All syringes were then driven at a flow rate of 7 mL/min using a syringe pump. The tube outlets were positioned to collect the mixtures in a 20 mL glass vial (while stirring). The stir bar was taken out and the ethanol/aqueous solution was allowed to equilibrate to room temperature for 1 h. Then, the mixture was loaded in a 5 cc syringe, which was fitted to a piece of FEP tubing and in another 5 cc syringe with equal length of FEP tubing, an equal volume of 100 mM citrate buffer (pH 6) was loaded. The two syringes were driven at 7 mL/min flow rate using a syringe pump and the final mixture collected in a 20 mL glass vial (while stirring). Next, the mixture collected from the second mixing step (liposomes) was passed through a Mustang Q membrane (an anion-exchange support that binds and removes anionic molecules, obtained from Pall Corporation, Ann Arbor, MI, USA). Before passing the liposomes, 4 mL of 1 M NaOH, 4 mL of 1 M NaCl, and 10 mL of 100 mM citrate buffer (pH 6) were successively passed through the Mustang membrane. Liposomes were warmed for 10 min at 37° C. before passing through the filter. Next, liposomes were concentrated to 2 mL and dialyzed against 10-15 volumes of 1×PBS using TFF system before recovering the final product. The TFF system and hollow fiber filtration membranes were purchased from Spectrum Labs and were used according to the manufacturer's guidelines. Polyethersulfone (PES) hollow fiber filtration membranes with a 100 kDa pore size cutoff and 20 cm² surface area were used. For in vitro and in vivo experiments formulations were diluted to the required RNA concentration with 1×PBS.

Calves received 2 mL of each experimental vaccine, administered intramuscularly as 2×1 mL on each side of the neck. In contrast, the "Triangle 4" vaccine was given as a single 2 mL dose in the neck.

Serum was collected for antibody analysis on days 0, 14, 21, 35, 42, 56, 63, 86, 100, 107, 114, 121, 128, 135, 146, 160, 167, 174, 181, 188, 195, and 202. If an individual animal had a titer below the limit of detection it was assigned a titer of 5

Figure 14A:
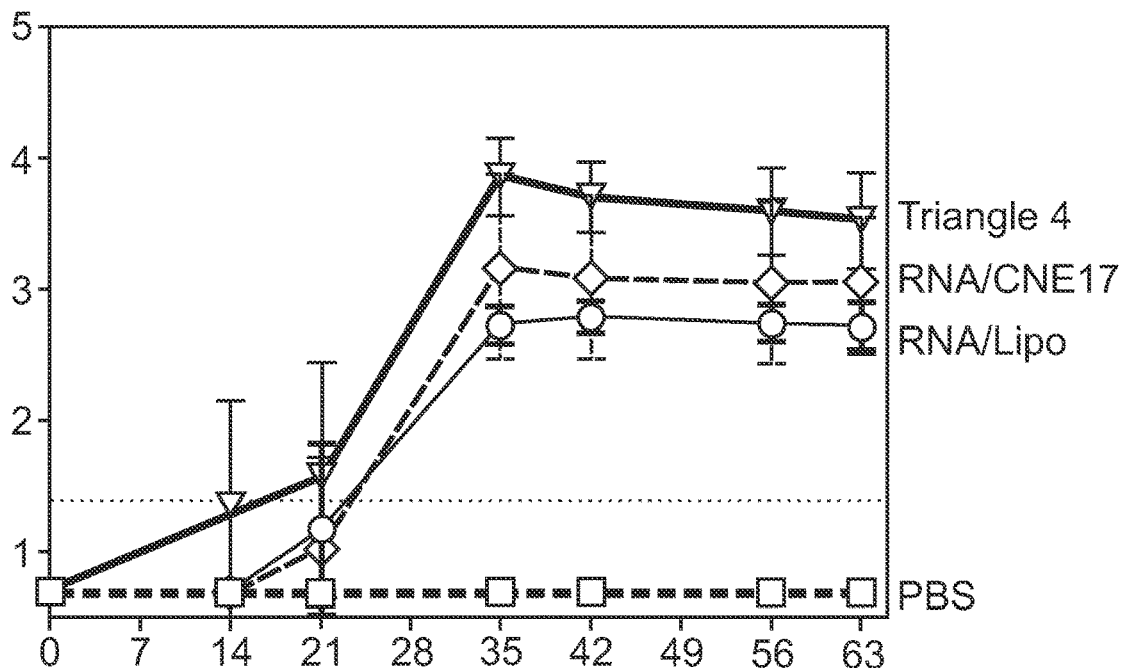

FIG. 14A shows F-specific IgG titers over the first 63 days. The RNA replicon was immunogenic in the cows using both delivery systems, although it gave lower titers than the licensed vaccine. All vaccinated cows showed F-specific antibodies after the second dose, and titers were very stable from the period of 2 to 6 weeks after the second dose (and were particularly stable for the RNA vaccines). The titers with the liposome delivery system were more tightly clustered than with the emulsion.

FIG. 14B shows F-specific serum IgG titers (GMT) over 210 days, and measured values up to day 202 were as follows:

|        | D 0 | 3wp1 D 21 | 2wp2 D 35 | 5wp2 D 56 | ~9wp2 D 86 | 2wp3 D 100 | 5wp3 D 121 | 8wp3 D 146 | 2wp4 D 160 | 5wp4 D 181 | 8wp4 D 202 |
|--------|-----|-----------|-----------|-----------|------------|------------|------------|------------|------------|------------|------------|
| PBS    | 5   | 5         | 5         | 5         | 5          | 5          | 5          | 5          | 46         | 98         | 150        |
| Liposome | 5 | 5         | 12        | 11        | 20         | 768        | 428        | 74         | 20774      | 7022       | 2353       |
| CNE17  | 5   | 5         | 34        | 46        | 56         | 773        | 538        | 70         | 8297       | 4843       | 2073       |
| Triangle 4 | 5 | 5       | 1784      | 721       | 514        | 3406       | 2786       | 336        | 13376      | 4775       | 2133       |

The emulsion-adjuvanted vaccine induced a neutralizing response when assayed without complement, with higher titers than Triangle 4 (although more variable). RSV serum neutralizing antibody titers were as follows:

|        | D 0 | 2wp2 D 35 | 5wp2 D 56 | 2wp3 D 100 | 3wp3 D 107 | 4wp3 D 114 | 8wp3 D 146 | 2wp4 D 160 | 3wp4 D 167 | 4wp4 D 174 |
|--------|-----|-----------|-----------|------------|------------|------------|------------|------------|------------|------------|
| PBS    | 12  | 10        | 10        | 14         | 18         | 20         | 14         | 10         | 10         | 10         |
| Liposome | 13 | 10       | 10        | 20         | 13         | 17         | 13         | 47         | 26         | 21         |
| CNE17  | 10  | 10        | 13        | 28         | 44         | 52         | 14         | 64         | 57         | 40         |
| Triangle 4 | 12 | 15     | 13        | 39         | 38         | 41         | 13         | 24         | 26         | 15         |

The data from this study provide proof of concept for RNA replicon RSV vaccines in large animals, with two of the five calves in the emulsion-adjuvanted group demonstrating good neutralizing antibody titers after the third vaccination, as measured by the complement-independent HRSV neutralization assay. Although the emulsion-adjuvanted vaccines appear to be more immunogenic than the liposome-adjuvanted vaccines, one complicating factor is that the material used for the second liposome dose was not freshly prepared, and the same lot of RNA showed a decrease in potency in a mouse immunogenicity study. Therefore, it is possible that the liposome-adjuvanted vaccine would have been more immunogenic if fresh material had been used for all vaccinations.

When assayed with complement, neutralizing antibodies were detected in all vaccinated cows. In this assay, all vaccinated calves had good neutralizing antibody titers after the second RNA vaccination regardless of the formulation. Furthermore, both RNA vaccines elicited F-specific serum IgG titers that were detected in a few calves after the second vaccination and in all calves after the third.

MF59™-adjuvanted RSV-F was able to boost the IgG response in all previously vaccinated calves, and to boost complement-independent HRSV neutralization titers of calves previously vaccinated with RNA.

Proof of concept for RNA vaccines in large animals is particularly important in light of the loss in potency observed previously with DNA-based vaccines when moving from small animal models to larger animals and humans. A typical dose for a cow DNA vaccine would be 0.5-1 mg (see references [52] and [53]) and so it is very encouraging that immune responses were induced with only 66 μg of RNA.

It will be understood that the invention has been described by way of example only and modifications may be made whilst remaining within the scope and spirit of the invention.

TABLE 1

| useful phospholipids | |
|---|---|
| DDPC | 1,2-Didecanoyl-sn-Glycero-3-phosphatidylcholine |
| DEPA | 1,2-Dierucoyl-sn-Glycero-3-Phosphate |
| DEPC | 1,2-Erucoyl-sn-Glycero-3-phosphatidylcholine |
| DEPE | 1,2-Dierucoyl-sn-Glycero-3-phosphatidylethanolamine |
| DEPG | 1,2-Dierucoyl-sn-Glycero-3 [Phosphatidyl-rac-(1-glycerol . . .) |
| DLOPC | 1,2-Linoleoyl-sn-Glycero-3-phosphatidylcholine |
| DLPA | 1,2-Dilauroyl-sn-Glycero-3-Phosphate |
| DLPC | 1,2-Dilauroyl-sn-Glycero-3-phosphatidylcholine |
| DLPE | 1,2-Dilauroyl-sn-Glycero-3-phosphatidylethanolamine |
| DLPG | 1,2-Dilauroyl-sn-Glycero-3 [Phosphatidyl-rac-(1-glycerol . . .) |
| DLPS | 1,2-Dilauroyl-sn-Glycero-3-phosphatidylserine |
| DMG | 1,2-Dimyristoyl-sn-glycero-3-phosphoethanolamine |
| DMPA | 1,2-Dimyristoyl-sn-Glycero-3-Phosphate |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG | 1,2-Myristoyl-sn-Glycero-3 [Phosphatidyl-rac-(1-glycerol . . .) |
| DMPS | 1,2-Dimyristoyl-sn-Glycero-3-phosphatidylserine |
| DOPA | 1,2-Dioleoyl-sn-Glycero-3-Phosphate |
| DOPC | 1,2-Dioleoyl-sn-Glycero-3-phosphatidylcholine |
| DOPE | 1,2-Dioleoyl-sn-Glycero-3-phosphatidylethanolamine |
| DOPG | 1,2-Dioleoyl-sn-Glycero-3 [Phosphatidyl-rac-(1-glycerol . . .) |
| DOPS | 1,2-Dioleoyl-sn-Glycero-3-phosphatidylserine |
| DPPA | 1,2-Dipalmitoyl-sn-Glycero-3-Phosphate |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG | 1,2-Dipalmitoyl-sn-Glycero-3 [Phosphatidyl-rac-(1-glycerol . . .) |
| DPPS | 1,2-Dipalmitoyl-sn-Glycero-3-phosphatidylserine |

TABLE 1-continued useful phospholipids

| | |
|---|---|
| DPyPE | 1,2-diphytanoyl-sn-glycero-3-phosphoethanolamine |
| DSPA | 1,2-Distearoyl-sn-Glycero-3-Phosphate |
| DSPC | 1,2-Distearoyl-sn-Glycero-3-phosphatidylcholine |
| DSPE | 1,2-Diostearpyl-sn-Glycero-3-phosphatidylethanolamine |
| DSPG | 1,2-Distearoyl-sn-Glycero-3 [Phosphatidyl-rac-(1-glycerol . . .) |
| DSPS | 1,2-Distearoyl-sn-Glycero-3-phosphatidylserine |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl-2-oleoyl-sn-Glycero-3-phosphatidylethanolamine |
| POPG | 1,2-Dioleoyl-sn-Glycero-3 [Phosphatidyl-rac-(1-glycerol) . . .] |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

REFERENCES

[1] Johanning et al. (1995) *Nucleic Acids Res* 23:1495-1501.
[2] Martinon et al. (1993) *Eur J Immunol* 22:1719-22.
[3] Ying et al. (1999) *Nature Medicine* 5:823-27.
[4] Saxena et al. (2009) *Vet Microbiol* 136:36-44.
[5] Jones et al. (2009) *Vaccine* 27:2506-12.
[6] Heyes et al. (2005) *J Controlled Release* 107:276-87.
[7] WO2005/121348.
[8] *Liposomes: Methods and Protocols, Volume 1: Pharmaceutical Nanocarriers: Methods and Protocols.* (ed. Weissig). Humana Press, 2009. ISBN 160327359X.
[9] *Liposome Technology*, volumes I, II & III. (ed. Gregoriadis). Informa Healthcare, 2006.
[10] *Functional Polymer Colloids and Microparticles volume 4* (Microspheres, microcapsules & liposomes). (eds. Arshady & Guyot). Citus Books, 2002.
[11] Jeffs et al. (2005) *Pharmaceutical Research* 22 (3):362-372.
[12] *Polymers in Drug Delivery*. (eds. Uchegbu & Schatzlein). CRC Press, 2006.
[13] *Microparticulate Systems for the Delivery of Proteins and Vaccines.* (eds. Cohen & Bernstein). CRC Press, 1996.
[14] O'Hagan et al. (2001) *J Virology* 75:9037-9043.
[15] Singh et al. (2003) *Pharmaceutical Research* 20: 247-251.
[16] WO2009/132206.
[17] US-2008/0085870.
[18] US-2008/0057080.
[19] US-2007/0014805.
[20] WO2005/113782.
[21] WO2011/005799.
[22] El Ouahabi et al. (1996) *FEBS Letts* 380:108-12.
[23] Giuliani et al. (2006) *Proc Natl Acad Sci USA* 103(29): 10834-9.
[24] WO2009/016515.
[25] WO02/34771.
[26] WO2005/032582.
[27] WO/2010/119343.
[28] WO2006/110413.
[29] WO2005/111066.
[30] WO2005/002619.
[31] WO2006/138004.
[32] WO2009/109860.
[33] WO02/02606.
[34] WO03/018054.
[35] WO2006/091517.
[36] WO2008/020330.
[37] WO2006/089264.
[38] WO2009/104092.
[39] WO2009/031043.
[40] WO2007/049155.
[41] Gennaro (2000) *Remington: The Science and Practice of Pharmacy.* 20th edition, ISBN: 0683306472.
[42] *Methods In Enzymology* (S. Colowick and N. Kaplan, eds., Academic Press, Inc.)
[43] *Handbook of Experimental Immunology*, Vols. I-IV (D. M. Weir and C. C. Blackwell, eds, 1986, Blackwell Scientific Publications)
[44] Sambrook et al. (2001) *Molecular Cloning: A Laboratory Manual,* 3rd edition (Cold Spring Harbor Laboratory Press).
[45] *Handbook of Surface and Colloidal Chemistry* (Birdi, K. S. ed., CRC Press, 1997)
[46] Ausubel et al. (eds) (2002) *Short protocols in molecular biology,* 5th edition (Current Protocols).
[47] *Molecular Biology Techniques: An Intensive Laboratory Course*, (Ream et al., eds., 1998, Academic Press)
[48] *PCR (Introduction to Biotechniques Series)*, 2nd ed. (Newton & Graham eds., 1997, Springer Verlag)
[49] Yoneyama & Fujita (2007) *Cytokine & Growth Factor Reviews* 18:545-51.
[50] Maurer et al. (2001) *Biophysical Journal,* 80: 2310-2326.
[51] Perri et al. (2003) *J Virol* 77:10394-10403.
[52] Boxus et al. (2007) *J Virol* 81:6879-89.
[53] Taylor et al. (2005) *Vaccine* 23:1242-50.

The invention claimed is:

1. A method of eliciting an antibody response against a respiratory syncytial virus (RSV) surface fusion glycoprotein (F protein) immunogen by an immune system in a large mammal, the method comprising administering intramuscularly to the large mammal at least two unit doses; each unit dose comprising a composition comprising liposomes and messenger ribonucleic acid (mRNA) molecules; the mRNA molecules comprising a poly-adenosine monophosphate (poly(A)) tail and a sequence that encodes the RSV F protein immunogen; each unit dose comprising between 2 µg and 100 µg of the mRNA molecules; the at least two unit doses being sequential and administered at least 1 week apart; the administering comprising contacting the composition with skeletal muscle; the liposomes comprising a cationic lipid; the cationic lipid comprising a tertiary amine; the liposomes encapsulating at least half of the mRNA molecules; and the large mammal being a human or a cow.

2. The method of claim 1, the mRNA molecules comprising a 5' cap nucleoside, a first 5' ribonucleoside, and a triphosphate bridge; the 5' cap nucleoside being linked 5'-to-5' to the first 5' ribonucleoside by the triphosphate bridge; the 5' cap nucleoside optionally being a 7-methylguanosine; and the large mammal being the human.

3. The method of claim 2, the liposomes further comprising: i) an anionic phospholipid or a zwitterionic phospholipid and ii) cholesterol.

4. The method of claim 2, the mRNA molecules comprising a modified nucleotide.

5. The method of claim 4, the modified nucleotide being a modified pyrimidine nucleotide.

6. The method of claim 5, the liposomes further comprising 1,2-distearoyl-sn-glycero-3-phosphocholine and cholesterol.

7. The method of claim 4, the liposomes further comprising 1,2-distearoyl-sn-glycero-3-phosphocholine and cholesterol.

8. The method of claim 7 comprising administering to the human at least three unit doses.

9. The method of claim 2, the liposomes further comprising 1,2-distearoyl-sn-glycero-3-phosphocholine and cholesterol.

10. The method of claim 9 comprising administering to the human at least three unit doses.

11. The method of claim 1, at least 80% of the liposomes having diameters from 20 nm to 220 nm.

12. The method of claim 11, the liposomes further comprising 1,2-distearoyl-sn-glycero-3-phosphocholine and cholesterol; and the large mammal being the human.

13. The method of claim 12 comprising administering to the human at least three unit doses.

14. The method of claim 1, the liposomes further comprising 1,2-distearoyl-sn-glycero-3-phosphocholine and cholesterol; and the large mammal being the human.

15. The method of claim 14 comprising administering to the human at least three unit doses.

16. A method of eliciting an antibody response against a RSV F protein immunogen by an immune system in a large mammal, the method comprising administering intramuscularly to the large mammal at least two unit doses, each unit dose comprising a composition comprising liposomes and mRNA molecules; the mRNA molecules comprising a poly (A) tail and a sequence that encodes the RSV F protein immunogen; each unit dose comprising between 0.5 µg and 1.5 µg of the mRNA molecules per kg of the body mass of the large mammal; the at least two unit doses being sequential and administered at least 1 week apart; the administering comprising contacting the composition with skeletal muscle; the liposomes comprising a cationic lipid; the cationic lipid comprising a tertiary amine; the liposomes encapsulating at least half of the mRNA molecules; and the large mammal being a human or a cow.

17. The method of claim 16, the mRNA molecules comprising a 5' cap nucleoside, a first 5' ribonucleoside, and a triphosphate bridge; the 5' cap nucleoside being linked 5'-to-5' to the first 5' ribonucleoside by the triphosphate bridge; the 5' cap nucleoside optionally being a 7-methylguanosine; and the large mammal being the human.

18. The method of claim 17, the liposomes further comprising: i) an anionic phospholipid or a zwitterionic phospholipid and ii) cholesterol.

19. The method of claim 17, the mRNA molecules comprising a modified nucleotide.

20. The method of claim 19, the modified nucleotide being a modified pyrimidine nucleotide.

21. The method of claim 20, the liposomes further comprising 1,2-distearoyl-sn-glycero-3-phosphocholine and cholesterol.

22. The method of claim 19, the liposomes further comprising 1,2-distearoyl-sn-glycero-3-phosphocholine and cholesterol.

23. The method of claim 22 comprising administering to the human at least three unit doses.

24. The method of claim 17, the liposomes further comprising 1,2-distearoyl-sn-glycero-3-phosphocholine and cholesterol.

25. The method of claim 24 comprising administering to the human at least three unit doses.

26. The method of claim 16, at least 80% of the liposomes having diameters from 20 nm to 220 nm.

27. The method of claim 26, the liposomes further comprising 1,2-distearoyl-sn-glycero-3-phosphocholine and cholesterol; and the large mammal being the human.

28. The method of claim 27 comprising administering to the human at least three unit doses.

29. The method of claim 16, the liposomes further comprising 1,2-distearoyl-sn-glycero-3-phosphocholine and cholesterol; and the large mammal being the human.

30. The method of claim 29 comprising administering to the human at least three unit doses.

* * * * *